US012264203B2

(12) United States Patent
Viswanathan et al.

(10) Patent No.: US 12,264,203 B2
(45) Date of Patent: Apr. 1, 2025

(54) HUMANIZED COMPLEMENT 5a RECEPTOR 1 ANTIBODIES AND METHODS OF USE THEREOF

(71) Applicant: VISTERRA, INC., Waltham, MA (US)

(72) Inventors: Karthik Viswanathan, Waltham, MA (US); Brian Booth, Waltham, MA (US); Boopathy Ramakrishnan, Waltham, MA (US); Andrew Wollacott, Waltham, MA (US); Gregory Babcock, Waltham, MA (US); Zachary Shriver, Waltham, MA (US); Lauren Olinski, Waltham, MA (US)

(73) Assignee: Visterra, Inc., Waltham, MA (US)

( * ) Notice: Subject to any disclaimer, the term of this patent is extended or adjusted under 35 U.S.C. 154(b) by 0 days.

(21) Appl. No.: 18/731,146

(22) Filed: May 31, 2024

(65) Prior Publication Data
US 2024/0392029 A1    Nov. 28, 2024

Related U.S. Application Data

(62) Division of application No. 18/415,419, filed on Jan. 17, 2024, which is a division of application No. (Continued)

(51) Int. Cl.
C07K 16/28 (2006.01)
A61K 39/00 (2006.01)
A61P 37/02 (2006.01)

(52) U.S. Cl.
CPC .......... C07K 16/2896 (2013.01); A61P 37/02 (2018.01); A61K 2039/505 (2013.01);
(Continued)

(58) Field of Classification Search
CPC ............ C07K 16/2896; C07K 2317/24; C07K 2317/33; C07K 2317/52; C07K 2317/565;
(Continued)

(56) References Cited

U.S. PATENT DOCUMENTS 5,480,974 A    1/1996   Morgan et al.
7,317,091 B2   1/2008   Lazar et al.
(Continued)

FOREIGN PATENT DOCUMENTS

CN    110072887 A     7/2019
EP      1587540 A2   10/2005
(Continued)

OTHER PUBLICATIONS

International Search Report and Written Opinion for PCT/US2021/013284 dated May 4, 2021 (13 pages).
(Continued)

Primary Examiner — Aurora M Fontainhas
Assistant Examiner — Selam Berhane
(74) Attorney, Agent, or Firm — Proskauer Rose LLP

(57) ABSTRACT

The present disclosure provides, among other things, two different formats of humanized antibodies against human complement component 5a receptor I. The disclosure also provides a method of treating a subject having dysfunctions of C5a/C5aR1 axis pathway, including but not limited to ANCA-associated vasculitis, comprising administering to the subject in need thereof an effective amount of antibody or a nucleic encoding an antibodies binding to C5aR1 described herein, and wherein administering results in a decrease in symptoms associated with C5a/C5aR1 associated dysfunction in the subject.

13 Claims, 42 Drawing Sheets

Specification includes a Sequence Listing.

Related U.S. Application Data

17/575,420, filed on Jan. 13, 2022, now Pat. No. 11,912,781.

(60) Provisional application No. 63/274,748, filed on Nov. 2, 2021, provisional application No. 63/137,089, filed on Jan. 13, 2021.

(52) U.S. Cl.
CPC ...... C07K 2317/24 (2013.01); C07K 2317/33 (2013.01); C07K 2317/52 (2013.01); C07K 2317/565 (2013.01); C07K 2317/76 (2013.01); C07K 2317/77 (2013.01); C07K 2317/92 (2013.01)

(58) Field of Classification Search
CPC ............ C07K 2317/76; C07K 2317/77; C07K 2317/92; A61P 37/02; A61K 2039/505
See application file for complete search history.

(56) References Cited

U.S. PATENT DOCUMENTS

| | | | |
|---|---|---|---|
| 7,455,837 B2 | 11/2008 | Guo et al. |
| 7,632,497 B2 | 12/2009 | Stavenhagen |
| 7,863,419 B2 | 1/2011 | Taylor et al. |
| 8,071,096 B2 | 12/2011 | Mackay |
| 8,071,839 B2 | 12/2011 | Mackay |
| 8,084,024 B2 | 12/2011 | Mackay |
| 8,084,582 B2 | 12/2011 | Dahiyat et al. |
| 8,101,720 B2 | 1/2012 | Lazar et al. |
| 8,124,731 B2 | 2/2012 | Lazar et al. |
| 8,221,757 B2 | 7/2012 | Mackay |
| 8,268,972 B2 | 9/2012 | Whitfeld et al. |
| 8,318,917 B2 | 11/2012 | Taylor et al. |
| 8,337,852 B2 | 12/2012 | Mackay |
| 8,361,468 B2 | 1/2013 | Whitfeld et al. |
| 8,399,618 B2 | 3/2013 | Lazar et al. |
| 8,563,259 B2 | 10/2013 | Lambris et al. |
| 8,613,926 B2 | 12/2013 | Kjaergaard et al. |
| 8,673,305 B2 | 3/2014 | Mackay |
| 8,734,791 B2 | 5/2014 | Lazar et al. |
| 8,808,701 B2 | 8/2014 | Whitfeld et al. |
| 8,815,237 B2 | 8/2014 | Wittrup et al. |
| 8,846,045 B2 | 9/2014 | Kjaergaard et al. |
| 8,940,299 B2 | 1/2015 | Medof et al. |
| 8,952,132 B2 | 2/2015 | Georgiou et al. |
| 8,961,967 B2 | 2/2015 | Strohl et al. |
| 8,969,526 B2 | 3/2015 | Baehner et al. |
| 9,073,983 B2 | 7/2015 | Guo et al. |
| 9,180,205 B2 | 11/2015 | Zeng et al. |
| 9,458,233 B2 | 10/2016 | Guo et al. |
| 9,637,549 B2 | 5/2017 | Strohl et al. |
| 9,658,236 B2 | 5/2017 | Mcknight et al. |
| 9,683,050 B2 | 6/2017 | Zeng et al. |
| 9,790,268 B2 | 10/2017 | Pan et al. |
| 9,890,218 B2 | 2/2018 | Mimoto et al. |
| 10,053,513 B2 | 8/2018 | Mccarthy et al. |
| 10,183,999 B2 | 1/2019 | Lazar et al. |
| 10,323,097 B2 | 6/2019 | Kjaergaard et al. |
| 10,526,408 B2 | 1/2020 | Georgiou et al. |
| 10,590,206 B2 | 3/2020 | Labrijn et al. |
| 10,653,791 B2 | 5/2020 | Lonberg et al. |
| 10,774,136 B2 | 9/2020 | Gou et al. |
| 10,836,813 B2 | 11/2020 | Pan et al. |
| 10,882,916 B2 | 1/2021 | Kjaergaard et al. |
| 10,894,836 B2 | 1/2021 | Stephen et al. |
| 11,130,801 B2 | 9/2021 | Medof et al. |
| 11,142,563 B2 | 10/2021 | Igawa et al. |
| 2004/0132101 A1 | 7/2004 | Lazar et al. |
| 2011/0002931 A1 | 1/2011 | Tamburini |
| 2018/0256646 A1 | 9/2018 | Medof et al. |
| 2018/0258161 A1 | 9/2018 | Igawa et al. |
| 2018/0282425 A1 | 10/2018 | Guo et al. |
| 2018/0319877 A1 | 11/2018 | Ruike et al. |
| 2019/0134020 A1 | 5/2019 | Deng et al. |
| 2019/0225708 A1 | 7/2019 | Bosteels et al. |
| 2019/0248897 A1 | 8/2019 | Ng et al. |
| 2019/0292269 A1 | 9/2019 | Monnet |
| 2019/0300621 A1 | 10/2019 | Ravetch et al. |
| 2020/0017598 A1 | 1/2020 | Andersson et al. |
| 2020/0095310 A1 | 3/2020 | Regula et al. |
| 2020/0131253 A1 | 4/2020 | Parren et al. |
| 2020/0148779 A1 | 5/2020 | Yamniuk et al. |
| 2020/0181257 A1 | 6/2020 | Kuramochi et al. |
| 2020/0199241 A1 | 6/2020 | Igawa et al. |
| 2020/0247897 A1 | 8/2020 | Jensen et al. |
| 2020/0299400 A1 | 9/2020 | Lonberg et al. |
| 2020/0316171 A1 | 10/2020 | Pandey |
| 2020/0332022 A1 | 10/2020 | Labrijn et al. |
| 2020/0376135 A1 | 12/2020 | Boitano et al. |
| 2021/0070860 A1 | 3/2021 | Marasco et al. |
| 2021/0070875 A1 | 3/2021 | Yang et al. |
| 2021/0238300 A1 | 8/2021 | Kjaergaard et al. |
| 2021/0261648 A1 | 8/2021 | Katada et al. |
| 2021/0285964 A1 | 9/2021 | Mcknight et al. |
| 2022/0135658 A1 | 5/2022 | Neugebauer et al. |
| 2022/0356263 A1 | 11/2022 | Viswanathan et al. |

FOREIGN PATENT DOCUMENTS

| | | |
|---|---|---|
| EP | 1443961 B1 | 5/2009 |
| EP | 1706424 B1 | 7/2009 |
| EP | 1701611 B1 | 5/2011 |
| EP | 2679681 A1 | 1/2014 |
| EP | 1476469 B1 | 11/2015 |
| EP | 2345671 B1 | 11/2015 |
| EP | 2940043 A1 | 11/2015 |
| EP | 2994488 A1 | 3/2016 |
| EP | 2506871 B1 | 10/2016 |
| EP | 2552955 B1 | 5/2017 |
| EP | 2673299 B1 | 5/2017 |
| EP | 2371861 B1 | 8/2017 |
| EP | 2486141 B1 | 1/2018 |
| EP | 2691417 B1 | 8/2018 |
| EP | 2718322 B1 | 8/2018 |
| EP | 3004174 B1 | 4/2019 |
| EP | 2844289 B1 | 7/2019 |
| EP | 3141260 B1 | 8/2019 |
| EP | 3541837 A1 | 9/2019 |
| EP | 3576793 A1 | 12/2019 |
| EP | 2943507 B1 | 2/2020 |
| EP | 3608339 A1 | 2/2020 |
| EP | 3630832 A1 | 4/2020 |
| EP | 3630833 A1 | 4/2020 |
| EP | 3424953 B1 | 8/2020 |
| EP | 2698431 B1 | 9/2020 |
| EP | 3768315 A1 | 1/2021 |
| EP | 3411400 B1 | 9/2021 |
| JP | 5162587 B2 | 3/2013 |
| WO | 9500164 A1 | 1/1995 |
| WO | 2004082568 A3 | 1/2005 |
| WO | 2005050199 A1 | 6/2005 |
| WO | 2008008482 A2 | 1/2008 |
| WO | 2008022390 A1 | 2/2008 |
| WO | 2009103113 A1 | 8/2009 |
| WO | 2011100477 A2 | 8/2011 |
| WO | 2012168199 A1 | 12/2012 |
| WO | 2018065389 A1 | 4/2018 |
| WO | 2018145075 A1 | 8/2018 |
| WO | 2018183520 A1 | 10/2018 |
| WO | 2018218056 A1 | 11/2018 |
| WO | 2018224609 A1 | 12/2018 |
| WO | 2018234118 A1 | 12/2018 |
| WO | 2018217988 A9 | 5/2019 |
| WO | 2019125846 A1 | 6/2019 |
| WO | 2019183362 A1 | 9/2019 |
| WO | 2020112781 A1 | 6/2020 |
| WO | 2020182974 A1 | 9/2020 |
| WO | 2021041715 A2 | 3/2021 |
| WO | 2021146320 A1 | 7/2021 |

(56) References Cited

FOREIGN PATENT DOCUMENTS

| WO | 2021180063 A1 | 9/2021 |
|---|---|---|
| WO | 2021190770 A1 | 9/2021 |

OTHER PUBLICATIONS

International Search Report and Written Opinion for PCT/US2022/012317 dated Jun. 17, 2022 (22 pages).

Akamizu, T., et al., "Drug-induced neutropenia associated with anti-neutrophil cytoplasmic antibodies (ANCA): possible involvement of complement in granulocyte cytotoxicity", Clinical & Experimental Immunology, vol. 127, 2002, pp. 92-98 (7 pages).

Anliker-Ort, Marion, et al., "Treatment of Rare Inflammatory Kidney Diseases: Drugs Targeting the Terminal Complement Pathway", Frontiers in Immunology, vol. 11, Article 599417, Dec. 2020, pp. 1-20, DOI: 10.3389/fimmu.2020.599417 (20 pages).

Bekker, Pirow, et al., "Characterization of Pharmacologic and Pharmacokinetic Properties of CCX168, a Potent and Selective Orally Administered Complement 5a Receptor Inhibitor, Based on Preclinical Evaluation and Randomized Phase 1 Clinical Study", PLOS One, vol. 11, No. 10, Oct. 21, 2016, pp. 1-19, DOI: 10.1371/journal.pone.0164646 (19 pages).

Grayson, Peter C., et al., "Antineutrophil Cytoplasmic Antibodies, Autoimmune Neutropenia, and Vasculitis", Seminars in Arthritis and Rheumatism, vol. 42, No. 3, Dec. 2011, pp. 424-433, DOI: 10.1016/j.semarthrit.2011.02.003, Author Manuscript (16 pages).

Huang, Lili, et al., "Discovery of human antibodies against the c5aR target using phage display technology", Journal of Molecular Recognition, vol. 18, 2005, pp. 327-333, DOI: 10.1002/jmr.735 (7 pages).

Ke, Shaoying, et al., "Expression of CD88 and its effect on invasiveness of gastric carcinoma", Chinese Journal of Surgical Oncology, vol. 8, No. 3, Jun. 20, 2016 (4 pages).

Knight, A., et al., "Late-onset neutropenia after rituximab in ANCA-associated vasculitis", Scandinavian Journal of Rheumatology, vol. 45, No. 5, 2016, pp. 404-407, DOI: 10.3109/03009742.2016.1138318 (5 pages).

Kussie, Paul H., et al., "A single engineered amino acid substitution changes antibody fine specificity", The Journal of Immunology, vol. 152, No. 1, Jan. 1994, pp. 146-152, DOI: 10.4049/jimmunol.152.1.146 (8 pages).

La-Crette, Jonathan, et al., "Long-term outcomes of daily oral vs. pulsed intravenous cyclophosphamide in a non-trial setting in ANCA-associated vasculitis", Clinical Rheumatology, vol. 37, 2018, pp. 1085-1090, DOI: 10.1007/s10067-017-3944-7 (6 pages).

Mehta, Guarav, et al., "A New Approach for the Treatment of Arthritis in Mice with a Novel Conjugate of an Anti-C5aR1 Antibody and C5 Small Interfering RNA", Journal of immunology (Baltimore, Md. : 1950), vol. 194, No. 11, Jun. 1, 2015, pp. 5446-5554, DOI:10.4049/jimmunol.1403012 (22 pages).

Melis, Joost P.M., et al., "Complement in therapy and disease: Regulating the complement system with antibody-based therapeutics", Molecular Immunology, vol. 67, 2015, pp. 117-130, DOI: 10.1016/j.molimm.2015.01.028 (14 pages).

Ohlsson, Sophie, et al., "Neutrophils from ANCA-associated vasculitis patients show an increased capacity to activate the complement system via the alternative pathway after ANCA stimulation", PLOS One, vol. 14, No. 6, Jun. 19, 2019, pp. 1-16, DOI: 10.1371/journal.pone.0218272 (16 pages).

Rudikoff, et al., "Single amino acid substitution altering antigen-binding specificity", Proceedings of the National Academy of Sciences USA, Immunology, vol. 79, Mar. 1982, pp. 1979-1983 (5 pages).

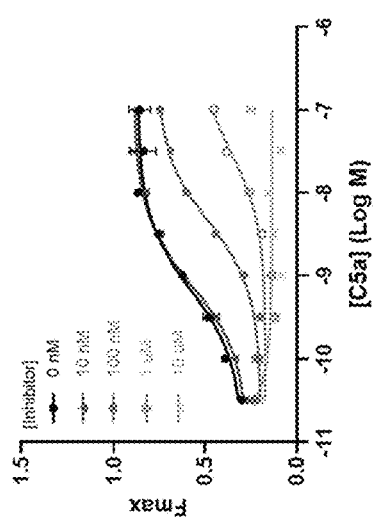
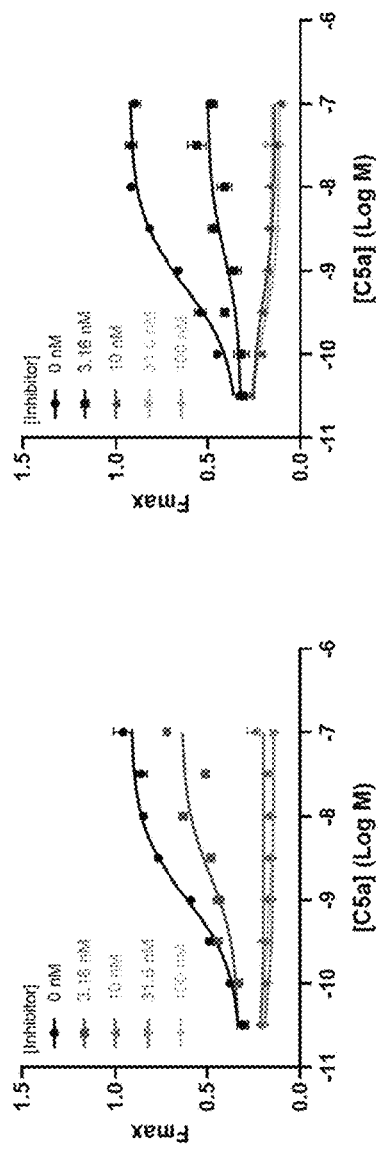
FIG. 7A    FIG. 7B    FIG. 7C

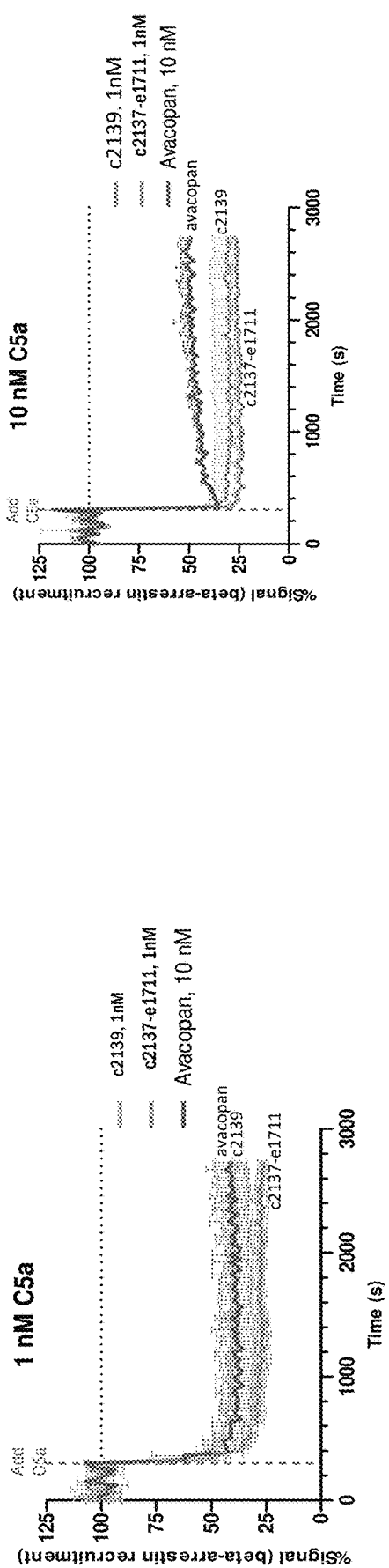
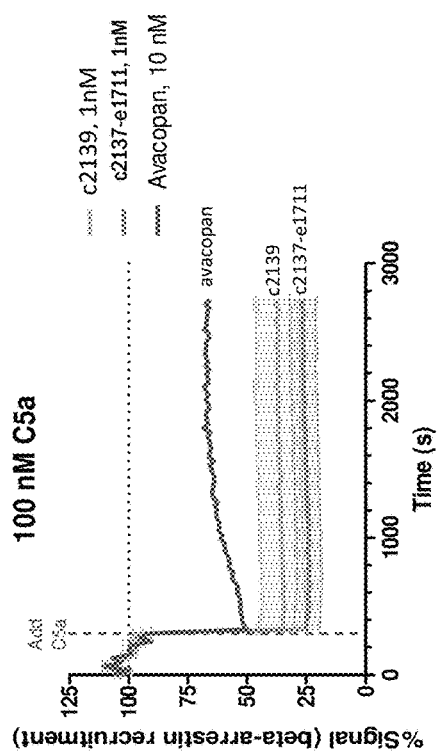
FIG. 10A
FIG. 10B
FIG. 10C

FIG. 12A, FIG. 12B, FIG. 12C, FIG. 12D

Neutropenia Study Design in Human C5aR1 mice

Dosing
- PBS (iv)
- Antibody (iv)
- Avacopan (PO)
- hC5a (iv) 0.1 mg/Kg

Blood draw timepoints: -1hr 10min, -5min, +1min, +5min, +2hr

| Group | N | Dose Route | Test Article | Dose (mg/kg) |
|---|---|---|---|---|
| 1 | 5 | IV | Vehicle (PBS) | 0 |
| 2 | 5 | IV | C2139 (PBS) | 20 |
| 3 | 5 | IV | c2137-e1711 (PBS) | 20 |
| 4 | 5 | IV | Motavizumab (PBS) | 20 |
| 5 | 5 | PO | Avacopan (Solutol/PEG400 30:70) | 30 |
| Endpoints | | | Blood collection: Pre-TA, Pre-C5a Dose, Post-C5a Dose, Post-C5a Dose up to 2 hr. FACS analysis for Markers 7AAD, CD45, CD11b, Ly6G+, mCD88, hCD88 | |

FIG. 15A

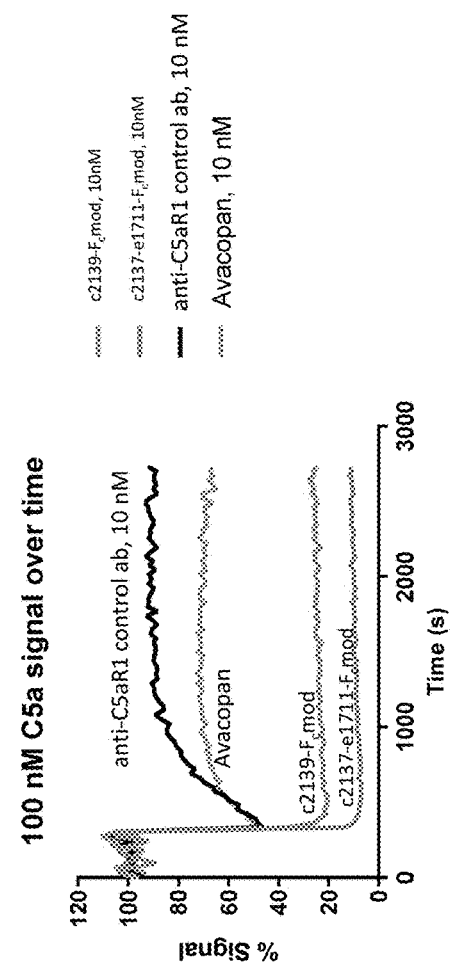
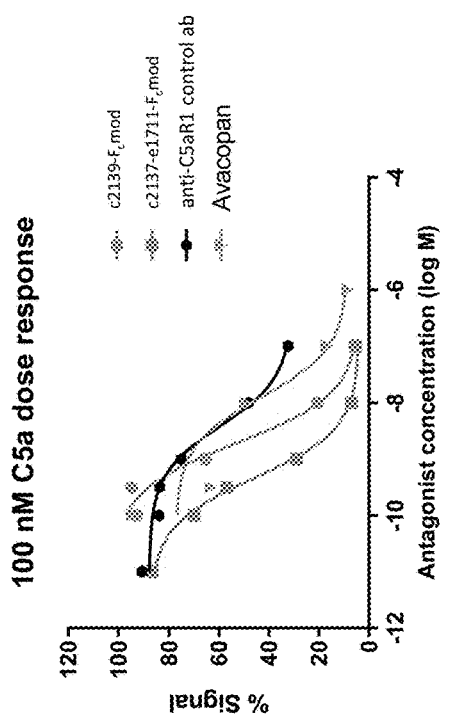
FIG. 23B
FIG. 23A

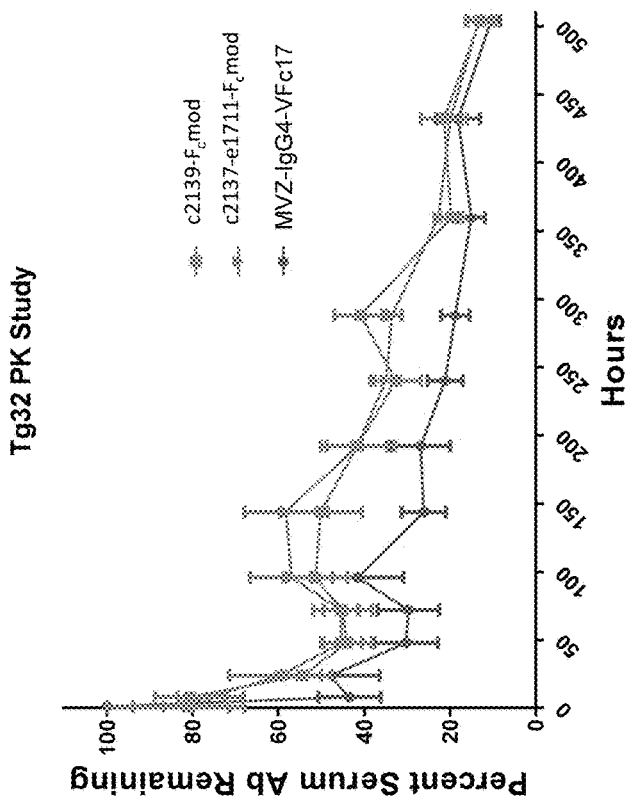
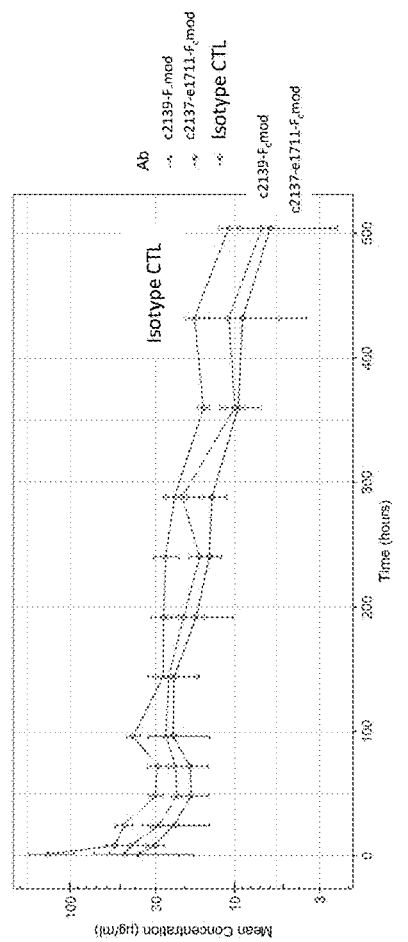
FIG. 29A
FIG. 29B

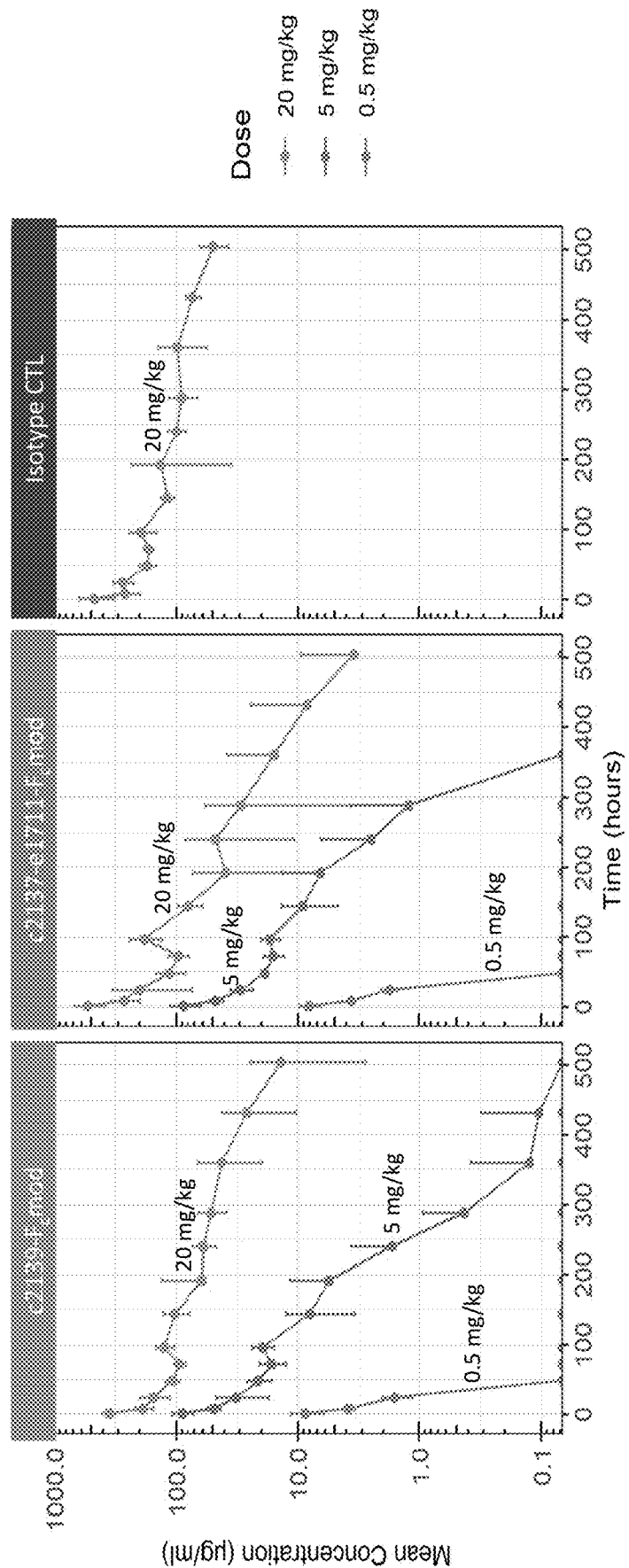

HUMANIZED COMPLEMENT 5a RECEPTOR 1 ANTIBODIES AND METHODS OF USE THEREOF

CROSS-REFERENCE TO RELATED APPLICATIONS

This application is a divisional of U.S. patent application Ser. No. 18/415,419, which is a divisional of U.S. patent application Ser. No. 17/575,420, filed Jan. 13, 2022, and issued as U.S. Pat. No. 11,912,781 on Feb. 27, 2024, which claims priority to U.S. Provisional Application No. 63/137,089, filed Jan. 13, 2021, and U.S. Provisional Application No. 63/274,748, filed Nov. 2, 2021, the disclosure of each of which is hereby incorporated by reference in its entirety.

INCORPORATION-BY-REFERENCE OF SEQUENCE LISTING

The present specification includes a Sequence Listing submitted electronically as an XML file named "SVI-003US3_SL.XML" on Aug. 12, 2024. The XML file was generated Aug. 9, 2024 and is 122,347 bytes in size. The entire contents of the Sequence Listing are herein incorporated by reference.

BACKGROUND

Disclosed are compositions and methods for the reduction of auto-immune diseases and disorders associated with complement 5a/complement 5a receptor 1 C5a/C5aR1 mediated immune inflammation. The C5a-C5aR1 axis is of particular interest for therapeutic intervention in order to block attraction of neutrophils to local sites, inhibit neutrophil activation as well as vascular destruction. The compositions and methods disclosed herein, may include a step of administering a C5aR1 antagonist, as well as methods of treating a subject in need of such a treatment.

SUMMARY OF THE INVENTION

The present disclosure provides, among other things, anti-C5aR1 antibodies with increased specificity to C5aR1 and therapeutic uses of such antibodies in effectively treating diseases or disorders associated with C5 and its receptors, such as, ANCA-vasculitis, typical hemolytic uremic syndrome, age-related macular degeneration, rheumatoid arthritis, sepsis, severe burn, antiphospholipid syndrome, asthma, lupus nephritis, Goodpasture's syndrome, and chronic obstructive pulmonary disease. As described herein, the present disclosure is, in part, based on identification of humanized anti-C5aR1 specific antibodies that bind to certain regions on Site I and/or Site II of C5aR1 and have significantly reduced cross reactivity to C5aR2 or any other G protein-coupled receptors. In particular, anti-C5aR1 antibodies of the present disclosure are characterized with high binding affinity to C5aR1 (e.g., with $K_D$ less than 50 nM) and minimal cross-reactivity with C5aR2. This is significant because C5aR1-antibodies of the present disclosure allow potent inhibition of C5aR1 signaling in the presence of high C5a concentrations. As a result, C5aR1-antibodies of the present disclosure can be used at a lower dose to achieve therapeutic effect relative to the other anti-C5aR1 antibodies or C5a-antibodies. This is demonstrated by the surprisingly high potency observed in functional assays, relative to prior-art antibodies, as described herein. Moreover, highly potent Site I C5aR1 antibodies of the present disclosure compete with each other for Site I, and highly potent Site II C5aR1 antibodies of the present disclosure compete with each other on Site II. Additionally, the present disclosure provides methods and compositions for inhibiting C5aR1 and/or C5a signaling by targeting both Site I and Site II of C5aR1. Simultaneous targeting of Site I and Site II significantly may enhance inhibitory activity. For example, combination of Site I and Site II antibodies or bispecific antibodies (e.g., biparatopic), but not two Site II or two Site II antibodies, significantly enhance activity. Inventive anti-C5aR1 antibodies of the present disclosure promise a more potent treatment of complement mediated diseases and disorders, particularly ANCA-vasculitis.

Additionally, the present disclosure provides, among other things, anti-C5aR1-antibodies comprising Fc variants that have significantly reduced ADCC, ADCP and CDC function. As described herein, the anti-C5aR1 antibodies of present disclosure comprise novel combinations of mutations that abolish binding to all FcγRI, FcγRIIa, FcγRIIb, FcγRIIIa, FcγRIIIb, and C1q, and maintain its ability to bind to FcRn.

In some embodiments, the C5aR1 antibodies provided herein have a wildtype IgG4 Fc domain. In some embodiments, the C5aR1 antibodies provided herein have a modified IgG4 Fc domain. In some embodiments, the modified C5aR1 antibodies comprise a Fab arm exchange mutation. In some embodiments, the modified C5aR1 antibodies further comprise Fc silencing mutations.

The C5a-C5aR1 axis is of particular interest for therapeutic intervention in order to block attraction of neutrophils to local sites, inhibit neutrophil activation as well as vascular destruction. The compositions and methods disclosed herein, may include a step of administering a C5aR1 antagonist, as well as methods of treating a subject in need of such a treatment.

In one aspect, this disclosure presents an antibody or antigen binding fragment thereof binding to at least one of sequences of C5aR1, comprising sequences of SEQ ID NO: 1, SEQ ID NO: 2 or SEQ ID NO: 3.

In some embodiments, an antibody or antigen binding fragment thereof binds to SEQ ID NO: 1 of C5aR1. In some embodiments, an antibody or antigen binding fragment thereof binds to SEQ ID NO: 2 of C5aR1. In some embodiments, an antibody or antigen binding fragment thereof binds to SEQ ID NO: 3 of C5aR1.

In one aspect, this disclosure presents an antibody or antigen binding fragment thereof, that binds complement component 5a receptor 1 (C5aR1) comprising a heavy chain variable region (VH), wherein the VH comprises an amino acid sequence with at least 90% identity to, the amino acid sequence of SEQ ID NO: 14.

In some embodiments, VH comprises an amino acid sequence with at least 75% identity to the amino acid sequence of SEQ ID NO: 14. In some embodiments, VH comprises an amino acid sequence with at least 78% identity to the amino acid sequence of SEQ ID NO: 14. In some embodiments, VH comprises an amino acid sequence with at least 80% identity to the amino acid sequence of SEQ ID NO: 14. In some embodiments, VH comprises an amino acid sequence with at least 82% identity to the amino acid sequence of SEQ ID NO: 14. In some embodiments, VH comprises an amino acid sequence with at least 85% identity to the amino acid sequence of SEQ ID NO: 14. In some embodiments, VH comprises an amino acid sequence with at least 88% identity to the amino acid sequence of SEQ ID NO: 14. In some embodiments, VH comprises an amino acid sequence with at least 90% identity to the amino acid sequence of SEQ ID NO: 14. In some embodiments, VH comprises an amino acid sequence with at least 90% identity to the amino acid sequence of SEQ ID NO: 14. In some embodiments, VH comprises an amino acid sequence with at least 92% identity to the amino acid sequence of SEQ ID NO: 14. In some embodiments, VH comprises an amino acid sequence with at least 93% identity to the amino acid sequence of SEQ ID NO: 14. In some embodiments, VH comprises an amino acid sequence with at least 95% identity to the amino acid sequence of SEQ ID NO: 14. In some embodiments, VH comprises an amino acid sequence with at least 97% identity to the amino acid sequence of SEQ ID NO: 14. In some embodiments, VH comprises an amino acid sequence with at least 98% identity to the amino acid sequence of SEQ ID NO: 14. In some embodiments, VH comprises an amino acid sequence with at least 99% identity to the amino acid sequence of SEQ ID NO: 14.

In one aspect, this disclosure presents an antibody or antigen binding fragment thereof, that binds complement component 5a receptor 1 (C5aR1) comprising a light chain variable region (VL), wherein the VL comprises an amino acid sequence with at least 90% identity to, the amino acid sequence of SEQ ID NO: 25.

In some embodiments, VL comprises an amino acid sequence with at least 75% identity to the amino acid sequence of SEQ ID NO: 25. In some embodiments, VL comprises an amino acid sequence with at least 78% identity to the amino acid sequence of SEQ ID NO: 25. In some embodiments, VL comprises an amino acid sequence with at least 80% identity to the amino acid sequence of SEQ ID NO: 25. In some embodiments, VL comprises an amino acid sequence with at least 82% identity to the amino acid sequence of SEQ ID NO: 25. In some embodiments, VL comprises an amino acid sequence with at least 85% identity to the amino acid sequence of SEQ ID NO: 25. In some embodiments, VL comprises an amino acid sequence with at least 88% identity to the amino acid sequence of SEQ ID NO: 25. In some embodiments, VL comprises an amino acid sequence with at least 90% identity to the amino acid sequence of SEQ ID NO: 25. In some embodiments, VL comprises an amino acid sequence with at least 90% identity to the amino acid sequence of SEQ ID NO: 25. In some embodiments, VL comprises an amino acid sequence with at least 92% identity to the amino acid sequence of SEQ ID NO: 25. In some embodiments, VL comprises an amino acid sequence with at least 93% identity to the amino acid sequence of SEQ ID NO: 25. In some embodiments, VL comprises an amino acid sequence with at least 95% identity to the amino acid sequence of SEQ ID NO: 25. In some embodiments, VL comprises an amino acid sequence with at least 97% identity to the amino acid sequence of SEQ ID NO: 25. In some embodiments, VL comprises an amino acid sequence with at least 98% identity to the amino acid sequence of SEQ ID NO: 25. In some embodiments, VL comprises an amino acid sequence with at least 99% identity to the amino acid sequence of SEQ ID NO: 25.

In one aspect, this disclosure presents an antibody or antigen binding fragment thereof, comprising a VH region, wherein the VH comprises three heavy chain complementarity determining regions (HCDRs), wherein the HCDR1, HCDR2, and HCDR3 sequences comprising amino acid sequences of SEQ ID Nos: 6, 7, and 8, respectively.

In one aspect, this disclosure presents an antibody or antigen binding fragment thereof, comprising a VL region, wherein the VL comprises three light chain complementarity determining regions (LCDRs), wherein the LCDR1, LCDR2, and LCDR3 sequences of SEQ ID Nos: 9, 10, and 11, respectively.

In one aspect, this disclosure presents an antibody or antigen binding fragment thereof, comprising a VH region, wherein the VH comprises three heavy chain complementarity determining regions (HCDRs), wherein the HCDR1, HCDR2, and HCDR3 sequences comprising amino acid sequences of SEQ ID Nos: 6, 7 and 8, respectively and a VL region, wherein the VL comprises three light chain complementarity determining regions (LCDRs), wherein the LCDR1, LCDR2, and LCDR3 sequences of SEQ ID Nos: 9, 10 and 11, respectively.

In one embodiment, the antibody or antibody or antigen binding fragment thereof according to this disclosure, further comprises an Fc region.

In one embodiment, the antibody or antibody or antigen binding fragment thereof according to this disclosure, further comprises an Fc region, wherein the Fc domain is independently selected from IgG1, IgG2, IgG3, and IgG4.

In one embodiment, the antibody or antigen binding fragment thereof binding to C5aR1 inhibits interaction of complement component 5a (C5a) with C5aR1.

In one embodiment, the antibody or antigen binding fragment thereof does not bind to C5aR2 or any other GPCR.

In one embodiment, the antibody or antigen binding fragment thereof is humanized.

In one embodiment, the VH or the VL of the antibody or the antigen binding fragment thereof, has been modified to enhance the stability of the molecule.

In one embodiment, the antibody or the antigen binding fragment thereof, comprises a serine or tyrosine mutation at position 96 of SEQ ID NO: 5 or SEQ ID NO: 25.

In one embodiment, the antibody or antigen binding fragment thereof of does not cross-react with mouse C5aR1.

In one embodiment, the antibody or antigen binding fragment thereof binds C5aR1 at an affinity of between 10 pM to 50 nM.

In some embodiments, the antibody or antigen binding fragment thereof binds C5aR1 with a dissociation constant ($K_D$) of less than about 100 nM. In some embodiments, the antibody or antigen binding fragment thereof binds C5aR1 with a dissociation constant ($K_D$) of less than about 90 nM. In some embodiments, the antibody or antigen binding fragment thereof binds C5aR1 with a dissociation constant ($K_D$) of less than about 80 nM. In some embodiments, the antibody or antigen binding fragment thereof binds C5aR1 with a dissociation constant ($K_D$) of less than about 75 nM. In some embodiments, the antibody or antigen binding fragment thereof binds C5aR1 with a dissociation constant ($K_D$) of less than about 70 nM. In some embodiments, the antibody or antigen binding fragment thereof binds C5aR1 with a dissociation constant ($K_D$) of less than about 65 nM. In some embodiments, the antibody or antigen binding fragment thereof binds C5aR1 with a dissociation constant ($K_D$) of less than about 60 nM. In some embodiments, the antibody or antigen binding fragment thereof binds C5aR1 with a dissociation constant ($K_D$) of less than about 60 nM. In some embodiments, the antibody or antigen binding fragment thereof binds C5aR1 with a dissociation constant ($K_D$) of less than about 55 nM. In some embodiments the antibody or antigen binding fragment thereof binds C5aR1 with a dissociation constant ($K_D$) of less than about 50 nM. In some embodiments, the antibody or antigen binding fragment thereof binds C5aR1 with a dissociation constant ($K_D$) of less than about 45 nM. In some embodiments, the antibody or antigen binding fragment thereof binds C5aR1 with a dissociation constant ($K_D$) of less than about 40 nM. In some embodiments, the antibody or antigen binding fragment thereof binds C5aR1 with a dissociation constant ($K_D$) of less than about 35 nM. In some embodiments, the antibody or antigen binding fragment thereof binds C5aR1 with a dissociation constant ($K_D$) of less than about 30 nM. In some embodiments, the antibody or antigen binding fragment thereof binds C5aR1 with a dissociation constant ($K_D$) of less than about 25 nM. In some embodiments, the antibody or antigen binding fragment thereof binds C5aR1 with a dissociation constant ($K_D$) of less than about 20 nM. In some embodiments the antibody or antigen binding fragment thereof binds C5aR1 with a dissociation constant ($K_D$) of less than about 15 nM. In some embodiments, the antibody or antigen binding fragment thereof binds C5aR1 with a dissociation constant ($K_D$) of less than about 10 nM. In some embodiments, the antibody or antigen binding fragment thereof binds C5aR1 with a dissociation constant ($K_D$) of less than about 8 nM. In some embodiments the antibody or antigen binding fragment thereof binds C5aR1 with a dissociation constant ($K_D$) of less than about 5 nM. In some embodiments, the antibody or antigen binding fragment thereof binds C5aR1 with a dissociation constant ($K_D$) of less than about 3 nM. In some embodiments, the antibody or antigen binding fragment thereof binds C5aR1 with a dissociation constant ($K_D$) of less than about 1 nM. In some embodiments, the antibody or antigen binding fragment thereof binds C5aR1 with a dissociation constant ($K_D$) of less than about 0.5 nM. In some embodiments, the antibody or antigen binding fragment thereof binds C5aR1 with a dissociation constant ($K_D$) of less than about 0.1 nM. In some embodiments, the antibody or antigen binding fragment thereof binds C5aR1 with a dissociation constant ($K_D$) of less than about 100 pM. In some embodiments, the antibody or antigen binding fragment thereof binds C5aR1 with a dissociation constant ($K_D$) of less than about 80 pM. In some embodiments, the antibody or antigen binding fragment thereof binds C5aR1 with a dissociation constant ($K_D$) of less than about 50 pM. In some embodiments, the antibody or antigen binding fragment thereof binds C5aR1 with a dissociation constant ($K_D$) of less than about 25 pM. In some embodiments, the antibody or antigen binding fragment thereof binds C5aR1 with a dissociation constant ($K_D$) of less than about 10 pM. In one embodiment, the antibody or antigen binding fragment thereof binds C5aR1 at an affinity of 0.16 nM or lower.

In one embodiment, the antibody or antigen binding fragment thereof binding to C5aR1 inhibits neutrophil chemotaxis.

In one embodiment, the antibody or antigen binding fragment thereof binding to C5aR1 inhibits neutrophil chemotaxis in the presence of C5a concentration of at least 0.1 nM. In one embodiment, the antibody or antigen binding fragment thereof binding to C5aR1 inhibits neutrophil chemotaxis in the presence of C5a concentration of at least 0.5 nM. In one embodiment, the antibody or antigen binding fragment thereof binding to C5aR1 inhibits neutrophil chemotaxis in the presence of C5a concentration of at least 1 nM. In one embodiment, the antibody or antigen binding fragment thereof binding to C5aR1 inhibits neutrophil chemotaxis in the presence of C5a concentration of at least 3 nM. In one embodiment, the antibody or antigen binding fragment thereof binding to C5aR1 inhibits neutrophil chemotaxis in the presence of C5a concentration of at least 5 nM. In one embodiment, the antibody or antigen binding fragment thereof binding to C5aR1 inhibits neutrophil chemotaxis in the presence of C5a concentration of at least 7 nM. In one embodiment, the antibody or antigen binding fragment thereof binding to C5aR1 inhibits neutrophil chemotaxis in the presence of C5a concentration of at least 10 nM. In one embodiment, the antibody or antigen binding fragment thereof binding to C5aR1 inhibits neutrophil chemotaxis in the presence of C5a concentration of at least 15 nM. In one embodiment, the antibody or antigen binding fragment thereof binding to C5aR1 inhibits neutrophil chemotaxis in the presence of C5a concentration of at least 20 nM. In one embodiment, the antibody or antigen binding fragment thereof binding to C5aR1 inhibits neutrophil chemotaxis in the presence of C5a concentration of at least 25 nM. In one embodiment, the antibody or antigen binding fragment thereof binding to C5aR1 inhibits neutrophil chemotaxis in the presence of C5a concentration of at least 30 nM. In one embodiment, the antibody or antigen binding fragment thereof binding to C5aR1 inhibits neutrophil chemotaxis in the presence of C5a concentration of at least 40 nM. In one embodiment, the antibody or antigen binding fragment thereof binding to C5aR1 inhibits neutrophil chemotaxis in the presence of C5a concentration of at least 50 nM. In one embodiment, the antibody or antigen binding fragment thereof binding to C5aR1 inhibits neutrophil chemotaxis in the presence of C5a concentration of at least 60 nM. In one embodiment, the antibody or antigen binding fragment thereof binding to C5aR1 inhibits neutrophil chemotaxis in the presence of C5a concentration of at least 70 nM. In one embodiment, the antibody or antigen binding fragment thereof binding to C5aR1 inhibits neutrophil chemotaxis in the presence of C5a concentration of at least 80 nM. In one embodiment, the antibody or antigen binding fragment thereof binding to C5aR1 inhibits neutrophil chemotaxis in the presence of C5a concentration of at least 90 nM. In one embodiment, the antibody or antigen binding fragment thereof binding to C5aR1 inhibits neutrophil chemotaxis in the presence of C5a concentration of at least 100 nM.

In one embodiment, the antibody or antigen binding fragment thereof inhibits C5a mediated C5aR1 Gα signaling.

In one embodiment, the antibody or antigen binding fragment thereof binding to C5aR1 inhibits calcium signaling.

In one embodiment, the antibody or antigen binding fragment thereof binding to C5aR1 inhibits CD11b expression.

In one embodiment, the antibody or antigen binding fragment thereof binding to C5aR1 inhibits neutropenia.

In one embodiment, the antibody or antigen binding fragment thereof binding to C5aR1 inhibits β-arrestin signaling.

In one embodiment, the antibody or antigen binding fragment thereof binding to C5aR1 inhibits ROS production in neutrophils.

In one embodiment, the antibody or antigen binding fragment thereof is stable at about 4° C. for up-to 1 week with one or more freeze thaw cycles. In some embodiments, the antibody or antigen binding fragment thereof is stable at about 1-15° C. for up-to 1 week with one or more freeze thaw cycles. In some embodiments, the antibody or antigen binding fragment thereof is stable at about 2-10° C. for up-to 1 week with one or more freeze thaw cycles. In some embodiments, the antibody or antigen binding fragment thereof is stable at about 3-8° C. for up-to 2 weeks with one or more freeze thaw cycles.

In one embodiment, the antibody or antigen binding fragment thereof is stable at about 4° C. for up-to 2 weeks with one or more freeze thaw cycles. In some embodiments, the antibody or antigen binding fragment thereof is stable at about 1-15° C. for up-to 2 weeks with one or more freeze thaw cycles. In some embodiments, the antibody or antigen binding fragment thereof is stable at about 2-10° C. for up-to 2 weeks with one or more freeze thaw cycles. In some embodiments, the antibody or antigen binding fragment thereof is stable at about 3-8° C. for up-to 2 weeks with one or more freeze thaw cycles.

In one embodiment, the antibody or antigen binding fragment thereof is stable at about 4° C. for up-to 4 weeks with one or more freeze thaw cycles. In some embodiments, the antibody or antigen binding fragment thereof is stable at about 1-15° C. for up-to 4 weeks with one or more freeze thaw cycles. In some embodiments, the antibody or antigen binding fragment thereof is stable at about 2-10° C. for up-to 4 weeks with one or more freeze thaw cycles. In some embodiments, the antibody or antigen binding fragment thereof is stable at about 3-8° C. for up-to 4 weeks with one or more freeze thaw cycles.

In one embodiment, the antibody or antigen binding fragment thereof is stable at about 4° C. for up-to 8 weeks with one or more freeze thaw cycles. In some embodiments, the antibody or antigen binding fragment thereof is stable at about 1-15° C. for up-to 8 weeks with one or more freeze thaw cycles. In some embodiments, the antibody or antigen binding fragment thereof is stable at about 2-10° C. for up-to 8 weeks with one or more freeze thaw cycles. In some embodiments, the antibody or antigen binding fragment thereof is stable at about 3-8° C. for up-to 8 weeks with one or more freeze thaw cycles.

In one aspect, this disclosure encompasses a nucleic acid encoding any antibody or antigen binding fragment thereof described herein.

In one aspect, this disclosure encompasses a cell comprising the nucleic acid encoding any antibody or antigen binding fragment thereof described herein.

In one aspect, this disclosure encompasses a method of making an antibody or antigen binding fragment thereof described herein, the method comprising; culturing a host cell comprising a nucleic acid encoding the antibody or antigen binding fragment thereof, an culturing the cell under conditions that allow production of the antibody or antigen binding fragment thereof.

In one aspect, this disclosure encompasses a method of treating an autoimmune diseases using an antibody or an antigen binding fragment thereof, wherein the antibody or the antigen binding fragment thereof binds complement component 5a receptor 1 (C5aR1), the antibody or antigen binding fragment thereof comprising a heavy chain variable region (VH), wherein the VH comprises an amino acid sequence with at least 90% identity to, the amino acid sequence of SEQ ID NO: 14 and/or an antibody or antigen binding fragment thereof, that binds human complement component 5a receptor 1 (C5aR1) comprising a light chain variable region (VL), wherein the VL comprises an amino acid sequence with at least 90% identity to, the amino acid sequence of SEQ ID NO: 25.

In one embodiment, the method of treating an autoimmune diseases, encompasses using an antibody or an antigen binding fragment thereof, wherein the antibody or the antigen binding fragment thereof binds human complement component 5a receptor 1 (C5aR1), the antibody or antigen binding fragment thereof comprising a heavy chain variable region (VH), wherein the VH comprises an amino acid sequence with at least 90% identity to, the amino acid sequence of SEQ ID NO: 14 and an antibody or antigen binding fragment thereof, that binds human complement component 5a receptor 1 (C5aR1) comprising a light chain variable region (VL), wherein the VL comprises an amino acid sequence with at least 90% identity to, the amino acid sequence of SEQ ID NO: 15.

In one aspect, this disclosure encompasses a method of treating an autoimmune diseases using an antibody or an antigen binding fragment thereof, wherein the antibody or the antigen binding fragment thereof binds complement component 5a receptor 1 (C5aR1), the antibody or antigen binding fragment thereof comprises three heavy chain complementarity determining regions (HCDRs), wherein the HCDR1, HCDR2, and HCDR3 sequences comprising amino acid sequences of SEQ ID Nos: 6, 7, and 8, respectively and three light chain complementarity determining regions (LCDRs), wherein the LCDR1, LCDR2, and LCDR3 sequences of SEQ ID Nos: 9, 10, and 11, respectively.

In one aspect, this disclosure encompasses a method of treating an autoimmune diseases using an antibody or an antigen binding fragment thereof, comprising SEQ ID NO: 4 or an amino acid sequence with at least 85% identity to amino acid sequence of SEQ ID NO: 4.

In some embodiments, an antibody or an antigen binding fragment thereof comprises an amino acid sequence with at least 70% identity to amino acid sequence of SEQ ID NO: 4. In some embodiments, an antibody or an antigen binding fragment thereof comprises an amino acid sequence with at least 75% identity to amino acid sequence of SEQ ID NO: 4. In some embodiments, an antibody or an antigen binding fragment thereof comprises an amino acid sequence with at least 78% identity to amino acid sequence of SEQ ID NO: 4. In some embodiments, an antibody or an antigen binding fragment thereof comprises an amino acid sequence with at least 80% identity to amino acid sequence of SEQ ID NO: 4. In some embodiments, an antibody or an antigen binding fragment thereof comprises an amino acid sequence with at least 82% identity to amino acid sequence of SEQ ID NO: 4. In some embodiments, an antibody or an antigen binding fragment thereof comprises an amino acid sequence with at least 85% identity to amino acid sequence of SEQ ID NO: 4. In some embodiments, an antibody or an antigen binding fragment thereof comprises an amino acid sequence with at least 87% identity to amino acid sequence of SEQ ID NO: 4. In some embodiments, an antibody or an antigen binding fragment thereof comprises an amino acid sequence with at least 90% identity to amino acid sequence of SEQ ID NO: 4. In some embodiments, an antibody or an antigen binding fragment thereof comprises an amino acid sequence with at least 93% identity to amino acid sequence of SEQ ID NO: 4. In some embodiments, an antibody or an antigen binding fragment thereof comprises an amino acid sequence with at least 95% identity to amino acid sequence of SEQ ID NO: 4. In some embodiments, an antibody or an antigen binding fragment thereof comprises an amino acid sequence with at least 97% identity to amino acid sequence of SEQ ID NO: 4. In some embodiments, an antibody or an antigen binding fragment thereof comprises an amino acid sequence with at least 98% identity to amino acid sequence of SEQ ID NO: 4. In some embodiments, an antibody or an antigen binding fragment thereof comprises an amino acid sequence with at least 99% identity to amino acid sequence of SEQ ID NO: 4.

In one aspect, this disclosure encompasses a method of treating an autoimmune diseases using an antibody or an antigen binding fragment thereof, comprising SEQ ID NO:

5 or an amino acid sequence with at least 85% identity to amino acid sequence of SEQ ID NO: 5.

In some embodiments, an antibody or an antigen binding fragment thereof comprises an amino acid sequence with at least 70% identity to amino acid sequence of SEQ ID NO: 5. In some embodiments, an antibody or an antigen binding fragment thereof comprises an amino acid sequence with at least 75% identity to amino acid sequence of SEQ ID NO: 5. In some embodiments, an antibody or an antigen binding fragment thereof comprises an amino acid sequence with at least 78% identity to amino acid sequence of SEQ ID NO: 5. In some embodiments, an antibody or an antigen binding fragment thereof comprises an amino acid sequence with at least 80% identity to amino acid sequence of SEQ ID NO: 5. In some embodiments, an antibody or an antigen binding fragment thereof comprises an amino acid sequence with at least 82% identity to amino acid sequence of SEQ ID NO: 5. In some embodiments, an antibody or an antigen binding fragment thereof comprises an amino acid sequence with at least 85% identity to amino acid sequence of SEQ ID NO: 5. In some embodiments, an antibody or an antigen binding fragment thereof comprises an amino acid sequence with at least 87% identity to amino acid sequence of SEQ ID NO: 5. In some embodiments, an antibody or an antigen binding fragment thereof comprises an amino acid sequence with at least 90% identity to amino acid sequence of SEQ ID NO: 5. In some embodiments, an antibody or an antigen binding fragment thereof comprises an amino acid sequence with at least 93% identity to amino acid sequence of SEQ ID NO: 5. In some embodiments, an antibody or an antigen binding fragment thereof comprises an amino acid sequence with at least 95% identity to amino acid sequence of SEQ ID NO: 5. In some embodiments, an antibody or an antigen binding fragment thereof comprises an amino acid sequence with at least 97% identity to amino acid sequence of SEQ ID NO: 5. In some embodiments, an antibody or an antigen binding fragment thereof comprises an amino acid sequence with at least 98% identity to amino acid sequence of SEQ ID NO: 5. In some embodiments, an antibody or an antigen binding fragment thereof comprises an amino acid sequence with at least 99% identity to amino acid sequence of SEQ ID NO: 4.

In one embodiment, this disclosure encompasses a disease caused by neutropenia caused using an antibody or an antigen binding fragment thereof described herein.

In one embodiment, the neutropenia is caused by high levels of C5a.

In one embodiment, the disease is ANCA vasculitis or lupus.

In one embodiment, the disorder is rheumatoid arthritis.

In one embodiment, the disorder is a kidney disorder.

In one aspect, this disclosure encompasses a method of inhibition of C5a signaling using an monoclonal antibody which binds to C5aR1, comprising a heavy chain variable region (VH), wherein the VH comprises an amino acid sequence with at least 90% identity to, the amino acid sequence of SEQ ID NO: 14 and a light chain variable region (VL), wherein the VL comprises an amino acid sequence with at least 90% identity to, the amino acid sequence of SEQ ID NO: 25.

In one aspect, this disclosure encompasses a biparatopic antibody or antigen binding fragment thereof, comprising two pairs of antigen binding domains, wherein a first antigen binding domain comprises a VH1 and a VL1, wherein the VH1 and VL1 bind C5aR1 at SEQ ID NO: 3 and wherein a second antigen binding domain comprises a VH2 and VL2, wherein the VH2 and VL2 bind C5aR1 at SEQ ID NO: 1 or SEQ ID NO: 2.

In one aspect, this disclosure encompasses a biparatopic antibody or antigen binding fragment thereof, comprising two pairs of antigen binding domains, wherein an antigen binding domain comprises a VH1 and a VL1, wherein the VH1 and VL1 bind C5aR1 at SEQ ID NO: 1 or SEQ ID NO: 2 and wherein a second antigen binding domain comprises a VH2 and a VL2, wherein the VH2 and VL2 bind C5aR1 at SEQ ID NO: 3.

In one embodiment, the biparatopic antibody or antigen binding fragment thereof comprises a VH1 comprising SEQ ID NO: 14 or at least 90% identical to of SEQ ID NO: 14.

In one embodiment, the biparatopic antibody or antigen binding fragment thereof comprises a VL, wherein the VL1 comprises an amino acid sequence of SEQ ID NO: 15, or is at least 90% identical to amino acid sequence of SEQ ID NO: 15. In some embodiments, the VL1 comprises an amino acid sequence with at least 75% identity to the amino acid sequence of SEQ ID NO: 15. In some embodiments, the VL1 comprises an amino acid sequence with at least 78% identity to the amino acid sequence of SEQ ID NO: 15. In some embodiments, the VL1 comprises an amino acid sequence with at least 80% identity to the amino acid sequence of SEQ ID NO: 15. In some embodiments, the VL1 comprises an amino acid sequence with at least 82% identity to the amino acid sequence of SEQ ID NO: 15. In some embodiments, the VL1 comprises an amino acid sequence with at least 84% identity to the amino acid sequence of SEQ ID NO: 15. In some embodiments, the VL1 comprises an amino acid sequence with at least 85% identity to the amino acid sequence of SEQ ID NO: 15. In some embodiments, the VL1 comprises an amino acid sequence with at least 86% identity to the amino acid sequence of SEQ ID NO: 15. In some embodiments, the VL1 comprises an amino acid sequence with at least 88% identity to the amino acid sequence of SEQ ID NO: 15. In some embodiments, the VL1 comprises an amino acid sequence with at least 90% identity to the amino acid sequence of SEQ ID NO: 15. In some embodiments, the VL1 comprises an amino acid sequence with at least 92% identity to the amino acid sequence of SEQ ID NO: 15. In some embodiments, the VL1 comprises an amino acid sequence with at least 94% identity to the amino acid sequence of SEQ ID NO: 15. In some embodiments, the VL1 comprises an amino acid sequence with at least 95% identity to the amino acid sequence of SEQ ID NO: 15. In some embodiments, the VL1 comprises an amino acid sequence with at least 96% identity to the amino acid sequence of SEQ ID NO: 15. In some embodiments, the VL1 comprises an amino acid sequence with at least 97% identity to the amino acid sequence of SEQ ID NO: 15. In some embodiments, the VL1 comprises an amino acid sequence with at least 98% identity to the amino acid sequence of SEQ ID NO: 15. In some embodiments, the VL1 comprises an amino acid sequence with at least 99% identity to the amino acid sequence of SEQ ID NO: 15.

In one embodiment, the biparatopic antibody or antigen binding fragment thereof comprises a VH2, wherein the VH2 comprises an amino acid sequence of SEQ ID NO: 16, or is at least 90% identical to of SEQ ID NO: 16. In some embodiments, the VH2 comprises an amino acid sequence with at least 75% identity to the amino acid sequence of SEQ ID NO: 16. In some embodiments, the VH2 comprises an amino acid sequence with at least 78% identity to the amino acid sequence of SEQ ID NO: 16. In some embodiments, the VH2 comprises an amino acid sequence with at least 80% identity to the amino acid sequence of SEQ ID NO: 16. In some embodiments, the VH2 comprises an amino acid sequence with at least 82% identity to the amino acid sequence of SEQ ID NO: 16. In some embodiments, the VH2 comprises an amino acid sequence with at least 85% identity to the amino acid sequence of SEQ ID NO: 16. In some embodiments, the VH2 comprises an amino acid sequence with at least 86% identity to the amino acid sequence of SEQ ID NO: 16. In some embodiments, the VH2 comprises an amino acid sequence with at least 88% identity to the amino acid sequence of SEQ ID NO: 16. In some embodiments, the VH2 comprises an amino acid sequence with at least 90% identity to the amino acid sequence of SEQ ID NO: 16. In some embodiments, the VH2 comprises an amino acid sequence with at least 92% identity to the amino acid sequence of SEQ ID NO: 16. In some embodiments, the VH2 comprises an amino acid sequence with at least 94% identity to the amino acid sequence of SEQ ID NO: 16. In some embodiments, the VH2 comprises an amino acid sequence with at least 95% identity to the amino acid sequence of SEQ ID NO: 16. In some embodiments, the VH2 comprises an amino acid sequence with at least 96% identity to the amino acid sequence of SEQ ID NO: 16. In some embodiments, the VH2 comprises an amino acid sequence with at least 97% identity to the amino acid sequence of SEQ ID NO: 16. In some embodiments, the VH2 comprises an amino acid sequence with at least 98% identity to the amino acid sequence of SEQ ID NO: 16. In some embodiments, the VH2 comprises an amino acid sequence with at least 99% identity to the amino acid sequence of SEQ ID NO: 16.

In one embodiment, the biparatopic antibody or antigen binding fragment thereof comprises a VL2, wherein the, VL2 comprises an amino acid sequence of SEQ ID NO: 17, or is at least 90% identical to the amino acid sequence of SEQ ID NO: 17. In some embodiments, the VL2 comprises an amino acid sequence with at least 75% identity to the amino acid sequence of SEQ ID NO: 17. In some embodiments, the VL2 comprises an amino acid sequence with at least 78% identity to the amino acid sequence of SEQ ID NO: 17. In some embodiments, the VL2 comprises an amino acid sequence with at least 80% identity to the amino acid sequence of SEQ ID NO: 17. In some embodiments, the VL2 comprises an amino acid sequence with at least 82% identity to the amino acid sequence of SEQ ID NO: 17. In some embodiments, the VL2 comprises an amino acid sequence with at least 84% identity to the amino acid sequence of SEQ ID NO: 17. In some embodiments, the VL2 comprises an amino acid sequence with at least 85% identity to the amino acid sequence of SEQ ID NO: 17. In some embodiments, the VL2 comprises an amino acid sequence with at least 86% identity to the amino acid sequence of SEQ ID NO: 17. In some embodiments, the VL2 comprises an amino acid sequence with at least 88% identity to the amino acid sequence of SEQ ID NO: 17. In some embodiments, the VL2 comprises an amino acid sequence with at least 90% identity to the amino acid sequence of SEQ ID NO: 17. In some embodiments, the VL2 comprises an amino acid sequence with at least 92% identity to the amino acid sequence of SEQ ID NO: 17. In some embodiments, the VL2 comprises an amino acid sequence with at least 94% identity to the amino acid sequence of SEQ ID NO: 17. In some embodiments, the VL2 comprises an amino acid sequence with at least 95% identity to the amino acid sequence of SEQ ID NO: 17. In some embodiments, the VL2 comprises an amino acid sequence with at least 96% identity to the amino acid sequence of SEQ ID NO: 17. In some embodiments, the VL2 comprises an amino acid sequence with at least 97% identity to the amino acid sequence of SEQ ID NO: 17. In some embodiments, the VH2 comprises an amino acid sequence with at least 98% identity to the amino acid sequence of SEQ ID NO: 17. In some embodiments, the VL2 comprises an amino acid sequence with at least 99% identity to the amino acid sequence of SEQ ID NO: 17.

In one aspect, this disclosure encompasses a biparatopic antibody or antigen binding fragment thereof, binding to SEQ ID NO: 3, comprises a heavy chain of SEQ ID NO: 12, or at least 85% identical to the amino acid sequence of SEQ ID NO: 12. In some embodiments, the heavy chain comprises an amino acid sequence with at least 75% identity to the amino acid sequence of SEQ ID NO: 12. In some embodiments, the heavy chain comprises an amino acid sequence with at least 78% identity to the amino acid sequence of SEQ ID NO: 12. In some embodiments, the heavy chain comprises an amino acid sequence with at least 80% identity to the amino acid sequence of SEQ ID NO: 12. In some embodiments, the heavy chain comprises an amino acid sequence with at least 82% identity to the amino acid sequence of SEQ ID NO: 12. In some embodiments, the heavy chain comprises an amino acid sequence with at least 84% identity to the amino acid sequence of SEQ ID NO: 12. In some embodiments, the heavy chain comprises an amino acid sequence with at least 85% identity to the amino acid sequence of SEQ ID NO: 12. In some embodiments, the heavy chain comprises an amino acid sequence with at least 86% identity to the amino acid sequence of SEQ ID NO: 12. In some embodiments, the heavy chain comprises an amino acid sequence with at least 88% identity to the amino acid sequence of SEQ ID NO: 12. In some embodiments, the heavy chain comprises an amino acid sequence with at least 90% identity to the amino acid sequence of SEQ ID NO: 12. In some embodiments, the heavy chain comprises an amino acid sequence with at least 92% identity to the amino acid sequence of SEQ ID NO: 12. In some embodiments, the heavy chain comprises an amino acid sequence with at least 94% identity to the amino acid sequence of SEQ ID NO: 12. In some embodiments, the heavy chain comprises an amino acid sequence with at least 95% identity to the amino acid sequence of SEQ ID NO: 12. In some embodiments, the heavy chain comprises an amino acid sequence with at least 96% identity to the amino acid sequence of SEQ ID NO: 12. In some embodiments, the heavy chain comprises an amino acid sequence with at least 98% identity to the amino acid sequence of SEQ ID NO: 12. In some embodiments, the heavy chain comprises an amino acid sequence with at least 99% identity to the amino acid sequence of SEQ ID NO: 12.

In one aspect, this disclosure encompasses a biparatopic antibody or antigen binding fragment thereof, binding to SEQ ID NO: 3, comprises a light chain of SEQ ID NO: 13, or at least 85% identical to the amino acid sequence of SEQ ID NO: 13. In some embodiments, the light chain comprises an amino acid sequence with at least 75% identity to the amino acid sequence of SEQ ID NO: 13. In some embodiments, the light chain comprises an amino acid sequence with at least 78% identity to the amino acid sequence of SEQ ID NO: 13. In some embodiments, the light chain comprises an amino acid sequence with at least 80% identity to the amino acid sequence of SEQ ID NO: 13. In some embodiments, the light chain comprises an amino acid sequence with at least 82% identity to the amino acid sequence of SEQ ID NO: 13. In some embodiments, the light chain comprises an amino acid sequence with at least 84% identity to the amino acid sequence of SEQ ID NO: 13. In some embodiments, the light chain comprises an amino acid sequence with at least 85% identity to the amino acid sequence of SEQ ID NO: 13. In some embodiments, the light chain comprises an amino acid sequence with at least 86% identity to the amino acid sequence of SEQ ID NO: 13. In some embodiments, the light chain comprises an amino acid sequence with at least 88% identity to the amino acid sequence of SEQ ID NO: 13. In some embodiments, the light chain comprises an amino acid sequence with at least 90% identity to the amino acid sequence of SEQ ID NO: 13. In some embodiments, the light chain comprises an amino acid sequence with at least 92% identity to the amino acid sequence of SEQ ID NO: 13. In some embodiments, the light chain comprises an amino acid sequence with at least 94% identity to the amino acid sequence of SEQ ID NO: 13. In some embodiments, the light chain comprises an amino acid sequence with at least 95% identity to the amino acid sequence of SEQ ID NO: 13. In some embodiments, the light chain comprises an amino acid sequence with at least 96% identity to the amino acid sequence of SEQ ID NO: 13. In some embodiments, the light chain comprises an amino acid sequence with at least 98% identity to the amino acid sequence of SEQ ID NO: 13. In some embodiments, the light chain comprises an amino acid sequence with at least 99% identity to the amino acid sequence of SEQ ID NO: 13.

In one aspect, this disclosure encompasses a biparatopic antibody or antigen binding fragment thereof, comprising a heavy chain of SEQ ID NO: 12, or at least 85% identical to the amino acid sequence of SEQ ID NO: 12 and a light chain comprising SEQ ID NO: 13, or at least 85% identical to the amino acid sequence of SEQ ID NO: 13. In one aspect, this disclosure encompasses a biparatopic antibody or antigen binding fragment thereof, comprising a heavy chain of SEQ ID NO: 12, or at least 90% identical to the amino acid sequence of SEQ ID NO: 12 and a light chain comprising SEQ ID NO: 13, or at least 90% identical to the amino acid sequence of SEQ ID NO: 13. In one aspect, this disclosure encompasses a biparatopic antibody or antigen binding fragment thereof, comprising a heavy chain of SEQ ID NO: 12, or at least 92% identical to the amino acid sequence of SEQ ID NO: 12 and a light chain comprising SEQ ID NO: 13, or at least 92% identical to the amino acid sequence of SEQ ID NO: 13. In one aspect, this disclosure encompasses a biparatopic antibody or antigen binding fragment thereof, comprising a heavy chain of SEQ ID NO: 12, or at least 95% identical to the amino acid sequence of SEQ ID NO: 12 and a light chain comprising SEQ ID NO: 13, or at least 95% identical to the amino acid sequence of SEQ ID NO: 13. In one aspect, this disclosure encompasses a biparatopic antibody or antigen binding fragment thereof, comprising a heavy chain of SEQ ID NO: 12, or at least 99% identical to the amino acid sequence of SEQ ID NO: 12 and a light chain comprising SEQ ID NO: 13, or at least 99% identical to the amino acid sequence of SEQ ID NO: 13.

In one aspect, the present invention provides, among other things, an anti-C5aR1 biparatopic antibody comprising a heavy chain of SEQ ID NO: 71 and a light chain of SEQ ID NO: 72. In some embodiments, an anti-C5aR1 biparatopic antibody comprises a heavy chain that is at least 85% identical to SEQ ID NO: 71. In some embodiments, an anti-C5aR1 biparatopic antibody comprises a heavy chain that is at least 90% identical to SEQ ID NO: 71. In some embodiments, an anti-C5aR1 biparatopic antibody comprises a heavy chain that is at least 92% identical to SEQ ID NO: 71. In some embodiments, an anti-C5aR1 biparatopic antibody comprises a heavy chain that is at least 95% identical to SEQ ID NO: 71. In some embodiments, an anti-C5aR1 biparatopic antibody comprises a heavy chain that is at least 97% identical to SEQ ID NO: 71. In some embodiments, an anti-C5aR1 biparatopic antibody comprises a heavy chain that is at least 98% identical to SEQ ID NO: 71. In some embodiments, an anti-C5aR1 biparatopic antibody comprises a heavy chain that is at least 99% identical to SEQ ID NO: 71. In some embodiments, an anti-C5aR1 biparatopic antibody comprises a light chain that is at least 85% identical to SEQ ID NO: 72. In some embodiments, an anti-C5aR1 biparatopic antibody comprises a light chain that is at least 90% identical to SEQ ID NO: 72. In some embodiments, an anti-C5aR1 biparatopic antibody comprises a light chain that is at least 92% identical to SEQ ID NO: 72. In some embodiments, an anti-C5aR1 biparatopic antibody comprises a light chain that is at least 95% identical to SEQ ID NO: 72. In some embodiments, an anti-C5aR1 biparatopic antibody comprises a light chain that is at least 97% identical to SEQ ID NO: 72. In some embodiments, an anti-C5aR1 biparatopic antibody comprises a light chain that is at least 98% identical to SEQ ID NO: 72. In some embodiments, an anti-C5aR1 biparatopic antibody comprises a light chain that is at least 99% identical to SEQ ID NO: 72.

In one aspect, the present invention provides, among other things, an anti-C5aR1 antibody comprising a heavy chain of SEQ ID NO: 69 and a light chain of SEQ ID NO: 70. In some embodiments, an anti-C5aR1 antibody comprises a heavy chain at is at least 85% identical to SEQ ID NO: 69. In some embodiments, an anti-C5aR1 antibody comprises a heavy chain at is at least 90% identical to SEQ ID NO: 69. In some embodiments, an anti-C5aR1 antibody comprises a heavy chain at is at least 92% identical to SEQ ID NO: 69. In some embodiments, an anti-C5aR1 antibody comprises a heavy chain at is at least 85% identical to SEQ ID NO: 69. In some embodiments, an anti-C5aR1 antibody comprises a heavy chain at is at least 95% identical to SEQ ID NO: 69. In some embodiments, an anti-C5aR1 antibody comprises a heavy chain at is at least 97% identical to SEQ ID NO: 69. In some embodiments, an anti-C5aR1 antibody comprises a heavy chain at is at least 98% identical to SEQ ID NO: 69. In some embodiments, an anti-C5aR1 antibody comprises a heavy chain at is at least 99% identical to SEQ ID NO: 69. In some embodiments, an anti-C5aR1 antibody comprises a light chain at is at least 85% identical to SEQ ID NO: 70. In some embodiments, an anti-C5aR1 antibody comprises a light chain at is at least 90% identical to SEQ ID NO: 70. In some embodiments, an anti-C5aR1 antibody comprises a light chain at is at least 92% identical to SEQ ID NO: 70. In some embodiments, an anti-C5aR1 antibody comprises a light chain at is at least 85% identical to SEQ ID NO: 70. In some embodiments, an anti-C5aR1 antibody comprises a light chain at is at least 95% identical to SEQ ID NO: 70. In some embodiments, an anti-C5aR1 antibody comprises a light chain at is at least 97% identical to SEQ ID NO: 70. In some embodiments, an anti-C5aR1 antibody comprises a light chain at is at least 98% identical to SEQ ID NO: 70. In some embodiments, an anti-C5aR1 antibody comprises a light chain at is at least 99% identical to SEQ ID NO: 70.

In one aspect, this disclosure encompass a biparatopic antibody or antigen binding fragment thereof, wherein the heavy chain comprises the VH1 linked to an Fc domain.

In one embodiment, the Fc domain of the biparatopic antibody or antigen binding fragment thereof is further linked to a scFv comprising a VH2 comprising an amino acid sequence of SEQ ID NO: 16, or an amino acid sequence at least 90% identical to the amino acid sequence of SEQ ID NO: 16 and/or a VL2 comprising an amino acid sequence of SEQ ID NO: 17, or an amino acid sequence at least 90% identical to the amino acid sequence of SEQ ID NO: 17.

In one embodiment, the Fc domain is independently selected from IgG1, IgG2, IgG3, and IgG4.

In one embodiment, the scFv is linked to the Fc domain, via a linker.

In one embodiment, the linker comprises at-least 5 amino acids comprising an amino acid sequence with any of SEQ ID NOs: 26-37. In one embodiment, the linker comprises at-least 3 amino acids comprising an amino acid sequence with any of SEQ ID NOs: 26-37. In one embodiment, the linker comprises at-least 4 amino acids comprising an amino acid sequence with any of SEQ ID NOs: 26-37. In one embodiment, the linker comprises at-least 6 amino acids comprising an amino acid sequence with any of SEQ ID NOs: 26-37. In one embodiment, the linker comprises at-least 7 amino acids comprising an amino acid sequence with any of SEQ ID NOs: 26-37.

In one embodiment, the VH2 and VL2 of the biparatopic antibody comprising SEQ ID NO: 16 and SEQ ID NO: 17 are linked to each other via a linker.

In one embodiment, the linker comprises 1-10 repeats of SEQ ID NO: 31.

In one embodiment, the VH2 and VL2 of the biparatopic antibody comprising SEQ ID NO: 16 and SEQ ID NO: 17, or an amino acid sequence 90% identical to SEQ ID NO: 16 and SEQ ID NO: 17, further comprise one or more mutations to improve thermal stability of the biparatopic antibody.

In one embodiment, the biparatopic antibody the mutation to improve thermal stability of the biparatopic antibody comprises incorporation of Cysteine at position 559 of SEQ ID NO: 12 and at position 630 of SEQ ID NO: 12.

In one embodiment, the biparatopic antibody or antigen binding fragment thereof binding to C5aR1 inhibits interaction of complement component 5a (C5a) with human C5aR1.

In one embodiment, the biparatopic antibody or antigen binding fragment thereof does not bind to C5aR2.

In one embodiment, the biparatopic antibody is humanized.

In one embodiment, the biparatopic antibody does not cross-react with mouse C5aR1.

In one embodiment, the biparatopic antibody is stable at 4° C. for up-to 2 weeks with one freeze thaw cycle. In some embodiments, the biparatopic antibody or antigen binding fragment thereof is stable at about 1-15° C. for up-to 2 weeks with one or more freeze thaw cycles. In some embodiments, the biparatopic antibody or antigen binding fragment thereof is stable at about 2-10° C. for up-to 2 weeks with one or more freeze thaw cycles. In some embodiments, the biparatopic antibody or antigen binding fragment thereof is stable at about 3-8° C. for up-to 2 weeks with one or more freeze thaw cycles.

In one embodiment, the biparatopic antibody binding to C5aR1 inhibits neutrophil chemotaxis.

In one embodiment, the biparatopic antibody binding to C5aR1 inhibits neutrophil chemotaxis in the presence of high C5a concentration.

In one embodiment, the biparatopic antibody binding to C5aR1 inhibits neutrophil chemotaxis in the presence of C5a concentration of at least 10 nM.

In one embodiment, the biparatopic antibody binding to C5aR1 inhibits C5a mediated C5aR1 Gα signaling.

In one embodiment, the biparatopic antibody binding to C5aR1 inhibits β-arrestin signaling.

In one embodiment, the biparatopic antibody binding to C5aR1 inhibits ROS production in neutrophils.

In one embodiment, the biparatopic antibody binding to C5aR1 inhibits calcium signaling.

In one embodiment, the biparatopic antibody binding to C5aR1 inhibits CD11b expression.

In one embodiment, the biparatopic antibody binding to C5aR1 inhibits neutropenia In one aspect, this disclosure encompasses a nucleic acid encoding the biparatopic antibody described herein.

In one aspect, this disclosure encompasses a cell comprising the nucleic acid encoding the biparatopic antibody described herein.

In one aspect, this disclosure encompasses a method of making a biparatopic antibody described herein, the method comprising culturing a host cell comprising a nucleic acid encoding the antibody or antigen binding fragment thereof, an culturing the cell under conditions that allow production of the antibody or antigen binding fragment thereof.

In one aspect, this disclosure encompasses a method of treating an autoimmune diseases using a biparatopic antibody wherein the antibody binds human complement component 5a receptor 1 (C5aR1), the comprising: a first VH and a first VL, VH1 and VL1, wherein the VH1 comprises SEQ ID NO: 14 or an amino acid sequence with at least 90% identity to SEQ ID NO: 14 and wherein the VL1 comprises SEQ ID NO: 15 or an amino acid sequence with at least with at least 90% identity to SEQ ID NO: 15 and a second VH and a second VL, VH2 and VL2, wherein the VH2 comprises SEQ ID NO: 16 or an amino acid sequence with at least with at least 90% identity to SEQ ID NO: 16 and VL2 comprises SEQ ID NO: 17 or an amino acid sequence with at least with at least 90% identity to SEQ ID NO: 17.

In one embodiment, this disclosure encompasses a method of treating an autoimmune disease caused wherein the autoimmune disease is caused by neutropenia using an antibody or an antigen binding fragment thereof described herein.

In one embodiment, the neutropenia is caused by high levels of C5a.

In one embodiment, the disease is ANCA vasculitis or lupus.

In one embodiment, the disorder is rheumatoid arthritis.

In one embodiment, the disorder is a kidney disorder.

In one embodiment, the disorder is stroke.

In one embodiment, the monospecific or biparatopic C5aR1 antibody of any of the preceding embodiments, wherein the antibody comprises a modified IgG1, IgG4 or IgG2 constant domains.

In one embodiment, the antibody the C5aR1 comprises a modified IgG4 Fc domain.

In one embodiment, the modified IgG4 Fc domain comprises substitutions at positions F234, L235 and/or D265.

In one embodiment, the IgG4 Fc substitution at position F234 is a hydrophobic amino acid selected from Alanine, Valine, Leucine, Isoleucine, phenylalanine, or tryptophan.

In one embodiment, the IgG4 Fc substitution at position F234 is a valine.

In one embodiment, the IgG4 Fc substitution at position L235 is an acidic amino acid.

In one embodiment, the IgG4 Fc substitution at position L235 is an acidic amino acid selected from glutamate or aspartate.

In one embodiment, the IgG4 Fc substitution at position L235 is aspartate.

In one embodiment, the IgG4 Fc substitution at position D265 is a non-polar amino acid.

In one embodiment, the IgG4 Fc substitution at position D265 is a non-polar amino acid selected from alanine, cysteine, glycine, isoleucine, leucine, methionine, and valine.

In one embodiment, the IgG4 Fc substitution at position D265 is glycine.

In one embodiment, the antibody of any of the previous embodiments further comprises a substitution at S228.

In one embodiment, the substitution at S228 is a proline.

In one embodiment, the monospecific or biparatopic C5aR1 antibody of any of the preceding embodiments, wherein the antibody comprises a modified IgG4 constant domain comprising combination of F234V, L235E and D265G substitutions.

In one embodiment, the present disclosure provides a method of reducing or preventing antibody dependent cytotoxicity, antibody dependent phagocytosis and/or Complement Dependent Cytotoxicity, using a monospecific or biparatopic C5aR1 antibody of any of the previous embodiments.

In one aspect, the present disclosure encompasses an antibody or antigen binding fragment thereof, that binds complement component 5a receptor 1 (C5aR1) comprising: a heavy chain variable region (VH) of SEQ ID NO: 14; a light chain variable region (VL) of SEQ ID NO: 25; and a modified Fc domain comprising substitutions F234V, L235E, and D265G.

In one aspect, the present disclosure encompasses an antibody or antigen binding fragment thereof, that binds complement component 5a receptor 1 (C5aR1) comprising: a heavy chain variable region (VH) comprising HCDR1 of SEQ ID NO: 6, a HCDR2 of SEQ ID NO: 7, and a HCDR3 of SEQ ID NO: 8; a light chain variable region (VL) comprising LCDR1 of SEQ ID NO: 9, LCDR2 of SEQ ID NO: 10, and LCDR3 of SEQ ID NO: 11; and a modified Fc domain comprising substitutions F234V, L235E, and D265G.

In one aspect, the present disclosure encompasses an antibody or antigen binding fragment thereof, that binds complement component 5a receptor 1 (C5aR1) comprising a heavy chain of SEQ ID NO: 69 and a light chain of SEQ ID NO: 70.

In one aspect, the present disclosure encompasses a biparatopic antibody or an antigen binding fragment thereof, that binds complement component 5a receptor (C5aR1) comprising: a light chain comprising a LCDR1 of SEQ ID NO: 9, a LCDR2 of SEQ ID NO: 10, and a LCDR3 of SEQ ID NO: 21; and
a heavy chain comprising: a HCDR1 of SEQ ID NO: 6, a HCDR2 of SEQ ID NO: 7, and a HCDR3 of SEQ ID NO: 8; a modified Fc domain comprising substitutions F234V, L235E, and D265G; and an scFv comprising a LCDR4 of SEQ ID NO: 22, a LCDR5 of SEQ ID NO: 23, a LCDR6 of SEQ ID NO: 24, a HCDR4 of SEQ ID NO: 18, a HCDR5 of SEQ ID NO: 19, and a HCDR6 of SEQ ID NO:20, wherein the scFv is linked to the modified Fc domain.

In one aspect, the present disclosure encompasses a biparatopic antibody or an antigen binding fragment thereof, that binds complement component 5a receptor (C5aR1) comprising: a first light chain variable region (VL) of SEQ ID NO: 15; a first heavy chain variable region (VH) of SEQ ID NO: 14; a modified Fc domain comprising substitutions F234V, L235E, and D265G; and an scFv comprising a second light chain variable region (VL) of SEQ ID NO: 17 and a second heavy chain variable region (VH) of SEQ ID NO of SEQ ID NO: 16, wherein the scFv is linked to the modified Fc domain.

In one aspect, the present disclosure encompasses a biparatopic antibody or an antigen binding fragment thereof, that binds complement component 5a receptor (C5aR1) comprising a light chain of SEQ ID NO: 72 and a heavy chain of SEQ ID NO:71.

In one aspect, the present disclosure encompasses a biparatopic antibody or an antigen binding fragment thereof, that binds complement component 5a receptor (C5aR1) comprising: a first light chain variable region (VL) of SEQ ID NO: 25; a first heavy chain variable region (VH) of SEQ ID NO: 14; and a scFv comprising a second light chain variable region (VL) of SEQ ID NO: 17 and a second heavy chain variable region (VH) of SEQ ID NO of SEQ ID NO: 16, wherein the scFv is linked to the Fc domain. In one embodiment, the biparatopic antibody or an antigen binding fragment thereof comprises a modified Fc domain comprising substitutions F234V, L235E, and D265G, such that the scFv is linked to the modified Fc domain.

In one aspect, the present disclosure encompasses an antibody or antigen binding fragment thereof, that binds complement component 5a receptor 1 (C5aR1) comprising: a heavy chain variable region (VH) of SEQ ID NO: 43; and a light chain variable region (VL) of SEQ ID NO: 48. In one embodiment, the antibody further comprises a modified Fc domain comprising substitutions F234V, L235E, and D265G.

In one aspect, the present disclosure encompasses an antibody or antigen binding fragment thereof, that binds complement component 5a receptor 1 (C5aR1) comprising: a heavy chain variable region (VH) of SEQ ID NO: 14; and a light chain variable region (VL) of SEQ ID NO: 15. In one embodiment, the antibody, further comprises a modified Fc domain comprising substitutions F234V, L235E, and D265G.

BRIEF DESCRIPTION OF FIGURES

FIG. 7A is an exemplary graph showing inhibition of calcium signaling using an exemplary humanized Site II antibody, as described in this disclosure, in the presence of increasing concentrations of C5a and increasing concentrations of antibody. FIG. 7B is an exemplary graph showing inhibition of calcium signaling using an exemplary humanized biparatopic antibody, as described in this disclosure, in the presence of increasing concentrations of C5a and increasing concentrations of antibody. FIG. 7C is an exemplary graph showing inhibition of calcium signaling using avacopan, a known C5aR1 inhibitor, as described in this disclosure, in the presence of increasing concentrations of C5a and increasing concentrations of antibody FIG. 9A is an exemplary graph showing inhibition of CD11b expression in neutrophils by an exemplary humanized Site II antibody, c2139 and an exemplary biparatopic antibody, c2137-e1711 as described herein, as compared to avacopan, and in the presence of 100 nM C5a and increasing antibody concentrations. FIG. 9B is an exemplary graph showing inhibition of CD11b expression in neutrophils by an exemplary humanized Site II antibody, c2139 and an exemplary biparatopic antibody, c2137-e1711 as described herein, as compared to avacopan, and in the presence of 10 nM an exemplary humanized Site II antibody and an exemplary biparatopic antibody and increasing concentrations of C5a. FIG. 9C is an exemplary graph showing inhibition of CD11b expression in neutrophils by an exemplary humanized Site II antibody, c2139 and an exemplary biparatopic antibody, c2137-e1711 as described herein, as compared to 10 nM and 100 nM anti-C5aR1 control Ab, and in the presence of 10 nM an exemplary humanized Site II antibody and an exemplary biparatopic antibody and increasing concentrations of C5a.

FIG. 10A is an exemplary graph showing the inhibition of beta arrestin recruitment on in the presence of exemplary humanized C5aR1 antibodies c2139 and c2137-e1711, each at a dose of 1 nM compared to 10 nM Avacopan, in the presence of 1 nM C5a. FIG. 10B is an exemplary graph showing the inhibition of beta arrestin recruitment on in the presence of exemplary humanized C5aR1 antibodies c2139 and c2137-e1711, each at a dose of 1 nM compared to 10 nM Avacopan, in the presence of 10 nM C5a. FIG. 10C is an exemplary graph showing the inhibition of beta arrestin recruitment on in the presence of exemplary humanized C5aR1 antibodies c2139 and c2137-e1711, each at a dose of 1 nM compared to 10 nM Avacopan, in the presence of 100 nM C5a.

FIG. 12A is an exemplary graph showing internalization of exemplary humanized anti-10 nM C5aR1 antibodies after 0, 6 and 12 hours in C5aR1-U937 cells, as visualized by amine-conjugated antibodies with a pH sensitive fluorescent dye. FIG. 12B is an exemplary graph showing internalization of exemplary humanized anti-10 nM C5aR1 antibodies after 0, 6 and 12 hours in U937 cells, as visualized by amine-conjugated antibodies with a pH sensitive fluorescent dye. FIG. 12C is an exemplary graph showing internalization of exemplary humanized anti-100 nM C5aR1 antibodies after 0, 6 and 12 hours in C5aR1-U937 cells, as visualized by amine-conjugated antibodies with a pH sensitive fluorescent dye. FIG. 12D is an exemplary graph showing internalization of exemplary humanized anti-100 nM C5aR1 antibodies after 0, 6 and 12 hours in U937 cells, as visualized by amine-conjugated antibodies with a pH sensitive fluorescent dye.

FIG. 15A is an exemplary schematic diagram of the study design in hC5aR1 mice showing time of blood draw and dosing.

FIG. 18A is an exemplary graph showing internalization several hours after dissociation of monospecific antibody, c2139. FIG. 18B is an exemplary graph showing increase in internalization of biparatopic antibody, c2137-e1711, during association.

FIG. 19A shows Ga signaling in the presence of C5aR1 Fc-modified antibodies in the presence of 10 nM C5a. FIG. 19B shows Ga signaling in the presence of C5aR1 Fc-modified antibodies in the presence of 100 nM C5a.

FIG. 20A is a dose response curve showing the exemplary graph showing inhibition of calcium signaling using an exemplary Fc modified humanized Site II antibody, as described in this disclosure, in the presence of increasing concentrations of the antibody and 100 nM C5a. FIG. 20B is a percent inhibition graph showing inhibition of calcium signaling using an exemplary Fc modified humanized Site II antibody, as described in this disclosure, in the presence of the antibody and 100 nM C5a.

FIG. 21A shows inhibition of calcium signaling in U937-C5aR1 cells in the presence of 10 nM C5a. FIG. 21B shows inhibition of calcium signaling in U937-C5aR1 cells in the presence of 100 nM C5a. FIG. 21C shows inhibition of calcium signaling in human neutrophils in the presence of 10 nM C5a. FIG. 21D shows inhibition of calcium signaling in human neutrophils in the presence of 100 nM C5a.

FIGS. 23A-23B show inhibition of C5a-meditated β-arrestin signaling by c2137-e1711-F$_c$mod and c2139-Fcmod. FIG. 23A shows the inhibitory dose-response of β-arrestin signaling by c2137-e1711-F$_c$mod and c2139-Fcmod. FIG. 23B shows the percent inhibition of β-arrestin signaling by c2137-e1711-F$_c$mod and c2139-Fcmod.

FIG. 24A shows the inhibition of chemotaxis in C5aR1-U937 stable cells in the presence of 1 nM, 3.16 nM and 10 nM c2139-Fcmod and increasing concentration of C5a. FIG. 24B shows the inhibition of chemotaxis in C5aR1-U937 stable cells in the presence of 1 nM, 3.16 nM and 10 nM C5a c2137-e1711-Fcmod and increasing concentration of C5a. FIG. 24C-24D shows the inhibition of chemotaxis in C5aR1-U937 stable cells in the presence of 1 nM, 3.16 nM and 10 nM an anti-C5aR1 control Ab and Avacopan, respectively, in the presence of c2137-e1711-Fcmod.

FIG. 25A shows the inhibition of CD11b signaling in the presence of increasing concentration of C5aR1 antagonistic antibody and 10 nM C5a. FIG. 25B shows the inhibition of CD11b signaling in the presence of increasing concentration of C5aR1 antagonistic antibody and 100 nM C5a.

FIG. 26A shows inhibition of ROS production of increasing concentration of monospecific C5aR1 antibody. FIG. 26B shows inhibition of ROS production of increasing concentration of biparatopic C5aR1 antibody.

FIGS. 29A-29B are graphical representations of pharmacokinetics of Fc modified antibodies. FIG. 29A is a graphical representation of the percentage of the Fc modified C5aR1 antibodies in the blood serum for 500 hours. FIG. 29B is a graphical representation of mean concentration in μg antibody/ml of serum over 500 hours.

FIGS. 30A-30F are graphical representations of PK and PD studies of the Fc modified C5aR1 antibodies, as compared to MVZ-IgG4. FIG. 30A is a graphical representation of a dose response curve of c2139Fcmod in serum for 200 hours. FIG. 30B is a graphical representation of a dose response curve of c2137-e1711-Fcmod in serum for 200 hours. FIG. 30C is a comparison of c2139Fcmod, c2137-e1711-Fcmod and MVZ-IgG4. FIG. 30D is in silico graphical representation of c2139 at three different concentrations over a period of 500 hours. FIG. 30E is an in silico graphical representation of c2137-e1711 at three different concentrations over a period of 500 hours. FIG. 30F is in silico graphical representation of isotype control antibody over a period of 500 hours at a concentration of 20 mg/Kg.

FIG. 32A shows the fluorescence intensity of c2139-Fcmod and c2137-e1711-Fcmod over 0, 6 hr and 24 hr in U937 cells. FIG. 32B shows the internalization of both c2137-e1711-Fcmod and c2139-Fcmod in live cells as observed by Nikon confocal experiment over a period of 300 min.

DEFINITIONS

Figure 1:
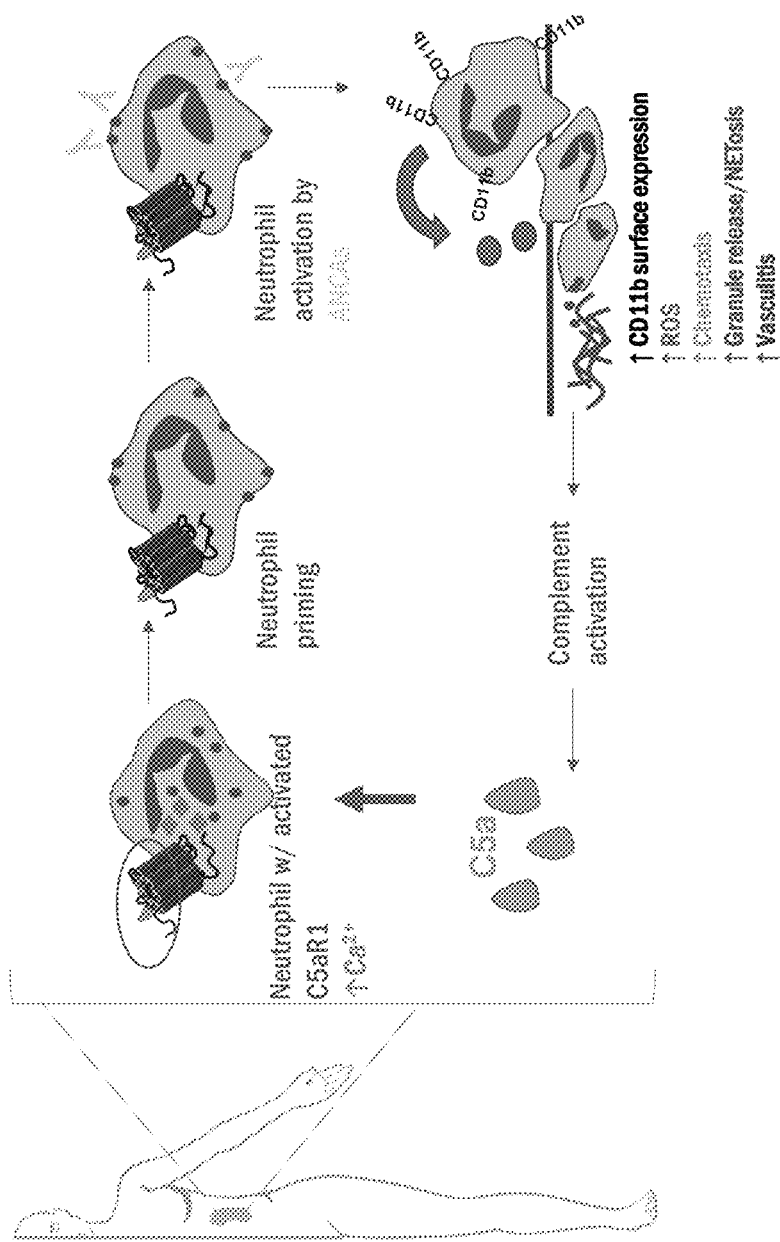
FIG. 1 is an exemplary schematic diagram showing the pathogenesis of ANCA-vasculitis

Antibody: As used herein, the term "antibody" refers to immunoglobulin molecules and immunologically active portions of immunoglobulin (Ig) molecules, i.e., molecules that contain an antigen binding site that binds (immunoreacts with) an antigen. By "binds" or "immunoreacts with" is meant that the antibody reacts with one or more antigenic determinants of the desired. Antibodies include, antibody fragments. Antibodies also include, but are not limited to, polyclonal, monoclonal, chimeric dAb (domain antibody), single chain, Fab, Fab', F(ab')2 fragments, scFvs, and Fab expression libraries. An antibody may be a whole antibody, or immunoglobulin, or an antibody fragment.

Antibody dependent cytotoxicity: As used herein, the term "antibody-dependent cytotoxicity" or "ADCC" refers to lysis of human target cells by an antibody according to the invention in the presence of effector cells.

Fab arm exchange: The term, "Fab arm exchange" refers to the phenomenon that IgG4 antibodies can exchange 'half-molecules', an activity termed Fab arm exchange herein. Especially in bispecific or biparatopic molecules, this results in functionally monovalent antibodies with unknown specificity and hence, potentially, reduced therapeutic efficacy. Mutations can be introduced in the Fc domain to inhibit the Fab arm exchange. It is known that S228P mutation can prevent IgG4 FAE to undetectable levels both in vitro and in vivo.

Fc domain: As used herein, the term "Fc region" refers to a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

Humanized antibody: The term "humanized antibody" includes non-human (e.g., murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, hamster) that have the desired specificity, affinity, and capability (Jones et al., *Nature* 321:522-525, 1986; Riechmann et al., *Nature* 332:323-327, 1988; Verhoeyen et al., *Science* 239:1534-1536, 1988).

Increased ADCC: The term "increased ADCC" is defined as either an increase in the maximum percentage of specific lysis observed within the antibody concentration range tested above, and/or a reduction in the concentration of antibody required to achieve one half of the maximum percentage of specific lysis observed within the antibody concentration range tested above. The increase in ADCC is relative to the ADCC, measured with an acceptable, art-recognized assay.

Monoclonal Antibody: The term "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

Multispecific antibody: As used herein, the term "multispecific antibody" refers to binding molecules, antibodies, or antigen-binding fragments thereof that have the ability to specifically bind to two or more different epitopes on the same or different target(s).

Biparatopic antibody: As used herein, the term "biparatopic antibody" refers to a multispecific antibody having the capability of binding 2 different non-overlapping epitopes on the same target antigen molecule.

$K_i$ or $K_d$: As used herein, the term "$K_d$", as used herein, refers to the dissociation constant of a particular antibody-antigen interaction as is known in the art, and would apply as a parameter of the binding affinity of a targeting moiety to its cognate ligand for the subject compositions.

IC50: As used herein, the term "IC50" refers to the concentration needed to inhibit half of the maximum biological response of the ligand agonist, and is generally determined by competition binding assays.

EC50: As used herein, the term "EC50" refers to a half maximal effective concentration. The term EC50 refers to the concentration of a drug, antibody or toxicant which induces a response halfway between the baseline and maximum after a specified exposure time. More simply, EC50 can be defined as the concentration required to obtain a 50% of the desired effect C5a: As used herein, the term "C5a" refers to complement component 5a.

C5aR1: As used herein, the term "C5aR1" refers to complement component 5a receptor 1. In some embodiments, the human C5aR1 comprises SEQ ID NO: 38. In some embodiments, certain amino acids of the human C5aR1 comprising SEQ ID NO: 38 have natural variants, such as (N2D and N279K), shown as lowercase letters in Table 1.

Linker: As used herein, the term "linker" refers to a molecule or group of molecules (such as a monomer or polymer) that connects two molecules and often serves to place the two molecules in a preferred configuration. A number of strategies may be used to covalently link molecules together. These include, but are not limited to polypeptide linkages between N- and C-terminus of proteins or protein domains, linkage via disulfide bonds, and linkage via chemical cross-linking reagents. In one aspect of this embodiment, the linker is a peptide bond, generated by recombinant techniques or peptide synthesis. In some embodiments, the linker may contain amino acid residues that provide flexibility. Thus, the linker peptide may predominantly include the following amino acid residues: Gly, Ser, Ala, or Thr. The linker peptide should have a length that is adequate to link two molecules in such a way that they assume the correct conformation relative to one another so that they retain the desired activity. Suitable lengths for this purpose include at least one and not more than 30 amino acid residues. In one embodiment, the linker is from about 1 to 30 amino acids in length. In another embodiment, the linker is from about 1 to 15 amino acids in length. In addition, the amino acid residues selected for inclusion in the linker peptide should exhibit properties that do not interfere significantly with the activity of the polypeptide.

Neutrophil: As used herein, the term "neutrophil" refers to the major class of white blood cells in peripheral blood. Neutrophils have an important role in engulfing and killing extracellular pathogens.

scFv: As used herein, the term "scFv" refers to a fusion protein of the variable regions of the heavy (VH) and light chains (VL) of immunoglobulins, connected with a short linker peptide of ten to about 25 amino acids.

Fab: As used herein, the term "Fab" refers to an antibody fragment comprising a portion of an intact antibody, comprising the antigen-binding or variable region thereof.

Neutropenia: As used herein, the term "neutropenia" refers to low neutrophil count. For example, in a human subject, neutropenia can range from less than 500 ANC to less than 1500 ANC (absolute neutrophil count). The ANC is measured in cells per microliter of blood). Neutropenia in mice is defined as <10 neutrophils/mm$^3$ blood.

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Subject: As used herein, the term "subject" refer to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Dysfunction: As used herein, the term "dysfunction" refers to an abnormal function. A dysfunction of a molecule (e.g, a protein) can be caused by an increase or decrease in activity associated with such molecule. A dysfunction of a molecule can be caused by a defect associated with the molecule itself, or other molecules that interact directly or indirectly with or regulate the molecule.

Derivatives: As used herein, the term "derivatives" when used in connection with antibody, or C5aR1 antibodies, refer to a portion having some of the sequence of an original molecule that retains at least some of the functions and/or properties of the original molecule.

Identity: As used herein, the term "identity" refers a relationship between the sequences of two or more polypeptide molecules or two or more nucleic acid molecules as known in the art, comparing the sequences of these molecules. The relationship determined by doing. In the art, "identity" also means the degree of sequence relatedness between nucleic acid molecules or polypeptides, and in some cases more than one nucleotide sequence or more than one. It may be determined by a match between amino acid sequence strings. "Identity" means between a gap alignment (if any) addressed by a particular mathematical model or computer program (i.e., an "algorithm") and a smaller sequence of two or more sequences. Measure the percent identity match.

Similarity or Similar: As used herein, the term "similarity" is used in the art with respect to related concepts, but in contrast to "identity," "similarity", refers to both identity and conservative substitution matches. If two polypeptide sequences have, for example, 10 identical amino acids out of 20 amino acids and the rest are all non-conservative substitutions, the percent identity and percent similarity are both 50%. In the same example, if there are 5 more conservative substitutions, the percent identity remains 50%, but the percent similarity is 75%. Thus, if there are conservative substitutions, the percent similarity between the two polypeptides is higher than the percent identity between these two polypeptides.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Vector: The term "vector" refers to a polynucleotide (usually DNA) used to artificially carry foreign genetic material to another cell where it can be replicated or expressed. Non-limiting exemplary vectors include plasmids, viral vectors, cosmids, and artificial chromosomes. Such vectors may be derived from a variety of sources, including bacterial and viral sources. A non-limiting exemplary viral source for a plasmid is adeno-associated virus.

Various aspects of the disclosure are described in detail in the following sections. The use of sections is not meant to limit the disclosure. Each section can apply to any aspect of the disclosure. In this application, the use of "or" means "and/or" unless stated otherwise. As used herein, the singular forms "a", "an", and "the" include both singular and plural referents unless the context clearly dictates otherwise.

DETAILED DESCRIPTION

The present disclosure describes antibodies, nucleic acids and systems for the manufacture thereof and uses and methods for the treatment of diseases associated with an dysfunctional C5a/C5aR1 axis signaling, in particular autoimmune diseases such as, but not limited to ANCA-associated vasculitis, lupus, rheumatoid arthritis, inflammatory bowel disease, C3 glomerulopathy (C3G), hidradenitis suppurativa (HS), atypical hemolytic uremic syndrome Lupus nephritis, IgA nephropathy, myasthenia gravis, macular degeneration, Alzheimers Disease, Amylotrophic Lateral Sclerosis, Huntington's Disease, neuropathic pain, COVID-19 infection, allergic asthma, chronic obstructive pulmonary disease, bullous pemphigoid, pyoderma gangrenosum and psoriasis.

ANCA-associated vasculitis is a group of diseases (granulomatosis with polyangiitis, eosinophilic granulomatosis with polyangiitis and microscopic polyangiitis), characterized by destruction and inflammation of small vessels. Antineutrophil cytoplasmic autoantibodies (ANCA) are the cause of ANCA-associated vasculitis. Experimental data in animal models and in vitro experiments demonstrate that primed neutrophils are activated by ANCA, which generates C5a that engages C5a receptors on neutrophils. This attracts and in turn primes more neutrophils for activation by ANCA. The C5a binding to C5aR1 may play a central role in the pathogenesis of ANCA-associated vasculitis. The general schematic of ANCA vasculitis is shown in FIG. 1. The standard treatment is immunosuppressive therapy with glucocorticoids; these therapies are associated with substantial short- and long-term toxicity. Avacopan, a C5aR1 binding antagonist small molecule, was recently accepted by the FDA for use in ANCA-associated vasculitis. However, in vitro data suggest that avacopan antagonism of C5a can be overcome by high concentrations of C5a. It is known that C5a concentration at the site of inflammation in active AAV may reach 100 nM. It is known that under such conditions the inhibition of C5aR1 by avacopan can be overcome. There is a need for development of robust inhibitors of the C5a/C5aR1 axis for counteracting disorders associated with dysfunction of this pathway. The present disclosure provides compositions and methods of treatment of C5a/C5aR1 axis dysfunction associated disorders, using a biological C5aR1 antagonists.

Figure 2:
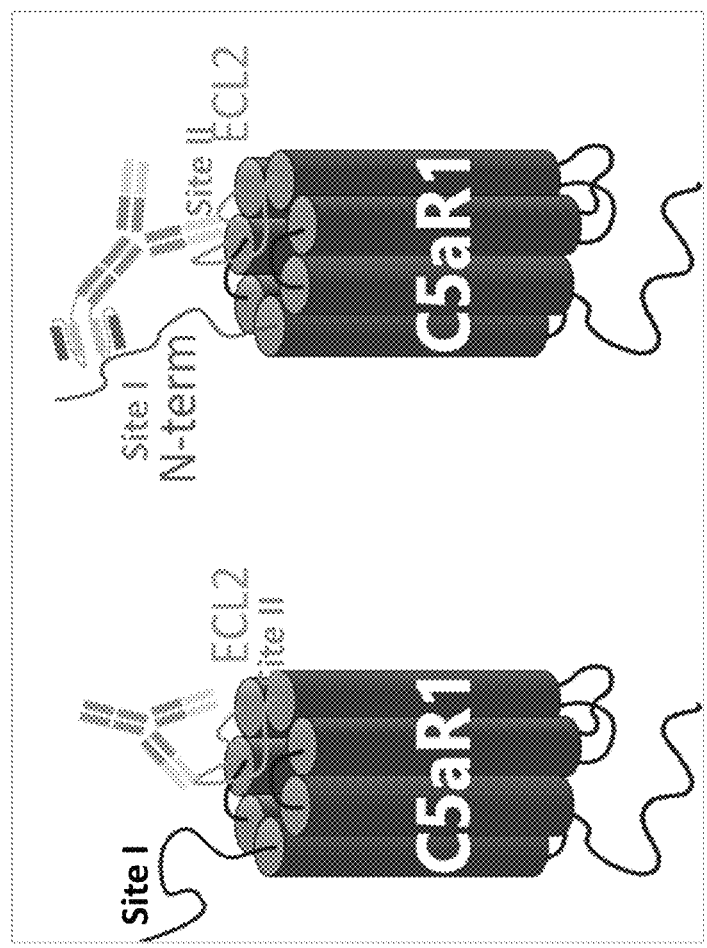
FIG. 2 is an exemplary schematic diagram of the two kinds of antibodies described in this disclosure.

In some aspects, provided herewith are two groups of exemplary antibodies binding and antagonizing C5aR1. A schematic representation of the two groups of antibodies in the instant disclosure is shown in FIG. 2.

The energy of agonist binding to the extracellular domain transmits an allosteric conformational change to the transmembrane and intracellular domains, allowing for G-protein binding and signaling. C5aR1 has two known agonists: C5a and C5a$^{desArg}$. C5a has a short half-life in serum as the C-terminal arginine is quickly cleaved by carboxypeptidase N to form C5a$^{desArg}$, which binds to C5aR1 with reduced affinity and displays biased signaling. C5a$^{desArg}$, unlike C5a, does not signal the β-arrestin pathway and does not stimulate granulocyte release. However, C5a$^{desArg}$ does stimulate neutrophil chemotaxis, so it is of interest to also block C5a$^{desArg}$ binding to prevent neutrophil migration to the site of inflammation. C5a$^{desArg}$ signaling favors chemotaxis and is not prone to desensitization (e.g., neutrophils continue to migrate until reach high concentrations of C5a, not C5a$^{desArg}$) In an embodiment, an orthosteric antagonist that blocks C5a binding (e.g., an antibody molecule as described herein) also inhibits (e.g., blocks) C5a$^{desArg}$ binding. Inhibition of C5a binding is, in some embodiments, needed at the inflammation site while inhibition of C5a$^{desArg}$ is at periphery and can prevent the migration of neutrophils to the inflammation site. Targeting C5aR1 typically leave the membrane attack complex pathway (C5b) untouched.

Design of Monospecific C5aR1 Antagonists

In some embodiments, the antibodies presented herein, bind a site defined by SEQ ID NO: 1 or SEQ ID NO: 2, also called "site I." Site I, typically comprises the N-terminal residues (e.g., N-terminal 37 residues) of C5aR1 and forms a flexible random coil structure, defined by SEQ ID NO: 1 or SEQ ID NO: 2. An antibody molecule that binds to Site I can typically bind to all residues in Site I or a subset thereof. For example, an antibody molecule that binds to Site I makes contact with one or more residues in Site I. In an embodiment, Site I generally comprises a number of sulfated residues (e.g., sulfated tyrosine resides) and a number of Asp residues.

In some embodiments, the antibodies presented herein, bind a site defined by SEQ ID NO: 3, also called "site II." Site II, typically comprises the extra cellular loop 2 (ECL2) and the transmembrane residues forming vestibule of C5aR1. In an embodiment, an antibody molecule that binds to Site II binds to ECL2, but does not bind, or does not substantially bind, to ECL1 and/or ECL3. In an embodiment, an antibody molecule that binds to Site II binds to ECL2 and ECL1, but does not bind, or does not substantially bind, to ECL3.

In some embodiments, the antibody molecules described herein are designed to target Site II, defined by amino acids of SEQ ID NO: 3. In some embodiments amino acid encompassing R175 to G189 of SEQ ID NO: 38 are core epitopes for binding of Site II antibody molecules described herein. In some embodiments, amino acid encompassing E180-P183 of SEQ ID NO: 38 are core epitopes for binding of Site II antibody molecules described herein. In some embodiments, amino acid encompassing E180-P184 of SEQ ID NO: 38 are core epitopes for binding of Site II antibody molecules described herein. In some embodiments, amino acid encompassing E178-P183 of SEQ ID NO: 38 are core epitopes for binding of Site II antibody molecules described herein. In some embodiments, one or more of the residues R35, H101, V176, V177, R178, E179, E180, Y181, F182, P183 P184, K185, L187, D191, S193, H194, E266, P267, S268, F272, L273 and/or K276 of C5aR1 (SEQ ID NO: 38) are important for binding of Site II antibodies described herein. In some embodiments one or more of the residues E180, Y181, F182, and/or P183 of SEQ ID NO: 38 are critical epitopes for binding of Site II antibodies described herein. In one embodiment, the amino acid residue W102 of SEQ ID NO: 38 is critical for binding of Site II antibodies described herein.

The sequences of SEQ ID NO: 1, SEQ ID NO: 2 and SEQ ID NO: 3 are presented in Table 1.

TABLE 1

The amino acid sequences of Site I, Site II and human C5aR1. Variants (N2D and N279K), are shown as lowercase letters.

| | |
|---|---|
| Site I sequence | MNSFNYTTPDYGHYDDKDTLDLNTPVDKTSNTLRVPD (SEQ ID NO: 1) |
| Site I sequence | MDSFNYTTPDYGHYDDKDTLDLNTPVDKTSNTLRVPD (SEQ ID NO: 2) |
| Site II sequence | RVVREEYFPPKVLCGVDYSHDKRRER (SEQ ID NO: 3) |
| hC5aR1 | MnSFNYTTPDYGHYDDKDTLDLNTPVDKTSNTLRVPDILAL VIFAVVFLVGVLGNALVVWVTAFEAKRTINAIWFLNLAVAD FLSCLALPILFTSIVQHHHWPFGGAACSILPSLILLNMYAS ILLLATISADRFLLVFKPIWCQNFRGAGLAWIACAVAWGLA LLLTIPSFLYRWREEYFPPKVLCGVDYSHDKRRERAVAIVR LVLGFLWPLLTLTICYTFILLRTWSRRATRSTKTLKVWAWA SFFIFWLPYQVTGIMMSFLEPSSPTFLLLnKLDSLCVSFAY INCCINPIIYVVAGQGFQGRLRKSLPSLLRNVLTEESVVRE SKSFTRSTVDTMAQKTQAV (SEQ ID NO: 38) |

In some aspects, exemplary humanized site I (SEQ ID NO: 1 or SEQ ID NO: 2) binding antibodies, presented herein comprise a heavy chain variable region (HCVR or VH) comprising the amino acid sequences of SEQ ID NO: 16 or SEQ ID NO: 39 to SEQ ID NO: 43 or sequence having at least 80%, 85%, 90%, 95% or 99% identity thereto and/or a light chain variable region (LCVR or VL) comprising an amino acid sequence of SEQ ID NO: 17 or SEQ ID NO: 44 to SEQ ID NO: 49 or a sequence having at least 80%, 85%, 90%, 95% or 99% identity thereto. Table 2a summarizes the amino acid sequences of VH and VL of exemplary site I binding antibodies. In some embodiments, the three heavy chain complementarity determining regions, HCDR1, HCDR2, and HCDR3 are found within the HCVR or VH (SEQ ID NO: 16 or SEQ ID NO: 39 to SEQ ID NO: 43). In some embodiments, three light chain complementarity determining regions, LCDR1, LCDR2, and LCDR3 are found within the LCVR or VL (SEQ ID NO: 17 or SEQ ID NO: 44 to SEQ ID NO: 49). It is noted that An exemplary humanized full length Site I binding antibody can comprise any combination of a VH selected from an amino acid sequence of SEQ ID NO: 16 or SEQ ID NO: 39-43 and a VL selected from an amino acid sequence of SEQ ID NO: 17 or SEQ ID NO: 44-49.

It is noted that a humanized full length Site I binding antibody can comprise any combination of a VH selected from any of amino acid sequence of SEQ ID NO: 16 or SEQ ID NO: 39-43 or an amino acid sequence 80%, 85%, 90%, 95%, 98%, 99% identical to SEQ ID NO: 16 or SEQ ID NO: 39-43 and a VL selected from any of amino acid sequence of SEQ ID NO: 17 or SEQ ID NO: 44-49 or an amino acid sequence 80%, 85%, 90%, 95%, 98%, 99% identical to SEQ ID NO: 17 or SEQ ID NO: 44-49.

In some embodiments, an exemplary site I binding antibody, e1711, comprises a heavy chain of SEQ ID NO: 17 or an amino acid sequence 80%, 85%, 90%, 95%, 98%, 99% identical to SEQ ID NO: 17. In some embodiments, the exemplary site I binding antibody, e1711 comprises light chain of SEQ ID NO: 16, or an amino acid sequence 80%, 85%, 90%, 95%, 98%, 99% identical to SEQ ID NO: 16.

In some embodiments, an exemplary site I binding antibody, e1711, comprises a heavy chain of SEQ ID NO: 43 or an amino acid sequence 80%, 85%, 90%, 95%, 98%, 99% identical to SEQ ID NO: 43. In some embodiments, the exemplary site I binding antibody, e1711 comprises light chain of SEQ ID NO: 48, or an amino acid sequence 80%, 85%, 90%, 95%, 98%, 99% identical to SEQ ID NO: 48.

In some embodiments, the exemplary site I binding antibody, e1711 presented herein comprises a e11L variable light chain and e11H variable heavy chain comprises a heavy chain comprising the amino acid sequence of SEQ ID NO: 77 or a sequence having at least 60%, 65%, 70%, 75%, 80%, 85%, 90%, 95% or 99% identity thereto and/or a light chain comprising an amino acid sequence of SEQ ID NO: 78 or a sequence having at least 60%, 65%, 70%, 75%, 80%, 85%, 90%, 95% or 99% identity thereto.

TABLE 2a

Variable regions of exemplary humanized Site I binding antibodies

Humanized Site I antibodies: Heavy chain variable regions (SEQ ID NO: 16; SEQ ID NO: 39-43)

| | |
|---|---|
| e1H | QVQLVQSGAEVKKPGASVKVSCAASGFTFNAYAMSWVRQAP GQGLEWMGSISTGGNTYYAQKFQGRVTMTRDTSTSTVYMEL SSLRSEDTAVYYCTRGYQRFSGFAYWGQGTLVTVSS (SEQ ID NO: 39) |
| e11H | EVQLVESGGGLVQPGGSLRLSCAASGFTFNAYAMSWVRQAT GKGLEWVSSISTGGNTYYPGSVKGRFTISRENAKNSLYLQM NSLRAGDTAVYYCTRGYQRFSGFAYWGQGTLVTVSS (SEQ ID NO: 40) |
| e14H | EVQLVESGGGLVQPGGSLRLSCAASGFTFNAYAMSWVRQAT GKGLEWVSSISTGGNTYYPGSVKGRFTISRENAKNSLYLQM NSLRAGDTAVYYCARGYQRFSGFAYWGQGTLVTVSS (SEQ ID NO: 41) |
| e16H | EVQLLESGGGLVQPGGSLRLSCAASGFTFNAYAMSWVRQAP GKGLEWVSSISTGGNTYYADSVKGRFTISRENSKNTLYLQM NSLRAEDTAVYYCTRGYQRFSGFAYWGQGTLVTVSS (SEQ ID NO: 42) |
| e17H | EVQLVESGGGLIQPGGSLRLSCAASGFTFNAYAMSWVRQAP GKGLEWVSSISTGGNTYYADSVKGRFTISRDNSKNTLYLQM NSLRAEDTAVYYCTRGYQRFSGFAYWGQGTLVTVSS (SEQ ID NO: 43) |
| e1711H | EVQLVESGGGLIQPGGSLRLSCAASGFTFNAYAMSWVRQAP GKCLEWVSSISTGGNTYYADSVKGRFTISRDNSKNTLYLQM NSLRAEDTAVYYCTRGYQRFSGFAYWGQGTLVTVSS (SEQ ID NO: 16) |

TABLE 2a-continued

Variable regions of exemplary humanized Site I binding antibodies

Humanized Site I antibodies: Light chain variable regions (SEQ ID NO: 17; SEQ ID NO: 44-49)

| | |
|---|---|
| e3L | DIQMTQSPSSLSASVGDRVTITCRASQSIVHSNGNTYLNWY QQKPGKAPKLLIYKVSNRLSGVPSRFSGSGSGTDFTLTISS LQPEDFATYYCSQSTHVPYTFGQGTKLEIK (SEQ ID NO: 44) |
| e5L | DIVMTQTPLSSPVTLGQPASISCRSSQSLVHSNGNTYLNWL QQRPGQPPRLLIYKVSNRLSGVPDRFSGSGAGTDFTLKISR VEAEDVGVYYCSQSTHVPYTFGQGTKLEIK (SEQ ID NO: 45) |
| e6L | DVVMTQTPLSSPVTLGQPASISCRSSQSLVHSNGNTYLNWY QQRPGQPPRLLIYKVSNRLSGVPDRFSGSGAGTDFTLKISR VEAEDVGVYYCSQSTHVPYTFGQGTKLEIK (SEQ ID NO: 46) |
| e8L | DVVMTQSPLSLPVTPGEPASISCRSSQSLVHSNGNTYLNWY LQKPGQSPQLLIYKVSNRLSGVPDRFSGSGSGTDFTLKISR VEAEDVGVYYCSQSTHVPYTFGQGTKLEIK (SEQ ID NO: 47) |
| e11L | EIVLTQSPATLSLSPGERATLSCRSSQSLVHSNGNTYLNWY QQKPGQAPRLLIYKVSNRLSGIPARFSGSGSGTDFTLTISS LEPEDFAVYYCSQSTHVPYTFGQGTKLEIK (SEQ ID NO: 48) |
| e20L | EIVLTQSPGTLSLSPGERATLSCRASQSVVHSNGNTYLNWY QQKPGQAPRLLIYKVSNRLSGIPDRFSGSGSGTDFTLTISR LEPEDFAVYYCSQSTHVPYTFGQGTKLEIK (SEQ ID NO: 49) |
| e1711L | EIVLTQSPATLSLSPGERATLSCRSSQSLVHSNGNTYLNWY QQKPGQAPRLLIYKVSNRLSGIPARFSGSGSGTDFTLTISS LEPEDFAVYYCSQSTHVPYTFGCGTKLEIK (SEQ ID NO: 17) |

TABLE 2b

Heavy Chain and Light Chain of exemplary humanized Site I binding antibodies

| | |
|---|---|
| heavy chain of exemplary Site I monospecific antibody e1711 | EVQLVESGGGLIQPGGSLRLSCAASGFTFNAYAMSW VRQAPGKGLEWVSSISTGGNTYYADSVKGRETLSRL NSKNTLYLQMNSLRAEDTAVYYCTRGYQRFSGFAYW GQGTLVTVSSASTKGPSVFPLAPCSRSTSESTAALG CLVKDYFPEPVTVSWNSGALTSGVHTFPAVLQSSGL YSLSSVVTVPSSSLGTKTYTCNVDHKPSNTKVDKRV ESKYGPPCPPCPAPEFLGGPSVFLFPPKPKDTLMIS RTPEVTCVVVDVSQEDPEVQFNWYVDGVEVHNAKTK PREEQFNSTYRVVSVLTVLHQDWLNGKEYKCKVSNK GLPSSIEKTISKAKGQPREPQVYTLPPSQEEMTKNQ VSLTCLVKGFYPSDIAVEWESNGQPENNYKTTPPVL DSDGSFFLYSRLTVDKSRWQEGNVFSCSVMHEALHN HYTQKSLSLSLGK (SEQ ID NO: 77) |
| light chain of exemplary Site I monospecific antibody e1711 | EIVLTQSPATLSLSPGERATLSCRSSQSLVHSNGNT YLNWYQQKPGQAPRLLIYKVSNRLSGIPARFSGSGS GTDFTLTISSLEPEDFAVYYCSQSTHVPYTFGQGTK LEIKRTVAAPSVFIFPPSDEQLKSGTASVVCLLNNF YPREAKVQWKVDNALQSGNSQESVTEQDSKDSTYSL SSTLTLSKADYEKHKVYACEVTHQGLSSPVTKSFNR GEC (SEQ ID NO: 78) |

In some aspects, exemplary site II binding antibodies presented herein comprise a HCVR or VH comprising the amino acid sequences of SEQ ID NO; 14 or SEQ ID NO: 50 to SEQ ID NO: 59 or sequence having at least 80%, 85%, 90%, 95% or 99% identity thereto and/or a LCVR or VL comprising an amino acid sequence of SEQ ID NO: 60 to SEQ ID NO: 68 or a sequence having at least 80%, 85%, 90%, 95% or 99% identity thereto. Table 3 summarizes the amino acid sequences of VH and VL of exemplary site II binding antibodies. In some embodiments, the three heavy chain complementarity determining regions, HCDR1, HCDR2, and HCDR3 are found within the HCVR or VH (SEQ ID NO: 50 to SEQ ID NO: 59). In some embodiments, three light chain complementarity determining regions, LCDR1, LCDR2, and LCDR3 are found within the LCVR or VL (SEQ ID NO: 60 to SEQ ID NO: 68).

It is noted that a humanized full length Site II binding antibody can comprise any combination of a VH selected from an amino acid sequence of SEQ ID NO: 14 or SEQ ID NO: 50-59 or has at least 85, 90, 95, 99 or 100% identity with the amino acid sequence of any of SEQ ID NO: 14 or SEQ ID NO: 50-59 and a VL selected from an amino acid sequence of SEQ ID NO: 15 or SEQ ID NO: 25 or SEQ ID NO: 60-68 or has at least 85, 90, 95, 99 or 100% identity with the amino acid sequence of any of SEQ ID NO: 15 or SEQ ID NO: 25 or SEQ ID NO: 60-68.

TABLE 3

Variable regions of exemplary humanized Site II binding antibodies

Humanized Site II antibodies: Heavy chain variable regions (SEQ ID NO: 14; SEQ ID NO: 50-59)

a4H QVQLVQSGAEVKKPGASVKVSCKASGYSFSSSWINWVRQAPGQ
GLEWMGRISAYDGDTRYAQKLQGRVTMTADKSTSTAYMELRSL
RSDDTAVYYCVRFLITSTRYVMDYWGQGTTVTVSS
(SEQ ID NO: 50)

a9H QVQLVQSGAEVKKPGASVKVSCKASGYSFSSSWMNWVRQAPGQ
RLEWMGRISAGDGDTRYSQKFQGRVTITADKSASTAYMELSSL
RSEDTAVYYCVRFLITSTRYVMDYWGQGTTVTVSS
(SEQ ID NO: 51)

a16H QVQLVQSGAEVKKPGSSVKVSCKASGGSFSSSWINWVRQAPGQ
GLEWMGRISPGDGDTRYAQKFQGRVTITADKSTSTAYMELSSL
RSEDTAVYYCVRFLITSTRYVMDYWGQGTTVTVSS
(SEQ ID NO: 52)

a20H QVQLVQSGAEVKKPGASVKVSCKASGYSFSSSWINWVRQATGQ
GLEWMGRMSPGDGDTRYAQKFQGRVTMTANKSISTAYMELSSL
RSEDTAVYYCVRFLITSTRYVMDYWGQGTTVTVSS
(SEQ ID NO: 53)

a26H EVQLVQSGAEVKKPGESLRISCKASGYSFSSSWMNWVRQMPGK
GLEWMGRISPGDGDTRYSPSFQGHVTISADKSISTAYLQWSSL
KASDTAMYFCVRFLITSTRYVMDYWGQGTTVTVSS
(SEQ ID NO: 54)

a30H EVQLVQSGAEVKKPGESLKISCKGSGYSFSSSWINWVRQMPGK
GLEWMGRISPGDGDTRYSPSFQGQVTISADKSISTAYLQWSSL
KASDTAMYYCVRFLITSTRYVMDYWGQGTTVTVSS
(SEQ ID NO: 55)

c2H QVQLVQSGAEVKKPGASVKVSCKASGYTFTNYWMHWVRQAPGQ
GLEWMGYLNPSSGYTKYAQKLQGRVTMTADKSTSTAYMELRSL
RSDDTAVYYCTRSGGDNYGNPYYFDRWGQGTTVTVSS
(SEQ ID NO: 56)

c13H QVQLVQSGAEVKKPGASVKVSCKASGYTFTNYWMHWVRQAPGQ
RLEWMGYLNPSSGYTKYSQKFQGRVTITRDTSASTAYMELSSL
RSEDTAVYYCTRSGGDNYGNPYYFDRWGQGTTVTVSS
(SEQ ID NO: 57)

c32H QVQLVQSGAEVKKPGASVKVSCKASGYTFTNYWIHWVRQATGQ
GLEWMGYMNPSSGYTKYAQKFQGRVTMTANKSISTAYMELSSL
RSEDTAVYYCTRSGGDNYGNPYYFDRWGQGTTVTVSS
(SEQ ID NO: 58)

c21H QVQLVQSGAEVKKPGASVKVSCKASGYTFTNYWMHWVRQAPGQ
GLEWMGYLNPSSGYTKYAQKFQGRVTMTRDTSTSTVYMELSSL
RSEDTAVYYCTRSGGDNYGNPYYFDRWGQGTTVTVSS
(SEQ ID NO: 14)

TABLE 3-continued

Variable regions of exemplary humanized Site II binding antibodies c40H EVQLVQSGAEVKKPGESLKISCKGSGYTFTNYWIHWVRQMPGK
GLEWMGYINPSSGYTKYSPSFQGQVTISADKSISTAYLQWSSL
KASDTAMYYCTRSGGDNYGNPYYFDRWGQGTTVTVSS
(SEQ ID NO: 59)

Humanized Site II antibodies: Light chain variable regions (SEQ ID NO: 15; SEQ ID NO: 25; SEQ ID NO: 60-68)

a1L DIQMTQSPSSLSASVGDRVTITCRSSQSLVHSNGNTYLHWYQQ
KPGKAPKLLIYKVSNRFSGVPSRFSGSGSGTDFTLTISSLQPE
DFATYYCSQSTLVPPTFGQGTKLEIK
(SEQ ID NO: 60)

a6L DVVMTQTPLSSPVTLGQPASISCRSSQSLVHSNGNTYLHWYQQ
RPGQPPRLLIYKVSNRFSGVPDRFSGSGAGTDFTLKISRVEAE
DVGVYYCSQSTLVPPTFGQGTKLEIK
(SEQ ID NO: 61)

a15L EVVMTQSPATLSVSPGERATLSCRSSQSLVHSNGNTYLHWYQQ
KPGQAPRLLIYKVSNRFSGIPARFSGSGSGTEFTLTISSLQSE
DFAVYYCSQSTLVPPTFGQGTKLEIK
(SEQ ID NO: 62)

c4L DVQMTQSPSSLSASVGDRVTITCRASQSIVHSNGNTYLHWYQQ
KPGKAPKFLIYKVSNRFSGVPSRFSGSGSGTDFTLTISSLQPE
DFATYYCSQSTLVPLTFGQGTKLEIK
(SEQ ID NO: 63)

c6L DVVMTQTPLSSPVTLGQPASISCRSSQSLVHSNGNTYLHWYQQ
RPGQPPRFLIYKVSNRFSGVPDRFSGSGAGTDFTLKISRVEAE
DVGVYYCSQSTLVPLTFGQGTKLEIK
(SEQ ID NO: 64)

c8L DVVMTQSPLSLPVTPGEPASISCRSSQSLVHSNGNTYLHWYLQ
KPGQSPQFLIYKVSNRFSGVPDRF3GSGSGTDFTLKISRVEAE
DVGVYYCSQSTLVPLTFGQGTKLEIK
(SEQ ID NO: 65)

c9L DVVMTQSPLSLPVTLGQPASISCRSSQSLVHSNGNTYLHWFQQ
RPGQSPRRLIYKVSNRFSGVPDRFSGSGSGTDFTLKISRVEAE
DVGVYYCSQSTLVPLTFGQGTKLEIK
(SEQ ID NO: 66)

c10L DVVMTQSPLSLPVTLGQPASISCRSSQSLVHSNGNTYLHWYQQ
RPGQSPRFLIYKVSNRFSGVPDRFSGSGSGTDFTLKISRVEAE
DVGVYYCSQSTLVPLTFGQGTKLEIK
(SEQ ID NO: 67)

c38L DVQMTQSPSSLSASVGDRVTITCRASQSIVHSNGNTYLHWYQQ
KPGKAPKFLIYKVSNRFSGVPSRFSGSGSGTDFTLTISSLQPE
DFATYYCSQYTLVPLTFGQGTKLEIK
(SEQ ID NO: 68)

c37L DVQMTQSPSSLSASVGDRVTITCRASQSIVHSNGNTYLHWYQQ
KPGKAPKFLIYKVSNRFSGVPSRFSGSGSGTDFTLTISSLQPE
DFATYYCAQSTLVPLTFGQGTKLEIK
(SEQ ID NO: 15)

c39L DVQMTQSPSSLSASVGDRVTITCRASQSIVHSNGNTYLHWYQQ
KPGKAPKFLIYKVSNRFSGVPSRFSGSGSGTDFTLTISSLQPE
DFATYYCAQYTLVPLTFGQGTKLEIK
(SEQ ID NO: 25)

In some aspects, an exemplary Site II binding antibody comprises a combination of c39L (SEQ ID NO: 14) and c21H (SEQ ID NO: 25) to produce antibody c2139.

In some embodiments, the exemplary site II binding antibody, c2139 presented herein comprises a c39L variable light chain and c21H variable heavy chain comprises a heavy chain comprising the amino acid sequence of SEQ ID NO: 4 or a sequence having at least 60%, 65%, 70%, 75%, 80%, 85%, 90%, 95% or 99% identity thereto and/or a light chain comprising an amino acid sequence of SEQ ID NO: 5 or a sequence having at least 60%, 65%, 70%, 75%, 80%, 85%, 90%, 95% or 99% identity thereto.

In some embodiments, the exemplary site II binding antibody, c2137 presented herein comprises a c37L variable light chain and c21H variable heavy chain comprises a heavy chain comprising the amino acid sequence of SEQ ID NO: 4 or a sequence having at least 60%, 65%, 70%, 75%, 80%, 85%, 90%, 95% or 99% identity thereto and/or a light chain comprising an amino acid sequence of SEQ ID NO: 75 or a sequence having at least 60%, 65%, 70%, 75%, 80%, 85%, 90%, 95% or 99% identity thereto.

In some aspects, an exemplary site II (SEQ ID NO: 3) binding antibody, c2139, presented herein comprises a heavy chain comprising a HCVR or VH, wherein the HCVR or VH comprises three heavy chain complementarity determining regions, HCDR1, HCDR2, and HCDR3, comprising SEQ ID NO: 6, SEQ ID NO: 7 and SEQ ID NO: 8 respectively. In some embodiments, the exemplary site II binding antibody presented herein further comprise a LCVR or VL, wherein the LCVR or VL comprises three light chain complementarity determining regions, LCDR1, LCDR2, and LCDR3, comprising SEQ ID NO: 9, SEQ ID NO: 10 and SEQ ID NO: 11 respectively or comprises a sequence that differs by no more than 5, 4, 3, 2 or 1 amino acids from amino acids of SEQ ID NOs: 6, 7, 8, 9, 10 and/or 11. The sequences of heavy chain, light chain and HCDR and LCDR are presented in Table 4a.

In some aspects, the exemplary site II binding antibody, c2139, presented herein comprise a HCVR or VH comprising the amino acid sequence of SEQ ID NO: 14 or a sequence having at least 80%, 85%, 90%, 95% or 99% identity thereto and/or a LCVR or VL comprising an amino acid sequence of SEQ ID NO: 25 or a sequence having at least 80%, 85%, 90%, 95% or 99% identity thereto.

In one aspect, described herein is an exemplary antibody molecule capable of binding to complement component 5a receptor 1 (C5aR1), c2139, wherein the antibody molecule competes with a C5aR1 antibody molecule capable of binding to one or more residues of amino acids of Site II (SEQ ID NO: 3).

In some embodiments, the exemplary site II binding antibodies comprise a glycine or alanine at position 89 of the VH. In some embodiments the exemplary site II binding antibodies comprise tyrosine at position 91. In some embodiments, the exemplary site II binding antibodies comprise tyrosine at position 91 and glycine or alanine at position 89 of the VH.

TABLE 4a

The amino acid sequences of heavy, light chains, HCDRs and LCDRs of an exemplary humanized C5aR1 Site II antibodies

| | |
|---|---|
| Heavy chain of c2139 | QVQLVQSGAEVKKPGASVKVSCKASGYTFTNYWMHWV RQAPGQGLEWMGYLNPSSGYTKYAQKFQGRVTMTRDT STSTVYMELSSLRSEDTAVYYCTRSGGDNYGNPYYFD RWGQGTTVTVSSASTKGPSVFPLAPCSRSTSESTAAL GCLVKDYFPEPVTVSWNSGALTSGVHTFPAVLQSSGL YSLSSVVTVPSSSLGTKTYTCNVDHKPSNTKVDKRVE SKYGPPCPPCPAPEFLGGPSVFLFPPKPKDTLMISRT PEVTCVVVDVSQEDPEVQFNWYVDGVEVHNAKTKPRE EQFNSTYRVVSVLTVLHQDWLNGKEYKCKVSNKGPS SIEXTISKAKGQPREPQVYTLPPSQEEMTKNQVSLTC LVKGFYPSDIAVEWESNGQPENNYKTTPPVLDSDGSF FLY3RLTVDKSRWQEGNVFSCSVMHEALHNHYTQKSL SLSLGK (SEQ ID NO: 4) |

TABLE 4a-continued

The amino acid sequences of heavy, light chains, HCDRs and LCDRs of an exemplary humanized C5aR1 Site II antibodies

| | |
|---|---|
| Light chain of c2139 | DVQMTQSPSSLSASVGDRVTITCRASQSIVHSNGNTY LHWYQQKPGKAPKFLIYKVSNRFSGVPSRFSGSGSGT DFTLTISSLQPEDFATYYCAQYTLVPLTFGQGTKLEI KRTVAAPSVFIFPPSDEQLKSGTASVVCLLNNFYPRE AKVQWKVDNALQSGNSQESVTEQDSKDSTYSLSSTLT LSKADYEKHKVYACEVTHQGLSSPVTKSFNRGEC (SEQ ID NO: 5) |
| HCDR1 of c2139 | NYWMH (SEQ ID NO: 6) |
| HCDR2 of c2139 | YLNPSSGYTKYAQKFQG (SEQ ID NO: 7) |
| HCDR3 of c2139 | SGGDNYGNPYYFDR (SEQ ID NO: 8) |
| LCDR1 of c2139 | RASQSIVHSNGNTYLH (SEQ ID NO: 9) |
| LCDR2 of c2139 | KVSNRFS (SEQ ID NO: 10) |
| LCDR3 of c2139 | AQYTLVPLT (SEQ ID NO: 11) |
| Heavy chain of c2137 | QVQLVQSGAEVKKPGASVKVSCKASGYTFTNYWMHWV RQAPGQGLEWMGYLNPSSGYTKYAQKFQGRVTMTRDT STSTVYMELSSLRSEDTAVYYCTRSGGDNYGNPYYFD RWGQGTTVTVSSASTKGPSVFPLAPCSRSTSESTAAL GCLVKDYFPEPVTVSWNSGALTSGVHTFPAVLQSSGL YSLSSVVTVPSSSLGTKTYTCNVDHKPSNTKVDKRVE SKYGPPCPPCPAPEFLGGPSVFLFPPKPKDTLMISRT PEVTCVVVDVSQEDPEVQFNWYVDGVEVHNAKTKPRE EQFNSTYRVVSVLTVLHQDWLNGKEYKCKVSNKLGPS SIEKTISKAKGQPREPQVYTLPPSQEEMTKNQVSLTC LVKGFYPSDIAVEWESNGQPENNYKTTPPVLDSDGSF FLYSRLTVDKSRWQEGNVFSCSVMHEALHNHYTQKSL SLSLGK (SEQ ID NO: 4) |
| Light chain of c2137 | DVQMTQSPSSLSASVGDRVTITCRASQSIVHSNGNTY LHWYQQKPGKAPKFLIYKVSNRFSGVPSRFSGSGSGT DFTLTISSLQPEDFATYYCAQSTLVPLTFGQGTKLEI KRTVAAPSVFIFPPSDEQLKSGTASVVCLLNNFYPRE AKVQWKVDNALQSGNSQESVTEQDSKDSTYSLSSTLT LSKADYEKHKVYACEVTHQGLSSPVTKSFNRGEC (SEQ ID NO: 75) |

In some embodiments, the HCVR and LCVR of exemplary Site II binding antibodies, such as for example c2139, are further linked to an Fc domain. The Fc domain further comprises a CH2 and CH3 domain, linked to each other via a linker. However, instant disclosure also encompasses site II binding biologic molecules, devoid of an Fc domain.

In some embodiments, the exemplary site I or site II binding antibody against C5aR1, binds C5aR1 with a dissociation constant (Kd) of 10 pM to 50 nM, thereby inhibiting the association of C5aR1 with C5a, thereby antagonizing the C5a/C5aR1 axis pathway.

In some embodiments, the effective inhibition of the C5a/C5aR1 antibody is measured by inhibition of Gα signaling, inhibition of neutrophil chemotaxis, inhibition of CD11b expression and inhibition of calcium signaling.

In some embodiments, the exemplary site I or site II binding antibody against C5aR1, does not, or does not substantially bind to C5aR2, or other GPCRs.

In some embodiments, the exemplary site I or site II binding antibody against C5aR1 is capable of binding to human neutrophils.

In some embodiments, the exemplary site I or site II binding antibody against C5aR1 inhibits β-arrestin signaling.

In some embodiments, the exemplary site I or site II binding antibody against C5aR1 inhibits ROS production in neutrophils.

In some embodiments, the exemplary site I or site II binding antibody against C5aR1 is internalized. In some embodiments, internalization takes at least 6 hours. In some embodiments, the internalization takes at least 12 hours. In some embodiments, internalization takes less than 6 hours.

Design of Multispecific C5aR1 Antagonists

In some aspects the antibodies presented herein are multispecific antibodies. In an embodiment, the multispecific antibody molecule is a multiparatopic antibody molecule, e.g., it comprises a plurality of immunoglobulin variable region sequences, wherein a first immunoglobulin variable region sequence of the plurality has binding specificity for a first epitope and a second immunoglobulin variable region sequence of the plurality has binding specificity for a second epitope. In an embodiment, the first and second epitopes are on the same antigen, e.g., the same protein (or subunit of a multimeric protein). A bispecific or biparatopic antibody has specificity for no more than two antigens or epitopes. A bispecific or biparatopic antibody molecule is typically characterized by a first immunoglobulin variable region sequence which has binding specificity for a first epitope and a second immunoglobulin variable region sequence that has binding specificity for a second epitope. In an embodiment, a bispecific or biparatopic antibody molecule comprises a half antibody, or fragment thereof, having binding specificity for a first epitope and a half antibody, or fragment thereof, having binding specificity for a second epitope. In an embodiment, the first and second epitopes are on the same antigen, e.g., the same protein (or subunit of a multimeric protein). In an embodiment the first epitope is located on C5aR1 (e.g., Site I, e.g., comprising an N-terminal region as described herein) and the second epitope is located on C5aR1 (e.g., Site II, e.g., comprising an ECL2, as described herein). In an embodiment, the antibody is a biparatopic antibody that binds to Site I (SEQ ID NO: 1 or SEQ ID NO: 2) and Site II (SEQ ID NO: 3) of C5aR1.

In some aspects, the biparatopic antibody comprises a pair of VH and VL from Table 2a. In some embodiments, the biparatopic antibody comprises a pair of VH and VL from Table 3. In some embodiments, the biparatopic antibody comprises a pair of VH and VL from Table 2a and a pair of VH and VL from Table 3. In some aspects, the biparatopic antibody comprises a VH selected from an amino acid sequence of SEQ ID NO: 14 or SEQ ID NO: 50-59 or has at least 85%, 90%, 95%, 99% or 100% identity with the amino acid sequence of any of SEQ ID NO: 14 or SEQ ID NO: 50-59 and a VL selected from an amino acid sequence of SEQ ID NO: 15 or SEQ ID NO: 25 or SEQ ID NO: 60-68 or has at least 85%, 90%, 95%, 99% or 100% identity with the amino acid sequence of any of SEQ ID NO: 15 or SEQ ID NO: 25 or SEQ ID NO: 60-68. In some aspects, the biparatopic antibody comprises a VH selected from any of amino acid sequence of SEQ ID NO: 16 or SEQ ID NO: 39-43 or an amino acid sequence 80%, 85%, 90%, 95%, 98%, 99% identical to SEQ ID NO: 16 or SEQ ID NO: 39-43 and a VL selected from any of amino acid sequence of SEQ ID NO: 17 or SEQ ID NO: 44-49 or an amino acid sequence 80%, 85%, 90%, 95%, 98%, 99% identical to SEQ ID NO: 17 or SEQ ID NO: 44-49.

In some embodiments, one epitope of the biparatopic antibody described herein are designed to target sulfated N-terminal peptide or Site I of C5aR1, defined by SEQ ID NO: 1 or SEQ ID NO: 2. In some embodiments, the Site I residues targeted by the antibody molecules described herein, are sulfated. In some embodiments one or more of amino acid residues T8 (threonine 8), D10 (aspartate 10), Y11 (tyrosine 11), Y14 (tyrosine 14) and/or D15 (aspartate 15) are critical Site I epitope contact points. In some embodiments, the sulfation at Y11 and/or Y14 are critical for binding of Site I antibody molecules described herein. In some embodiments, core epitope spans 12 amino acids from T7 to D18 of SEQ ID NO: 38, for binding of Site I antibody molecules described herein. In some embodiments, core epitope spans amino acids from T8 to D18 of SEQ ID NO: 38, for binding of Site I antibody molecules described herein.

In some embodiments, the antibody molecules described herein are designed to target Site II, defined by amino acids of SEQ ID NO: 3. In some embodiments amino acid encompassing R175 to G189 of SEQ ID NO: 38 are core epitopes for binding of Site II antibody molecules described herein. In some embodiments, amino acid encompassing E180-P183 of SEQ ID NO: 38 are core epitopes for binding of Site II antibody molecules described herein. In some embodiments, amino acid encompassing E180-P184 of SEQ ID NO: 38 are core epitopes for binding of Site II antibody molecules described herein. In some embodiments, amino acid encompassing E178-P183 of SEQ ID NO: 38 are core epitopes for binding of Site II antibody molecules described herein. In some embodiments, one or more of the residues R35, H101, V176, V177, R178, E179, E180, Y181, F182, P183 P184, K185, L187, D191, S193, H194, E266, P267, S268, F272, L273 and/or K276 of C5aR1 (SEQ ID NO: 38) are important for binding of Site II antibodies described herein. In some embodiments one or more of the residues E180, Y181, F182, and/or P183 of SEQ ID NO: 38 are critical epitopes for binding of Site II antibodies described herein. In one embodiment, the amino acid residue W102 of SEQ ID NO: 38 is critical for binding of Site II antibodies described herein.

In some embodiments, the biparatopic antibody presented in this disclosure comprises a Fab-Fc and a single chain variable fragment (scFv), wherein the Fc is linked to the scFv via a linker. In some embodiments, the Fab domain binds site I and the scFv binds site II.

In some embodiments, the biparatopic antibody presented in this disclosure comprises a Fab-Fc and a single chain variable fragment (scFv). In some embodiments, the Fab domain binds site II and the scFv binds site I, wherein the Fc is linked to the scFv via a linker.

Figure 3B:
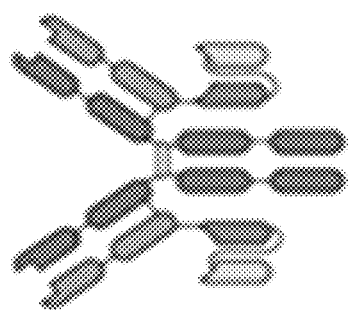
FIG. 3B is a schematic diagram of an exemplary biparatopic antibody comprising a scFv linked to the light chain of a Fab as described herein.
Figure 3A:
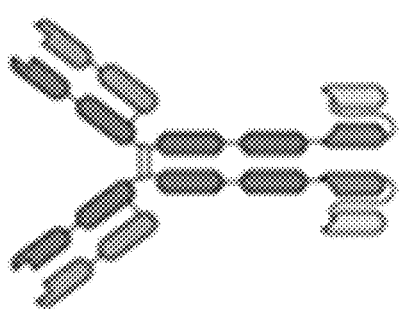
FIG. 3A is an exemplary schematic diagram of an exemplary biparatopic antibody comprising a scFv linked to heavy chain Fc domain of a Fab described herein.

In some embodiments, the biparatopic antibody presented in this disclosure is a tetravalent antibody comprising a heavy chain, wherein the heavy chain comprises a VH-Fc linked to scFV domain, as shown in FIG. 3A.

In some embodiments, the site II binding arm of the biparatopic antibody comprises a glycine or alanine at position 89 of the VH. In some embodiments the site II binding arm of the biparatopic antibody comprise tyrosine at position 91. In some embodiments, the site II binding arm of the biparatopic antibody comprises tyrosine at position 91 and glycine or alanine at position 89 of the VH.

In some embodiments, the biparatopic antibody presented in this disclosure is tetravalent antibody comprising a light chain, wherein the light chain comprises a VL linked to scFv domain, as shown in FIG. 3B.

In some embodiments, the biparatopic antibody is a bispecific antibody with two arms single chain Fab-Fc design, comprising "knobs-in-holes" (KiH) mutations in CH3 domain, to assemble two half antibodies (common Fc heterodimer and unique VH-CH and VL-CL domains). In some embodiments, the KiH mutations comprise, a T366Y mutation in one CH3 domain can be used to create a knob while an Y407T mutation in the other CH3 domain to create a hole. In some embodiments, F405A mutation in one CH3 domain can be used to create a knob while a T394W mutation in the other CH3 domain to create a hole. In some embodiments, a T366W mutation in one CH3 domain can be used to create a knob while an Y407A mutation in the other CH3 domain to create a hole. In some embodiments, the biparatopic scFv-Fc molecules can be produced with knob-hole technology (e.g., including hole mutations: Y349C, T366S, L368A, Y407V; knob mutations: S354C, T366W).

In some embodiments, the biparatopic antibody comprises antibody formats described in Table 4b.

TABLE 4b

Formats of biparatopic antibodies (Site II) Fab-IgG-scFv (Site I)
(Site II) Fab-IgG-linker-VL(Site I)-linker-VH (Site I)
(Site II) Fab-IgG-linker-VH(Site I)-linker-VL (Site I)
(Site I) Fab-IgG-scFv (Site II)

In an embodiment, the biparatopic anti-C5aR1 antibody molecule comprises two heavy chain variable regions and two light chain variable regions. In an embodiment, the anti-C5aR1 antibody molecule comprises a Fab, F(ab')2, Fv, Fd, or a single chain Fv fragment (scFv).

In some embodiments, the Fc domain used in this application comprises or is derived from an IgG, IgM, IgE, Fc portion. In addition to the KiH mutations described above, the Fc domain comprises S228P mutation. In some embodiments, the S228P enhanced the homogeneity of the antibody. In some embodiments, the Fc domain comprises or is derived from an IgG Fc domain. In some embodiments, the IgG Fc domain is IgG1, IgG2, IgG3 or IgG4 Fc domain. In some embodiments, the Fc domain is derived from or comprises an IgG4 Fc domain. In some embodiments, the Fc domain is derived from or comprises an IgG4 Fc domain with S228P mutation. In some embodiments, the Fc domain is derived from or comprises an IgG1 Fc domain. In some embodiments, the Fc domain is derived from or comprises an IgG1 Fc domain with S228P mutation.

In some embodiments, the biparatopic antibody comprises two scFv regions linked to each other via a linker, wherein, the first scFv binds site I and second scFv binds site II.

In some embodiments, the Fab-Fc-linker-scFv biparatopic antibody is a tetravalent antibody comprising a heavy chain sequence of SEQ ID NO: 12 and light chain sequence of SEQ ID NO: 13 or any sequences that are at least 60%, 65%, 70%, 75%, 80%, 85%, 90%, 95% or 99% identical to SEQ ID NO: 12 and SEQ ID NO 13.

In some embodiments, the Fab-Fc-linker-scFv biparatopic antibody is a tetravalent antibody comprising a heavy chain sequence of SEQ ID NO: 12 and light chain sequence of SEQ ID NO: 76 or any sequences that are at least 60%, 65%, 70%, 75%, 80%, 85%, 90%, 95% or 99% identical to SEQ ID NO: 12 and SEQ ID NO 76.

Table 4c presents the sequences of heavy and light chain sequences of the biparatopic antibody.

TABLE 4c

The amino acid sequences of heavy and light chains of humanized C5aR1 biparatopic antibody

| | |
|---|---|
| Heavy chain of c2137-e1711 | QVQLVQSGAEVKKPGASVKVSCKASGYTFTNYWMH WVRQAPGQGLEWMGYLNPSSGYTKYAQKFQGRVTM TRDTSTSTVYMELSSLRSEDTAVYYCTRSGGDNYG NPYYFDRWGQGTTVTVSSASTKGPSVFPLAPCSRS TSESTAALGCLVKDYFPEPVTVSWNSGALTSGVHT FPAVLQSSGLYSLSSVVTVPSSSLGTKTYTCNVDH KPSNTKVDKRVESKYGPPCPPCPAPEFLGGPSVFL FPPKPKDTLMISRTPEVTCVVVDVSQEDPEVQFNW YVDGVEVHNAKTKPREEQFNSTYRVVSVLTVLHQD WLNGKEYKCKVSNKGLPSSIEKTISKAKGQPREPQ VYTLPPSQEEMTKNQVSLTCLVKGFYPSDIAVEWE SNGQPENNYKTTPPVLDSDGSFFLYSRLTVDKSRW QEGNVFSCSVMHEALHNHYTQKSLSLSLGGGGGSE IVLTQSPATLSLSPGERATLSCRSSQSLVHSNGNT YLNWYQQKPGQAPRLLIYKVSNRLSGIPARFSGSG SGTDFTLTISSLEPEDFAVYYCSQSTHVPYTFGCG TKLEIKGGGSGGGGSGGGGSGGGGSEVQLVESGG GLIQPGGSLRLSCAASGFTFNAYAMSWVRQAPGKC LEWVSSISTGGNTYYADSVKGRFTISRDNSKNTLY LQMNSLRAEDTAVYYCTRGYQRFSGFAYWGQGTLV TVSS (SEQ ID NO: 12) |
| Light chain of c2137-e1711 | DVQMTQSPSSLSASVGDRVTITCRASQSIVHSNGN TYLHWYQQKPGKAPKFLIYKVSNRFSGVPSRFSGS GSGTDFTLTISSLQPEDFATYYCAQSTLVPLTFGQ GTKLEIKRTVAAPSVFIFPPSDEQLKSGTASVVCL LNNFYPREAKVQWKVDNALQSGNSQESVTEQDSKD STYSLSSTLTLSKADYEKHKVYACEVTHQGLSSPV TKSFNRGEC (SEQ ID NO: 13) |
| Heavy chain of c2139-e1711 | QVQLVQSGAEVKKPGASVKVSCKASGYTFTNYWMH WVRQAPGQGLEWMGYLNPSSGYTKYAQKFQGRVTM TRDTSTSTVYMELSSLRSEDTAVYYCTRSGGDNYG NPYYFDRWGQGTTVTVSSASTKGPSVFPLAPCSRS TSESTAALGCLVKDYFPEPVTVSWNSGALTSGVHT FPAVLQSSGLYSLSSVVTVPSSSLGTKTYTCNVDH KPSNTKVDKRVESKYGPPCPPCPAPEFLGGPSVFL FPPKPKDTLMISRTPEVTCVVVDVSQEDPEVQFNW YVDGVEVHNAKTKPREEQFNSTYRVVSVLTVLHQD WLNGKEYKCKVSNKGLPSSIEKTISKAKGQPREPQ VYTLPPSQEEMTKNQVSLTCLVKGFYPSDIAVEWE SNGQPENNYKTTPPVLDSDGSFFLYSRLTVDKSRW QEGNVFSCSVMHEALHNHYTQKSLSLSLGGGGGSE IVLTQSPATLSLSPGERATLSCRSSQSLVHSNGNT YLNWYQQKPGQAPRLLIYKVSNRLSGIPARFSGSG SGTDFTLTISSLEPEDFAVYYCSQSTHVPYTFGCG TKLEIKGGGSGGGGSGGGGSGGGGSEVQLVESGG GLIQPGGSLRLSCAASGFTFNAYAMSWVRQAPGKC LEWVSSISTGGNTYYADSVKGRFTISRDNSKNTLY LQMNSLRAEDTAVYYCTRGYQRFSGFAYWGQGTLV TVSS (SEQ ID NO: 12) |
| Light chain of c2139-e1711 | DVQMTQSPSSLSASVGDRVTITCRASQSIVHSNGN TYLHWYQQKPGKAPKFLIYKVSNRFSGVPSRFSGS GSGTDFTLTISSLQPEDFATYYCAQYTLVPLTFGQ GTKLEIKRTVAAPSVFIFPPSDEQLKSGTASVVCL LNNFYPREAKVQWKVDNALQSGNSQESVTEQDSKD STYSLSSTLTLSKADYEKHKVYACEVTHQGLSSPV TKSFNRGEC (SEQ ID NO: 76) |

In some embodiments, the biparatopic has two variable regions—variable region 1 and variable region 2. Each variable region comprises a variable heavy chain and a variable light chain.

In an exemplary embodiment, the variable region 1 comprises variable heavy chain 1 (VH1) comprising SEQ ID NO: 14 and variable light chain 1 (VL1) comprising SEQ ID NO: 15. In some embodiments the variable region 1 comprises a sequence 85%, 90%, 95%, 96%, 97%, 98%, or 99% identical to sequence of VH1, comprising amino acid sequence of SEQ ID NO: 14. In some embodiments the variable region 1 comprises a sequence 85%, 90%, 95%, 96%, 97%, 98%, or 99% identical to sequence of VL1, comprising amino acid sequence of SEQ ID NO: 15.

In some exemplary embodiments the variable region 2 comprises a variable heavy chain 2 (VH2) and a variable light chain 2 (VL2), comprising the amino acid sequence of SEQ ID NO: 16 and SEQ ID NO: 17, respectively. In some embodiments the variable region 2 comprises a sequence 85%, 90%, 95%, 96%, 97%, 98%, or 99% identical to sequence of VH2, comprising amino acid sequence of SEQ ID NO: 16. In some embodiments the variable region 2 comprises a sequence 85%, 90%, 95%, 96%, 97%, 98%, or 99% identical to sequence of VL2, comprising amino acid sequence of SEQ ID NO: 17.

In some exemplary embodiments, the biparatopic antibody comprising VH1 of SEQ ID NO: 14, VL1 of SEQ ID NO: 15, VH2 of SEQ ID NO: 16 and VL2 of SEQ ID NO: 17 is called c2137-e1711.

In some exemplary embodiments, the VH1 comprises three HCDRs, HCDR1, HCDR2 and HCDR3, comprising amino acid sequences of SEQ ID NO: 6, SEQ ID NO: 7 and SEQ ID NO: 8, or comprises a sequence that differs by no more than 5, 4, 3, 2 or 1 amino acids from amino acids of SEQ ID Nos: 6, 7 and/or 8.

In some exemplary embodiments, the VH2 comprises three HCDRs, HCDR4, HCDR5 and HCDR6, comprising amino acid sequences of SEQ ID NO: 18, SEQ ID NO: 19 and SEQ ID NO: 20, or comprises a sequence that differs by no more than 5, 4, 3, 2 or 1 amino acids from amino acids of SEQ ID Nos: 18, 19 and/or 20.

In some exemplary embodiments, the VL1 comprises three LCDRs, LCDR1, LCDR2 and LCDR3, comprising amino acid sequences of SEQ ID NO: 9, SEQ ID NO: 10 and SEQ ID NO: 21, or comprises a sequence that differs by no more than 5, 4, 3, 2 or 1 amino acids from amino acids of SEQ ID Nos: 9, 10 and/or 21.

In some exemplary embodiments, the VL2 comprises three LCDRs, LCDR4, LCDR5 and LCDR6, comprising amino acid sequences of SEQ ID NO: 22, SEQ ID NO: 23 and SEQ ID NO: 24, or comprises a sequence that differs by no more than 5, 4, 3, 2 or 1 amino acids from amino acids of SEQ ID Nos: 22, 23 and/or 24. Table 5 presents the amino acid sequences of VH1, VH2, VL1, VL2, HCDR1, HCDR2, HCDR3, HCDR4, HCDR5, HCDR6, LCDR1, LCDR2, LCDR3, LCDR4, LCDR5 and LCDR6.

In some exemplary embodiments, the HCDR1, HCDR2, HCDR3, HCDR4, HCDR5, HCDR6, LCDR1, LCDR2, LCDR3, LCDR4, LCDR5 and LCDR6 comprise an amino acid sequence that differs by no more than 5 amino acid residues from, the amino acid sequence of SEQ ID NOs: 16-21.

TABLE 5

The amino acid sequences of humanized C5aR1biparatopic antibody (c2137-e1711) variable domains and CDRs

| | |
|---|---|
| HCDR1 | NYWMH (SEQ ID NO: 6) |
| HCDR2 | YLNPSSGYTKYAQKFQG (SEQ ID NO: 7) |
| HCDR3 | SGGDNYGNPYYFDR (SEQ ID NO: 8) |
| HCDR4 | AYAMS (SEQ ID NO: 18) |
| HCDR5 | SISTGGNTYYADSVKG (SEQ ID NO: 19) |
| HCDR6 | GYQRFSGFAY (SEQ ID NO: 20) |

TABLE 5-continued

The amino acid sequences of humanized C5aR1biparatopic antibody (c2137-e1711) variable domains and CDRs

| | |
|---|---|
| LCDR1 | RASQSIVHSNGNTYLH (SEQ ID NO: 9) |
| LCDR2 | KVSNRFS (SEQ ID NO: 10) |
| LCDR3 | AQSTLVPLT (SEQ ID NO: 21) |
| LCDR4 | RSSQSLVHSNGNTYLN (SEQ ID NO: 22) |
| LCDR5 | KVSNRLS (SEQ ID NO: 23) |
| LCDR6 | SQSTHVPYT (SEQ ID NO: 24) |

In some exemplary embodiments a variable region of the biparatopic antibody comprises a variable region 1, wherein the variable region 1 comprises a VH1 and a VL1, comprising the amino acid sequence of SEQ ID NO: 16 and SEQ ID NO: 17, respectively. In some embodiments the variable region 1 comprises a sequence 85%, 90%, 95%, 96%, 97%, 98%, or 99% identical to sequence of VH1, comprising amino acid sequence of SEQ ID NO: 16. In some embodiments the variable region 1 comprises a sequence 85%, 90%, 95%, 96%, 97%, 98%, or 99% identical to sequence of VL1, comprising amino acid sequence of SEQ ID NO: 17.

In some exemplary embodiments the variable region of the biparatopic antibody comprises a variable region 2, wherein the variable region 2 comprises a VH2 comprising SEQ ID NO: 14 and a VL2 comprising SEQ ID NO: 15. In some embodiments the variable region 2 comprises a sequence 85%, 90%, 95%, 96%, 97%, 98%, or 99% identical to sequence of VH2, comprising amino acid sequence of SEQ ID NO: 14. In some embodiments the variable region 2 comprises a sequence 85%, 90%, 95%, 96%, 97%, 98%, or 99% identical to sequence of VL2, comprising amino acid sequence of SEQ ID NO: 15.

In some exemplary embodiments, the VH1 comprises three HCDRs, HCDR1, HCDR2 and HCDR3, comprising amino acid sequences of SEQ ID NO: 18, SEQ ID NO: 19 and SEQ ID NO: 20, or comprises a sequence that differs by no more than 5, 4, 3, 2 or 1 amino acids from amino acids of SEQ ID Nos: 18, 19 and/or 20.

In some exemplary embodiments, the VH2 comprises three HCDRs, HCDR4, HCDR5 and HCDR6, comprising amino acid sequences of SEQ ID NO: 6, SEQ ID NO: 7 and SEQ ID NO: 8, or comprises a sequence that differs by no more than 5, 4, 3, 2 or 1 amino acids from amino acids of SEQ ID Nos: 6, 7 and/or 8.

In some exemplary embodiments, the VL1 comprises three LCDRs, LCDR1, LCDR2 and LCDR3, comprising amino acid sequences of SEQ ID NO: 22, SEQ ID NO: 23 and SEQ ID NO: 24, or comprises a sequence that differs by no more than 5, 4, 3, 2 or 1 amino acids from amino acids of SEQ ID Nos: 22, 23 and/or 24.

In some exemplary embodiments, the VL2 comprises three LCDRs, LCDR4, LCDR5 and LCDR6, comprising amino acid sequences of SEQ ID NO: 9, SEQ ID NO: 10 and SEQ ID NO: 21, or comprises a sequence that differs by no more than 5, 4, 3, 2 or 1 amino acids from amino acids of SEQ ID NOs: 9, 10 and/or 21. Table 5 presents the amino acid sequences of VH1, VH2, VL1, VL2, HCDR1, HCDR2, HCDR3, HCDR4, HCDR5, HCDR6, LCDR1, LCDR2, LCDR3, LCDR4, LCDR5 and LCDR6.

In some exemplary embodiments, the HCDR1, HCDR2, HCDR3, HCDR4, HCDR5, HCDR6, LCDR1, LCDR2, LCDR3, LCDR4, LCDR5 and LCDR6 comprise an amino acid sequence that differs by no more than 5 amino acid residues from, the amino acid sequence of SEQ ID NOs: 16-21.

In some exemplary embodiments a variable region of the biparatopic antibody comprises a variable region 1, wherein the variable region 1 comprises a VH1 and a VL1, comprising the amino acid sequence of SEQ ID NO: 14 and SEQ ID NO: 25, respectively. In some embodiments the variable region 1 comprises a sequence 85%, 90%, 95%, 96%, 97%, 98%, or 99% identical to sequence of VH1, comprising amino acid sequence of SEQ ID NO: 14. In some embodiments the variable region 1 comprises a sequence 85%, 90%, 95%, 96%, 97%, 98%, or 99% identical to sequence of VL1, comprising amino acid sequence of SEQ ID NO: 25.

In some exemplary embodiments the variable region of the biparatopic antibody comprises a variable region 2, wherein the variable region 2 comprises a VH2 and a VL2, comprising the amino acid sequence of SEQ ID NO: 16 and SEQ ID NO: 17, respectively. In some embodiments the variable region 2 comprises a sequence 85%, 90%, 95%, 96%, 97%, 98%, or 99% identical to sequence of VH2, comprising amino acid sequence of SEQ ID NO: 16. In some embodiments the variable region 2 comprises a sequence 85%, 90%, 95%, 96%, 97%, 98%, or 99% identical to sequence of VL2, comprising amino acid sequence of SEQ ID NO: 17.

In some exemplary embodiments, the biparatopic antibody comprising VH1 of SEQ ID NO: 14, VL1 of SEQ ID NO: 25, VH2 of SEQ ID NO: 16 and VL2 of SEQ ID NO: 17 is called c2139-e1711.

In some exemplary embodiments, the exemplary biparatopic antibody binding C5aR1 binds one or more of amino acid residues T8 (threonine 8), D10 (aspartate 10), Y11 (tyrosine 11), Y14 (tyrosine 14) and/or D15 (aspartate 15) in SEQ ID NO: 38.

In some exemplary embodiments the exemplary biparatopic antibody binding C5aR1 binds to amino acid residues R175-G189 in SEQ ID NO: 38.

In some exemplary embodiments the exemplary biparatopic antibody binding C5aR1 binds to amino acid residues E180-P183 in SEQ ID NO: 38.

In some exemplary embodiments the exemplary biparatopic antibody binding C5aR1 binds to amino acid residues E180-P184 in SEQ ID NO: 38.

In some exemplary embodiments the exemplary biparatopic antibody binding C5aR1 binds to amino acid residues E178-P183 in SEQ ID NO: 38.

In some embodiments, the exemplary biparatopic antibody against C5aR1, inhibits β-arrestin signaling.

In some embodiments, the exemplary biparatopic antibody against C5aR1 inhibits ROS production in neutrophils.

In some embodiments, the exemplary biparatopic antibody against C5aR1 is internalized. In some embodiments, internalization takes at least 6 hours. In some embodiments, the internalization takes at least 12 hours. In some embodiments, internalization takes less than 6 hours.

In some exemplary embodiments, the mono-specific and biparatopic antibodies can be modified or mutated to enhance the thermal stability of the antibody. The thermal stability of the antibodies can be evaluated by determining the aggregation onset temperature. One of the ways to increase antibody stability is to raise the thermal transition midpoint (Tm) as measured by differential scanning calorimetry (DSC). In general, the protein Tm is correlated with its stability and inversely correlated with its susceptibility to unfolding and denaturation in solution and the degradation processes that depend on the tendency of the protein to unfold. A number of studies have found correlation between the ranking of the physical stability of formulations measured as thermal stability by DSC and physical stability measured by other methods (Maa et al. (1996) Int. J. Pharm. 140: 155-68; Remmele et al. (1997) Pharm. Res. 15: 200-8; Gupta et al. (2003) AAPS PharmSci. 5E8: 2003; Bedu-Addo et al. (2004) Pharm. Res. 21: 1353-61; Zhang et al. (2004) J. Pharm. Sci. 93: 3076-89). Formulation studies suggest that a Fab Tm has implication for long-term physical stability of a corresponding mAb.

In some exemplary embodiments, strategic introduction of disulfide bonds can stabilize monomeric and multisubunit proteins, play a role in enhancing thermal stability of antibodies.

In some exemplary embodiments, strategic introduction of 7-stacking interactions with aromatic amino acids (AAs) like tryptophan (TRP), tyrosine (TYR), phenylalanine (PHE) and histidine (HIS), play a role in enhancing thermal stability of antibodies.

In some embodiments, strategic introduction of salt bridges occurring between amino acid side-chains with opposite positive or negative full-electron charges, namely, (at neutral pH) Glu or Asp vs Arg or Lys, enhance the stability of proteins, particularly antibodies.

In some exemplary embodiments, the monospecific antibody or the biparatopic antibody comprise one or more thermal stability enhancing modifications. In some embodiments, the thermal stability enhancing modification is introduction of a cysteine residue. In some embodiments, the biparatopic antibody comprises cysteine at position 559 of SEQ ID NO: 12 and at position 630 of SEQ ID NO: 12, to enhance the thermal stability.

In some embodiments, the Tm of exemplary biparatopic antibodies is greater than 65° C. In some embodiments, the Tm of exemplary biparatopic antibodies is greater than 60° C. the Tm of exemplary biparatopic antibodies is greater than 55° C. In some embodiments, the Tm of exemplary biparatopic antibodies is greater than 50° C.

Some types of biparatopic antibody molecules are produced by crosslinking Site I and Site II binding domains or antigen binding fragments to create bispecific antibodies. Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

In some embodiments, peptide linkers are used to link scFv or single chain antibodies to the Fc domain of the Fab. Several Examples of suitable linkers include a single glycine (G) residue; a diglycine peptide (GG); a tripeptide (GGG); a peptide with four glycine residues (GGGG; SEQ ID NO: 26); a peptide with five glycine residues (GGGGG; SEQ ID NO: 27); a peptide with six glycine residues (GGGGGG; SEQ ID NO: 28); a peptide with seven glycine residues (GGGGGGG; SEQ ID NO: 29); a peptide with eight glycine residues (GGGGGGGG; SEQ ID NO: 30). Other combinations of amino acid residues may be used such as the peptide GGGGS (SEQ ID NO: 31), the peptide GGGGSGGGGS (SEQ ID NO: 32), the peptide GGGGSGGGGSGGGGS (SEQ ID NO: 33), the peptide GGGGSGGGGSGGGGSGGGGS (SEQ ID NO: 34), the peptide GGSGSSGSGG (SEQ ID NO: 35), QRIEG (SEQ ID NO: 36) and the peptide GQPKAAP (SEQ ID NO: 37).

Other suitable linkers include a single Ser, and Val residue; the dipeptide RTQP, SS, TK, SL, TKGPS, TVAAP, QPKAA. The examples listed above are not intended to limit the scope of the disclosure in any way, and linkers comprising randomly selected amino acids selected from the group consisting of valine, leucine, isoleucine, serine, threonine, lysine, arginine, histidine, aspartate, glutamate, asparagine, glutamine, glycine, and proline have been shown to be suitable in the binding proteins. For additional descriptions of linker sequences, see, e.g., WO2012135345.

The identity and sequence of amino acid residues in the linker may vary depending on the type of secondary structural element necessary to achieve in the linker. For example, glycine, serine, and alanine are best for linkers having maximum flexibility. Some combination of glycine, proline, threonine, and serine are useful if a more rigid and extended linker is necessary. Any amino acid residue may be considered as a linker in combination with other amino acid residues to construct larger peptide linkers as necessary depending on the desired properties.

Design of Fc Variants

In some aspects the monospecific and multispecific (including bispecific or biparatopic) C5aR1 antibodies presented herein comprise variations or mutations in the Fc region. In some embodiments, the Fc variants or mutants reduce the ability to undergo Fab arm exchange for the production of stable IgG1 or IgG4 bispecific antibodies. (See Stubenrauch et al., Drug Metabolism and Disposition 38, 84-91 (2010)). In a particular embodiment the Fc domain is an IgG1 Fc domain. In another embodiment the Fc domain is an IgG4 Fc domain. In a more specific embodiment, the Fc domain is an IgG4 Fc domain comprising an amino acid substitution at position S228 (Kabat numbering), particularly the amino acid substitution S228P.

In some embodiments, the Fc region comprises a human IgG4 Fc region comprising one or more mutations selected from the group consisting of S228P, L234V, L235A, G237A, D265G, A330S, P331S, L328R, H268A and N297Q mutations (as designated according to Kabat, et al. (1991)). In some instances, a human IgG4 Fc variant has up to 10, 9, 8, 7, 6, 5, 4, 3, 2 or 1 mutation(s) in total as compared to wild-type human IgG4 sequence. In one embodiment, the Fc region comprises F234V, L235E, and D265G mutations. In some embodiments, the Fc region comprises F234V, L235E, D265G, and S228P mutations.

In some embodiments, the Fc variant exhibits reduced binding to an Fc receptor of the subject compared to the wild-type human IgG Fc region. In some embodiments, the Fc variant exhibits ablated binding to an Fc receptor of the subject compared to the wild-type human IgG Fc region. In some embodiments, the Fc variant exhibits a reduction of phagocytosis compared to the wild-type human IgG Fc region. In some embodiments, the Fc variant exhibits ablated phagocytosis compared to the wild-type human IgG Fc region.

Antibody-dependent cell-mediated cytotoxicity, which is also referred to herein as ADCC, refers to a form of cytotoxicity in which secreted Ig bound onto Fc receptors (FcRs) present on certain cytotoxic cells (e.g., Natural Killer (NK) cells and neutrophils) enabling these cytotoxic effector cells to bind specifically to an antigen-bearing target cell and subsequently kill the target cell. Antibody-dependent cell-mediated phagocytosis, which is also referred to herein as ADCP, refers to a form of cytotoxicity in which secreted Ig bound onto Fc receptors (FcRs) present on certain phagocytic cells (e.g., macrophages) enabling these phagocytic effector cells to bind specifically to an antigen-bearing target cell and subsequently engulf and digest the target cell. Ligand-specific high-affinity IgG antibodies directed to the surface of target cells can stimulate the cytotoxic or phagocytic cells and can be used for such killing. In some embodiments, polypeptide constructs comprising an Fc variant as described herein exhibit reduced ADCC or ADCP as compared to a polypeptide construct comprising a wild-type Fc region. In some embodiments, polypeptide constructs comprising an Fc variant as described herein exhibit at least a 5%, 10%, 15%, 20%, 30%, 40%, 50%, 60%, 70%, 80%, 90% or greater reduction in ADCC or ADCP compared to a polypeptide construct comprising a wild-type Fc region. In some embodiments, antibodies comprising an Fc variant as described herein exhibit ablated ADCC or ADCP as compared to a polypeptide construct comprising a wild-type Fc region.

In some embodiments, the Fc variant exhibits reduced binding to an Fc receptor of the subject compared to the wild-type human IgG Fc region. In some embodiments, the Fc variant exhibits ablated binding to an Fc receptor of the subject compared to the wild-type human IgG Fc region. In some embodiments, the Fc variant exhibits a reduction of phagocytosis compared to the wild-type human IgG Fc region. In some embodiments, the Fc variant exhibits ablated phagocytosis compared to the wild-type human IgG Fc region.

Antibody-dependent cell-mediated cytotoxicity, which is also referred to herein as ADCC, refers to a form of cytotoxicity in which secreted Ig bound onto Fc receptors (FcRs) present on certain cytotoxic cells (e.g., Natural Killer (NK) cells and neutrophils) enabling these cytotoxic effector cells to bind specifically to an antigen-bearing target cell and subsequently kill the target cell. Antibody-dependent cell-mediated phagocytosis, which is also referred to herein as ADCP, refers to a form of cytotoxicity in which secreted Ig bound onto Fc receptors (FcRs for e.g., FcTRI, FcTRIIa, FcTRIIb, FcTRIIIa and/or FcTRIIIb) present on certain phagocytic cells (e.g., macrophages) enabling these phagocytic effector cells to bind specifically to an antigen-bearing target cell and subsequently engulf and digest the target cell. Ligand-specific high-affinity IgG antibodies directed to the surface of target cells can stimulate the cytotoxic or phagocytic cells and can be used for such killing. In some embodiments, polypeptide constructs comprising an Fc variant as described herein exhibit reduced ADCC or ADCP as compared to a polypeptide construct comprising a wild-type Fc region. In some embodiments, polypeptide constructs comprising an Fc variant as described herein exhibit at least a 5%, 10%, 15%, 20%, 30%, 40%, 50%, 60%, 70%, 80%, 90% or greater reduction in ADCC or ADCP compared to a polypeptide construct comprising a wild-type Fc region. In some embodiments, antibodies comprising an Fc variant as described herein exhibit ablated ADCC or ADCP as compared to a polypeptide construct comprising a wild-type Fc region.

An exemplary monospecific site II (SEQ ID NO: 3) binding antibodies, comprising Fc variants is also referred in this disclosure as c2139-$F_c$mod. An exemplary biparatopic antibody comprising Fc variants is also referred in this disclosure as c2137-e1711-Fcmod. The sequences of the monospecific and biparatopic antibody comprising the Fc variants are set forth in Table 6.

TABLE 6

Sequences of Fc modified exemplary
monospecific and biparatopic antibodies.

| Heavy chain | Light chain |
|---|---| c2139-F$_c$mod

| | |
|---|---|
| QVQLVQSGAEVKKPGASVKVSCKASGYTFTNYWMHWVR QAPGQGLEWMGYLNPSSGYTKYAQKFQGRVTMTRDTST STVYMELSSLRSEDTAVYYCTRSGGDNYGNPYYFDRWG QGTTVTVSSASTKGPSVFPLAPCSRSTSESTAALGCLV KDYFPEPVTVSWNSGALTSGVHTFPAVLQSSGLYSLSS VVTVPSSSLGTKTYTCNVDHKPSNTKVDKRVESKYGPP CPPCPAPEVEGGPSVFLFPPKPKDTLMISRTPEVTCVV VGVSQEDPEVQFNWYVDGVEVHNAKTKPREEQFNSTYR VVSVLTVLHQDWLNGKEYKCKVSNKGLPSSIEKTISKA KGQPREPQVYTLPPSQEEMTKNQVSLTCLVKGFYPSDI AVEWESNGQPENNYKTTPPVLDSDGSFFLYSRLTVDKS RWQEGNVFSCSVMHEALHNHYTQKSLSLSLGK (SEQ ID NO: 69) | DVQMTQSPSSLSASVGDRVTITCRASQSIVH SNGNTYLHWYQQKPGKAPKFLIYKVSNRFSG VPSRFSGSGSGTDFTLTISSLQPEDFATYYC AQYTLVPLTFGQGTKLEIKRTVAAPSVFIFP PSDEQLKSGTASVVCLLNNFYPREAKVQWKV DNALQSGNSQESVTEQDSKDSTYSLSSTLTL SKADYEKHKVYACEVTHQGLSSPVTKSFNRG EC (SEQ ID NO: 70) | c2137-F$_c$mod

| | |
|---|---|
| QVQLVQSGAEVKKPGASVKVSCKASGYTFTNYWMHWVR QAPGQGLEWMGYLNPSSGYTKYAQKFQGRVTMTRDTST STVYMELSSLRSEDTAVYYCTRSGGDNYGNPYYFDRWG QGTTVTVSSASTKGPSVFPLAPCSRSTSESTAALGCLV KDYFPEPVTVSWNSGALTSGVHTFPAVLQSSGLYSLSS VVTVPSSSLGTKTYTCNVDHKPSNTKVDKRVESKYGPP CPPCPAPEVEGGPSVFLFPPKPKDTLMISRTPEVTCVV VGVSQEDPEVQFNWYVDGVEVHNAKTKPREEQFNSTYR VVSVLTVLHQDWLNGKEYKCKVSNKGLPSSIEKTISKA KGQPREPQVYTLPPSQEEMTKNQVSLTCLVKGFYPSDI AVEWESNGQPENNYKTTPPVLDSDGSFFLYSRLTVDKS RWQEGNVFSCSVMHEALHNHYTQKSLSLSLGK (SEQ ID NO: 69) | DVQMTQSPSSLSASVGDRVTITCRASQSIVH SNGNTYLHWYQQKPGKAPKFLIYKVSNRFSG VPSRFSGSGSGTDFTLTISSLQPEDFATYYC AQSTLVPLTFGQGTKLEIKRTVAAPSVFIFP PSDEQLKSGTASVVCLLNNFYPREAKVQWKV DNALQSGNSQESVTEQDSKDSTYSLSSTLTL SKADYEKHKVYACEVTHQGLSSPVTKSFNRG EC (SEQ ID NO: 79) | e1711-F$_c$mod

| | |
|---|---|
| EVQLVESGGGLIQPGGSLRLSCAASGFTFNAYAMSWVR QAPGKGLEWVSSISTGGNTYYADSVKGRFTISRDNSKN TLYLQMNSLRAEDTAVYYCTRGYQRFSGFAYWGQGTLV TVSSASTKGPSVFPLAPCSRSTSESTAALGCLVKDYFP EPVTVSWNSGALTSGVHTFPAVLQSSGLYSLSSVVTVP SSSLGTKTYTCNVDHKPSNTKVDKRVESKYGPPCPPCP APEVEGGPSVFLFPPKPKDTLMISRTPEVTCVVVGVSQ EDPEVQFNWYVDGVEVHNAKTKPREEQFNSTYRVVSVL TVLHQDWLNGKEYKCKVSNKGLPSSIEKTISKAKGQPR EPQVYTLPPSQEEMTKNQVSLTCLVKGFYPSDIAVEWE SNGQPENNYKTTPPVLDSDGSFFLYSRLTVDKSRWQEG NVFSCSVMHEALHNHYTQKSLSLSLGK (SEQ ID NO: 80) | EIVLTQSPATLSLSPGERATLSCRSSQSLVH SNGNTYLNWYQQKPGQAPRLLIYKVSNRLSG IPARFSGSGSGTDFTLTISSLEPEDFAVYYC SQSTHVPYTFGQGTKLEIKRTVAAPSVFIFP PSDEQLKSGTASVVCLLNNFYPREAKVQWKV DNALQSGNSQESVTEQDSKDSTYSLSSTLTL SKADYEKHKVYACEVTHQGLSSPVTKSFNRG EC (SEQ ID NO: 81) | c2137-e1711-Fcmod

| | |
|---|---|
| QVQLVQSGAEVKKPGASVKVSCKASGYTFTNYWMHWVR QAPGQGLEWMGYLNPSSGYTKYAQKFQGRVTMTRDTST STVYMELSSLRSEDTAVYYCTRSGGDNYGNPYYFDRWG QGTTVTVSSASTKGPSVFPLAPCSRSTSESTAALGCLV KDYFPEPVTVSWNSGALTSGVHTFPAVLQSSGLYSLSS VVTVPSSSLGTKTYTCNVDHKPSNTKVDKRVESKYGPP CPPCPAPEVEGGPSVFLFPPKPKDTLMISRTPEVTCVV VGVSQEDPEVQFNWYVDGVEVHNAKTKPREEQFNSTYR VVSVLTVLHQDWLNGKEYKCKVSNKGLPSSIEKTISKA KGQPREPQVYTLPPSQEEMTKNQVSLTCLVKGFYPSDI AVEWESNGQPENNYKTTPPVLDSDGSFFLYSRLTVDKS RWQEGNVFSCSVMHEALHNHYTQKSLSLSLGGGGGSEI VLTQSPATLSLSPGERATLSCRSSQSLVHSNGNTYLNW YQQKPGQAPRLLIYKVSNRLSGIPARFSGSGSGTDFTL TISSLEPEDFAVYYCSQSTHVPYTFGCGTKLEIKGGGG SGGGGSGGGGSGGGGSEVQLVESGGGLIQPGGSLRLSC AASGFTFNAYAMSWVRQAPGKCLEWVSSISTGGNTYYA DSVKGRFTISRDNSKNTLYLQMNSLRAEDTAVYYCTRG YQRFSGFAYWGQGTLVTVSS (SEQ ID NO: 71) | DVQMTQSPSSLSASVGDRVTITCRASQSIVH SNGNTYLHWYQQKPGKAPKFLIYKVSNRFSG VPSRFSGSGSGTDFTLTISSLQPEDFATYYC AQSTLVPLTFGQGTKLEIKRTVAAPSVFIFP PSDEQLKSGTASVVCLLNNFYPREAKVQWKV DNALQSGNSQESVTEQDSKDSTYSLSSTLTL SKADYEKHKVYACEVTHQGLSSPVTKSFNR GEC (SEQ ID NO: 72) | c2139-e1711-F$_c$mod

| | |
|---|---|
| QVQLVQSGAEVKKPGASVKVSCKASGYTFTNYWMHWVR QAPGQGLEWMGYLNPSSGYTKYAQKFQGRVTMTRDTST STVYMELSSLRSEDTAVYYCTRSGGDNYGNPYYFDRWG | DVQMTQSPSSLSASVGDRVTITCRASQSIVH SNGNTYLHWYQQKPGKAPKFLIYKVSNRFSG VPSRFSGSGSGTDFTLTISSLQPEDFATYYC |

TABLE 6-continued

Sequences of Fc modified exemplary
monospecific and biparatopic antibodies.

| Heavy chain | Light chain |
|---|---|
| QGTTVTVSSASTKGPSVFPLAPCSRSTSESTAALGCLV<br>KDYFPEPVTVSWNSGALTSGVHTFPAVLQSSGLYSLSS<br>VVTVPSSSLGTKTYTCNVDHKPSNTKVDKRVESKYGPP<br>CPPCPAPEVEGGPSVFLFPPKPKDTLMISRTPEVTCVV<br>VGVSQEDPEVQFNWYVDGVEVHNAKTKPREEQFNSTYR<br>VVSVLTVLHQDWLNGKEYKCKVSNKGLPSSIEKTISKA<br>KGQPREPQVYTLPPSQEEMTKNQVSLTCLVKGFYPSDI<br>AVEWESNGQPENNYKTTPPVLDSDGSFFLYSRLTVDKS<br>RWQEGNVFSCSVMHEALHNHYTQKSLSLSLGGGGGSEI<br>VLTQSPATLSLSPGERATLSCRSSQSLVHSNGNTYLNW<br>YQQKPGQAPRLLIYKVSNRLSGIPARFSGSGSGTDFTL<br>TISSLEPEDFAVYYCSQSTHVPYTFGCGTKLEIKGGGG<br>SGGGGSGGGGSGGGGSEVQLVESGGGLIQPGGSLRLSC<br>AASGFTFNAYAMSWVRQAPGKCLEWVSSISTGGNTYYA<br>DSVKGRFTISRDNSKNTLYLQMNSLRAEDTAVYYCTRG<br>YQRFSGFAYWGQGTLVTVSS (SEQ ID NO: 71) | AQYTLVPLTFGQGTKLEIKRTVAAPSVFIFP<br>PSDEQLKSGTASVVCLLNNFYPREAKVQWKV<br>DNALQSGNSQESVTEQDSKDSTYSLSSTLTL<br>SKADYEKHKVYACEVTHQGLSSPVTKSFNRG<br>EC (SEQ ID NO: 82) |

Variable region

| VL of c2139-F$_c$mod | VH of c2139-F$_c$mod |
|---|---|
| DVQMTQSPSSLSASVGDRVTITCRASQSIVHSNGNTYL<br>HWYQQKPGKAPKFLIYKVSNRFSGVPSRFSGSGSGTDF<br>TLTISSLQPEDFATYYCAQYTLVPLTFGQGTKLEIK<br>(SEQ ID NO: 73) | QVQLVQSGAEVKKPGASVKVSCKASGYTFTN<br>YWMHWVRQAPGQGLEWMGYLNPSSGYTKYAQ<br>KFQGRVTMTRDTSTSTVYMELSSLRSEDTAV<br>YYCTRSGGDNYGNPYYFDRWGQGTTVTVSS<br>(SEQ ID NO: 74) |

In some embodiments, the monospecific anti-C5aR1 antibody comprises a heavy chain amino acid sequence having at least 70%, 75%, 80%, 85%, 90%, 91%, 92%, 93%, 94%, 95%, 96%, 97%, 98%, or 99% sequence identity to SEQ ID NO: 69.

In some embodiments, the monospecific anti-C5aR1 antibody comprises a light chain amino acid sequence having at least 70%, 75%, 80%, 85%, 90%, 91%, 92%, 93%, 94%, 95%, 96%, 97%, 98%, or 99% sequence identity to SEQ ID NO: 70.

In some embodiments, the biparatopic anti-C5aR1 antibody comprises a heavy chain amino acid sequence having at least 70%, 75%, 80%, 85%, 90%, 91%, 92%, 93%, 94%, 95%, 96%, 97%, 98%, or 99% sequence identity to SEQ ID NO: 71.

In some embodiments, the biparatopic anti-C5aR1 antibody comprises a heavy chain amino acid sequence having at least 70%, 75%, 80%, 85%, 90%, 91%, 92%, 93%, 94%, 95%, 96%, 97%, 98%, or 99% sequence identity to SEQ ID NO: 72.

In some embodiments, the monospecific anti-C5aR1 antibody comprises a light chain amino acid sequence having at least 70%, 75%, 80%, 85%, 90%, 91%, 92%, 93%, 94%, 95%, 96%, 97%, 98%, or 99% sequence identity to SEQ ID NO: 79.

In some embodiments, the monospecific anti-C5aR1 antibody comprises a light chain amino acid sequence having at least 70%, 75%, 80%, 85%, 90%, 91%, 92%, 93%, 94%, 95%, 96%, 97%, 98%, or 99% sequence identity to SEQ ID NO: 81.

In some embodiments, the monospecific anti-C5aR1 antibody comprises a light chain amino acid sequence having at least 70%, 75%, 80%, 85%, 90%, 91%, 92%, 93%, 94%, 95%, 96%, 97%, 98%, or 99% sequence identity to SEQ ID NO: 82.

Use of Monospecific and Biparatopic C5aR1 Antagonists for Treatment of Diseases

Described herein are methods of treating a disease associated with C5a/C5aR1 axis dysfunctions. Accordingly, in some embodiments, the monospecific and/or biparatopic antibodies against C5aR1 described herein are suitable for treating a subject that has a dysfunction associated with C5a/C5aR1 axis, such as ANCA-associated vasculitis.

Exemplary disorders or conditions that can be treated or prevented by the antibody molecules described herein include, but are not limited to, a C5aR1-associated disorder or a C5-associated disorder. In an embodiment, the disorder is associated with neutrophil recruitment, activation, and/or NETosis. In an embodiment, the disorder is associated with complement system activation and/or coagulation system activation. In an embodiment, the disorder is associated with a C5aR-mediated inflammatory response. In an embodiment, the disorder is associated with monocyte chemoattractant protein-1 (MCP-1) and/or renal inflammation. In an embodiment, the disorder is associated with chemotaxis (e.g., chemotaxis priming). In an embodiment, the disorder is associated with endothelium injury.

The method of treating includes administering to the subject in need thereof antibodies described herein. In an embodiment, the exemplary disorders, for example, a C5aR1-associated disorder, can be treated using an antibody capable of binding one or more amino acid residues of C5aR1 at Site II (SEQ ID NO: 3).

In an embodiment, the exemplary disorders, for example, a C5aR1-associated disorder, can be treated using an antibody capable of competing with an antibody binding to C5aR1 at Site I (SEQ ID NO: 1 or SEQ ID NO: 2) or at Site II (SEQ ID NO: 3).

In an embodiment, the exemplary disorders, for example, a C5aR1-associated disorder, can be treated using an antibody capable of competing with an antibody binding to C5aR1 at Site I (SEQ ID NO: 1 or SEQ ID NO: 2) and at Site II (SEQ ID NO: 3).

The monospecific and/or biparatopic antibodies described herein can be used to treat any disease associated with dysfunction associated with C5a/C5aR1 axis.

In some embodiments, the exemplary disorders, for example, a C5aR1-associated disorder, can be treated using a monospecific or biparatopic antibody capable of binding to C5aR1, wherein the antibody binds C5aR1 with an affinity of 10 pM to 50 nM.

In some embodiments, the antibodies can be administered to a subject in need thereof, intravenously, subcutaneously, intradermally or intramuscularly.

In some embodiments, a nucleic acid encoding the monospecific or biparatopic antibodies described herein can be administered to a subject in need thereof using an appropriate delivery method. Several methods for delivering nucleic acids are known in literature. For example, a rAAV vector encoding the monospecific or biparatopic antibodies described herein can be administered to a subject administered by intravenous, intraperitoneal, subcutaneous, or intradermal administration. In some embodiments, the delivery of the nucleic acid encoding the antibody can be achieved using a "gene gun", a biolistic particle delivery system or a non-viral lipid nanoparticle.

In some embodiments, the monospecific or biparatopic antibodies described herein can be administered to a subject in need thereof in combination with an additional therapeutic. In some embodiments, the additional therapeutic is a small molecule, such as avacopan, corticosteroids or immunosuppressive drugs. Exemplary corticosteroids include but are not limited to, prednisolone, hydrocortisone, prednisone, dexamethasone or cortisone. Exemplary immunosuppressive drugs include, but are not limited to methotrexate, Azathioprine, Mycophenolate mofetil or cyclophosphamide.

In some embodiments, the monospecific or biparatopic antibodies described herein are better than avacopan monotherapy in alleviating neutropenia, in vivo.

In some embodiments, the monospecific or biparatopic antibodies described herein are better than avacopan in antagonizing C5aR1 in the presence of 100 nM of greater concentrations of C5a.

In some embodiments, the monospecific or biparatopic antibodies described herein are better than avacopan in inhibiting Gα signaling, in vitro.

In some embodiments, the monospecific or biparatopic antibodies described herein are better than avacopan in inhibiting calcium signaling, in vitro and in vivo.

In some embodiments, the monospecific or biparatopic antibodies described herein are better than avacopan in inhibiting neutrophil chemotaxis, in vitro and in vivo.

In some embodiments, the monospecific or biparatopic antibodies described herein are stable in serum for up to 500 hours post injection.

In some embodiments, the monospecific or biparatopic antibodies described herein are better than avacopan in inhibiting CD11b expression, in vitro and in vivo.

Nucleic Acids, Vectors and Methods of Manufacturing

The present disclosure also features nucleic acids comprising nucleotide sequences that encode the antibody molecules (e.g., heavy and light chain variable regions and CDRs of the antibody molecules), as described herein.

For example, the present disclosure features a first and second nucleic acid encoding heavy and light chain variable regions, respectively, of an antibody molecule chosen from one or more of the antibody molecules disclosed herein, e.g., an antibody molecule of Table 1C, or a portion of an antibody molecule, e.g., the variable regions of any of the antibodies disclosed herein. The nucleic acid can comprise a nucleotide sequence encoding any one of the amino acid sequences in the tables herein, or a sequence substantially identical thereto (e.g., a sequence at least about 85%, 90%, 95%, 99% or more identical thereto, or which differs by no more than 3, 6, 15, 30, or 45 nucleotides from the sequences shown in the tables herein).

In certain embodiments, the nucleic acid comprises a nucleotide sequence encoding at least one, two, or three CDRs from a heavy chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In an embodiment, the nucleic acid comprises a nucleotide sequence encoding at least one, two, or three CDRs from a light chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In an embodiment, the nucleic acid comprises a nucleotide sequence encoding at least one, two, three, four, five, or six CDRs from heavy and light chain variable regions having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions).

The nucleic acids disclosed herein include deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

In some aspects, the application features host cells and vectors containing the nucleic acids described herein. The nucleic acids may be present in a single vector or separate vectors present in the same host cell or separate host cell, as described in more detail below.

Vectors

Further provided herein are vectors that comprise nucleotide sequences encoding the antibody molecules (e.g., heavy and light chain variable regions and CDRs of the antibody molecules), as described herein.

In an embodiment, the vector comprises a nucleic acid described herein. For example, the vector can comprises a first and second nucleic acid encoding heavy and light chain variable regions, respectively, of an antibody molecule chosen from one or more of the antibody molecules disclosed herein, e.g., an antibody molecule described herein, or a portion of an antibody molecule, e.g., the variable regions of any of Tables 1-4.

In certain embodiments, the vector comprises a nucleotide sequence encoding at least one, two, or three CDRs from a heavy chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In an embodiment, the vector comprises a nucleotide sequence encoding at least one, two, or three CDRs from a light chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In an embodiment, the vector comprises a nucleotide sequence encoding at least one, two, three, four, five, or six CDRs from heavy and light chain variable regions having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions).

The vectors include, but are not limited to, a virus, plasmid, cosmid, lambda phage or a yeast artificial chromosome (YAC). Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid-based transfection or other conventional techniques. In the case of protoplast fusion, the cells are grown in media and screened for the appropriate activity.

Methods and conditions for culturing the resulting transfected cells and for recovering the antibody molecule produced are known to those skilled in the art and may be varied or optimized depending upon the specific expression vector and mammalian host cell employed, based upon the present description.

Cells

The present disclosure also provides cells (e.g., host cells) comprising a nucleic acid encoding an antibody molecule as described herein. For example, the host cells may comprise a nucleic acid molecule having a nucleotide sequence encoding an amino acid sequence described in any of Tables 1-5, a sequence substantially homologous thereto (e.g., a sequence at least about 85%, 90%, 95%, 99% or more identical thereto, and/or capable of hybridizing under the stringency conditions described herein), or a portion of one of said nucleic acids.

In an embodiment, the host cells are genetically engineered to comprise nucleic acids encoding the antibody molecule described herein.

In certain embodiments, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The disclosure also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells. In an embodiment, the cell (e.g., host cell) is an isolated cell.

Methods of Administration

Compositions of the invention can be formulated in any suitable form, such as liquid, semi-solid and solid dosage forms, such as liquid solutions (e.g., injectable and infusible solutions), dispersions or suspensions, and the like. The optimal form for any composition depends on the intended mode of administration, the nature of the composition or combination, and therapeutic application or other intended use. A typical mode for delivery for a composition of the invention is by parenteral administration (e.g., intravenous administration). In one aspect, a composition of the invention is administered to a human patient by intravenous infusion or injection.

In some aspects, this disclosure provides compositions, e.g., pharmaceutically acceptable compositions, which include an antibody molecule described herein, formulated together with a pharmaceutically acceptable carrier. As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g., by injection or infusion).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin. The antibody molecules described herein can be administered by a variety of methods. Several are known in the art, and for many therapeutic, prophylactic, or diagnostic applications, an appropriate route/mode of administration is intravenous injection or infusion. As will be appreciated by the skilled artisan, the route and/or mode of administration will vary depending upon the desired results.

EXAMPLES

Other features, objects, and advantages of the present disclosure are apparent in the examples that follow. It should be understood, however, that the examples, while indicating embodiments of the present disclosure, are given by way of illustration only, not limitation. Various changes and modifications within the scope of the disclosure will become apparent to those skilled in the art from the examples.

Example 1. Kinetic Analyses of C5aR1 Antagonistic Humanized Antibodies

This Example describes the binding affinity and specificity of Site II monospecific antibody and biparatopic antibodies described herein, to C5aR1 and C5aR2.

(a) Binding Affinity

Figures 4A, 4B:
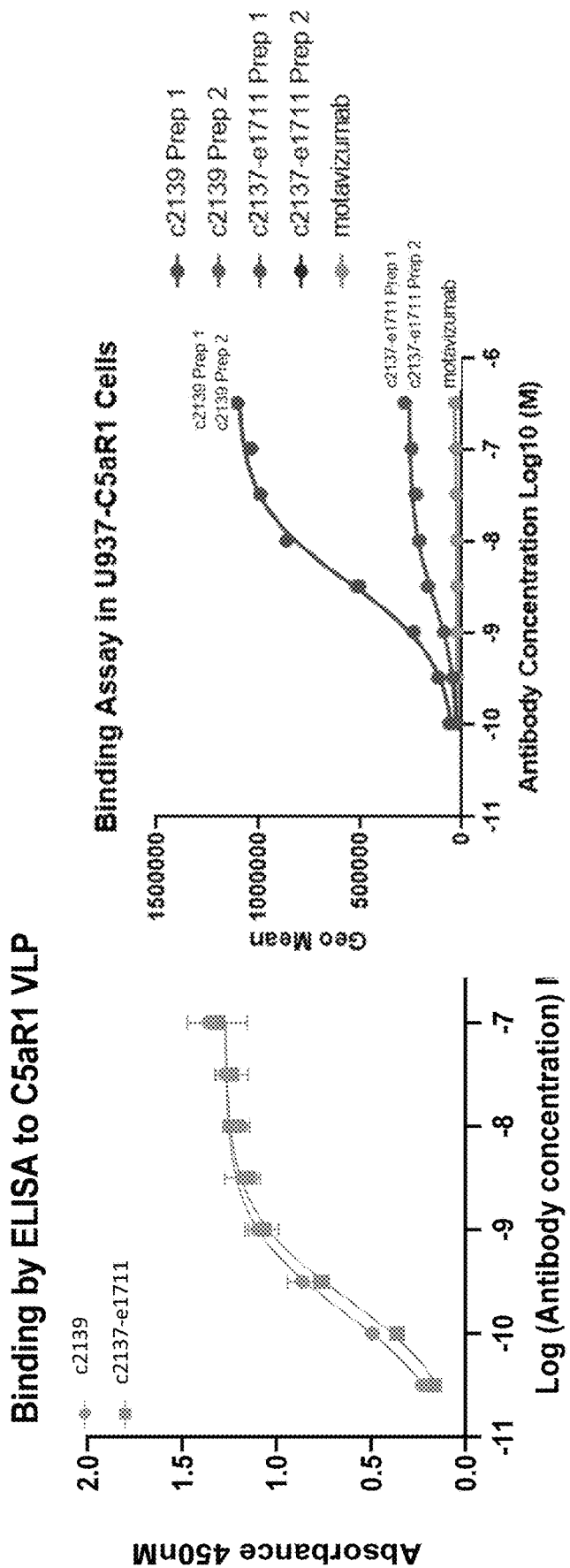
FIG. 4A is an exemplary graph showing binding of an exemplary humanized Site II antibody (c2139) and an exemplary biparatopic antibody (c2137-e1711) to C5aR1 using ELISA, as described in this disclosure.
FIG. 4B is an exemplary graph showing binding of different batches of an exemplary site II antibody (c2139) and an exemplary biparatopic antibody (c2137-e1711) in U937-C5aR1 cells.

The binding affinity of the antibodies to the target receptor, C5aR1, was determined using an ELISA assay. C5aR1 VLP were immobilized to a MaxiSorp ELISA plate at a concentration of 30 µg/mL and incubated overnight at 4° C. The following morning, plates were washed 3 times with 1×PBS and plates were blocked for 30 minutes with 100 µL of PBSA (1×PBS with 3% BSA). A serial titration of anti-C5aR1 antibody was performed in the presence of PBSA and incubated for 1 hour at room temperature. Plates were washed 6 times with PBSA. Anti-human-HRP was diluted in PBSA, added to all wells, and incubated for 45 minutes at room temperature. Plates were washed 6 times with PBS. TMB substrate was added to all wells and incubated for 10 minutes before the addition of stop solution (0.1 M sulfuric acid). Absorbance at 450 nm was measured on a standard plate reader. A four-parameter curve fit was used to generate the EC50 value of the antibody titration in nM. Affinity curves of a monospecific c2139 and a biparatopic c2137-e1711 antibodies are illustrated in FIG. 4A.

It was observed that under the conditions described above, the monospecific C5aR1 antibody, bound C5aR1 with an affinity of about 0.16 nM and the biparatopic antibody bound C5aR1 with an affinity of about 0.22 nM.

Figure 4C:
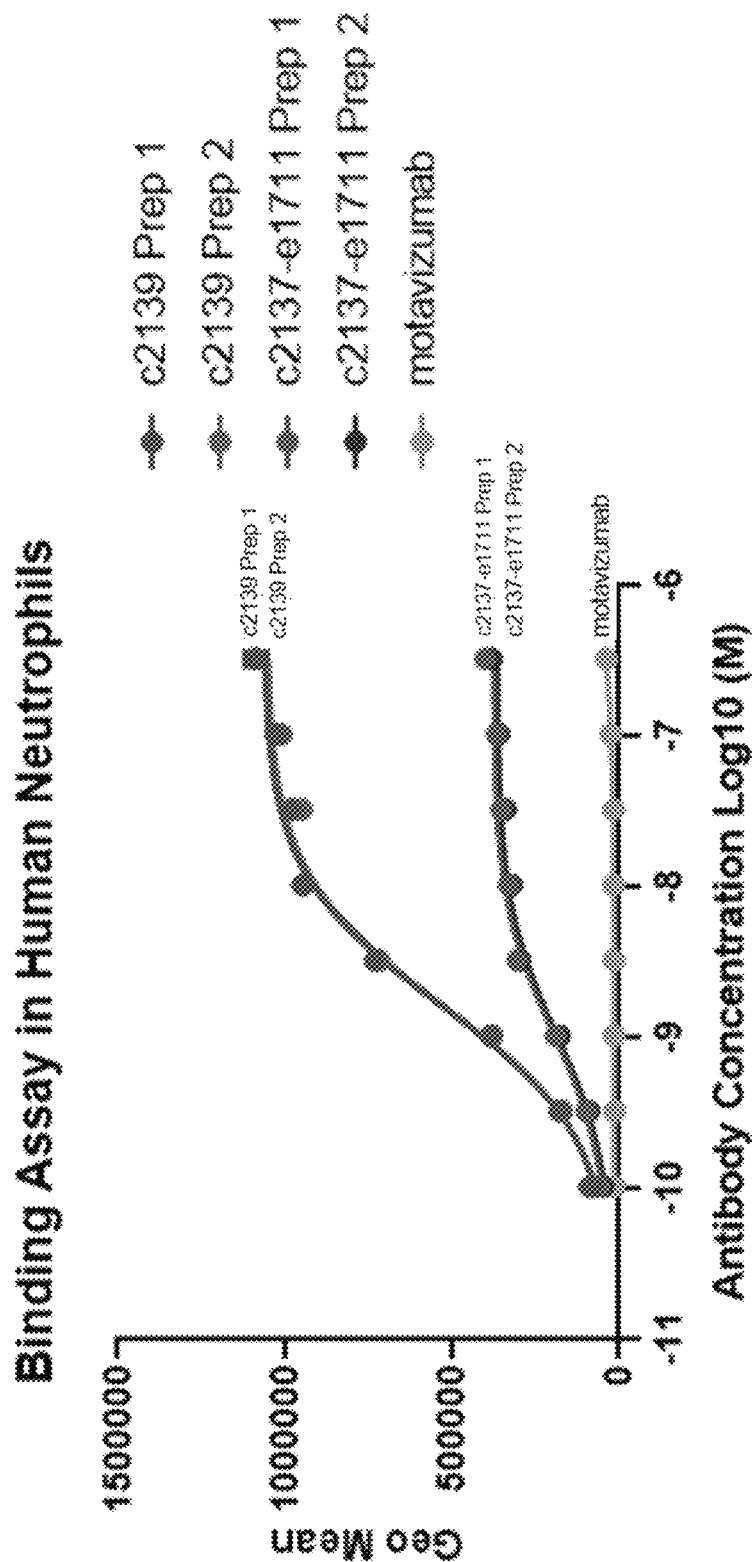
FIG. 4C is a graph showing binding of different batches of an exemplary site II antibody (c2139) and an exemplary biparatopic antibody (c2137-e1711) in human neutrophils cells.

In another setting, the binding of site II antibody, c2139 and biparatopic antibody c2137-e1711 from two different antibody batches were assayed for binding to U937-C5aR1 cells (FIG. 4B) and human neutrophils (FIG. 4C). The EC50 of U937-C5aR1 binding to different protein batches of anti-C5aR1 antibody (c2139 and c2137-e1711) different shown in Table 6.

TABLE 6

EC50 of U937-C5aR1 binding to exemplary C5aR1 antibody

| Antibody | EC50 (nM) | R Squared |
|---|---|---|
| c2139 Prep 1 | 3.64 | 0.99 |
| c2139 Prep 2 | 3.60 | 0.99 |
| c2137-e1711 Prep 1 | 2.47 | 0.98 |
| c2137-e1711 Prep 2 | 2.25 | 0.98 |
| motavizumab | No Binding | n/a |

The EC50 of human neutrophil binding to different protein batches of anti-C5aR1 antibody (c2139 and c2137-e1711) different shown in Table 7.

TABLE 7

EC50 of human neutrophil binding to exemplary C5aR1 antibody

| Antibody | EC50 (nM) | R Squared |
|---|---|---|
| c2139 Prep 1 | 1.64 | 0.99 |
| C2139 Prep 2 | 1.66 | 0.99 |
| c2137-e1711 Prep 1 | 1.07 | 0.99 |
| c2137-e1711 Prep 2 | 1.05 | 0.99 |
| motavizumab | No Binding | n/a |

A non-C5aR1 antibody, motavizumab was used as a control. It was observed that both Site II antibody, c2139 and biparatopic antibody c2137-e1711 bound U937 and human neutrophils across multiple antibody preparation lots.

(b) Binding Specificity

The specificity of the C5aR1 antagonistic antibodies was determined by measuring the affinity of anti-C5aR1 antibodies to C5aR2. C5aR2 VLP were immobilized to a MaxiSorp ELISA plate at a concentration of 30 µg/mL and incubated overnight at 4° C. The following morning, plates were washed 3 times with 1×PBS and plates were blocked for 30 minutes with 100 µL of PBSA (1×PBS with 3% BSA). A serial titration of anti-C5aR1 antibody was performed in the presence of PBSA and incubated for 1 hour at room temperature. Plates were washed 6 times with PBSA. Anti-human-HRP was diluted in PBSA, added to all wells, and incubated for 45 minutes at room temperature. Plates were washed 6 times with PBS. TMB substrate was added to all wells and incubated for 10 minutes before the addition of stop solution (0.1 M sulfuric acid). Absorbance at 450 nm was measured on a standard plate reader. A four-parameter curve fit was used to generate the EC50 value of the antibody titration in nM.

Figure 5:
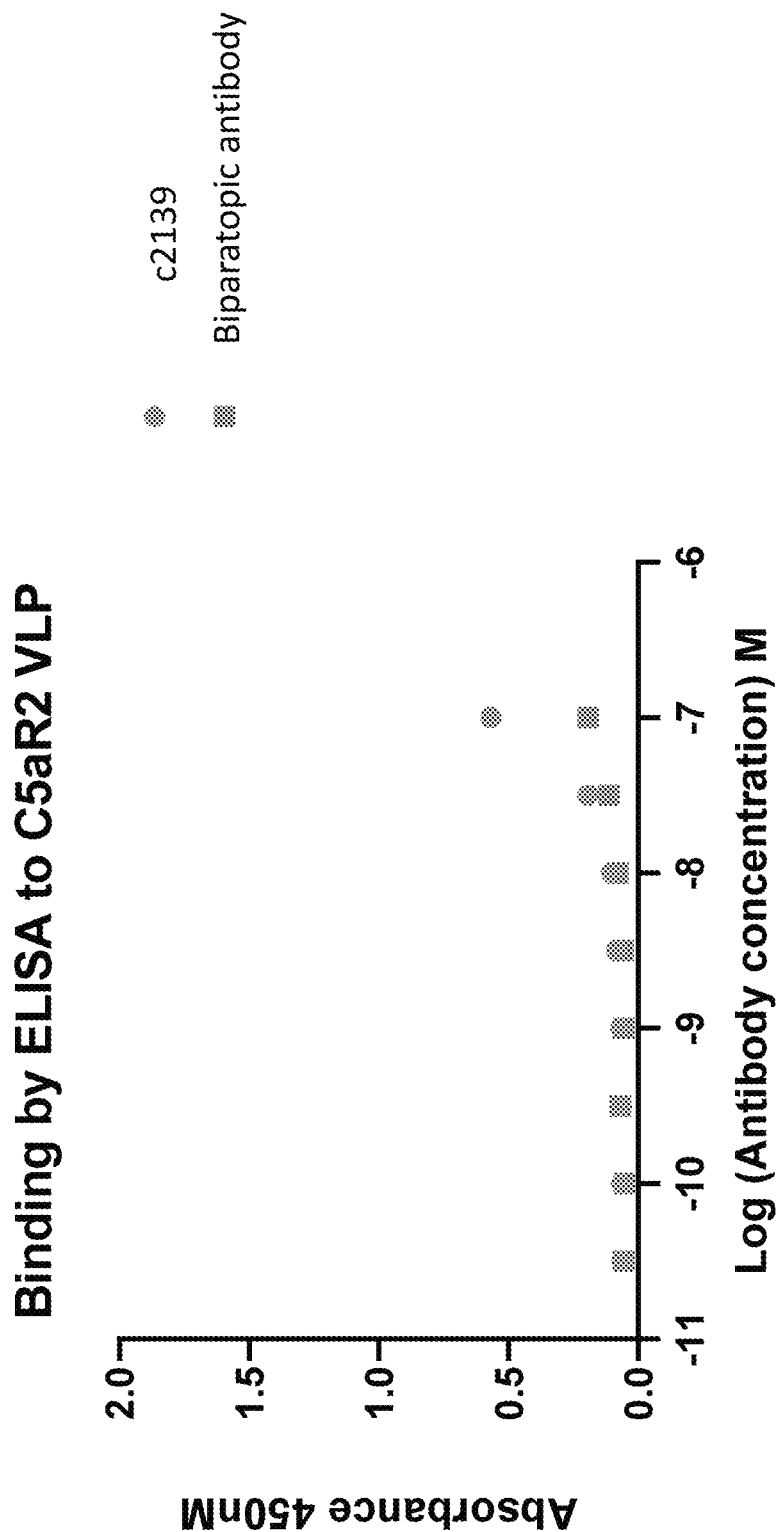
FIG. 5 is an exemplary graph showing binding of an exemplary humanized Site II antibody (c2139) and biparatopic antibody (c2137-e1711) to C5aR2 using ELISA, as described in this disclosure.

A binding data of a monospecific and a biparatopic antibody is illustrated in FIG. 5. It was observed that under the conditions described above the exemplary C5aR1 antagonistic antibodies did not bind C5aR2. Overall, the data in this example showed that anti-C5aR1 antibodies of the present invention bind C5aR1 with high affinity, and with unmeasurable affinity to C5aR2, illustrating that the C5aR1 antibodies are indeed specific for C5aR1.

Example 2. Inhibition of Gα Signaling

This Example describes the functional aspect of C5aR1 monospecific antibodies and biparatopic antibodies described herein, for inhibition of Gα signaling using a GeneBLazer assay.

The GeneBLAzer assay kit and C5aR1 cell line were commercially available from Thermo Fisher (Catalog #K1544). The assay was performed as recommend by the manufacturer. Briefly, antibodies or antagonists were incubated for 30 minutes at increasing concentrations at 37° C. C5a was then added to the cells and incubated at 37° C. for an additional 4-5 hours. Beta-lactamase substrate was then added and incubated for 2 hours at room temperature. Fluorescent measurements for each well with an excitation/ emission of 409/460 (blue) and 409/530 (green) were measured. An increase in the blue to green ratio was proportional to C5aR1 activation and was used to calculate the percent of activation for the cells in each well. The C5aR1 activation profile was monitored under increasing antagonist concentration. The IC50 was determined by plotting the percentage of signal against concentration of the antagonist.

Figure 6A:
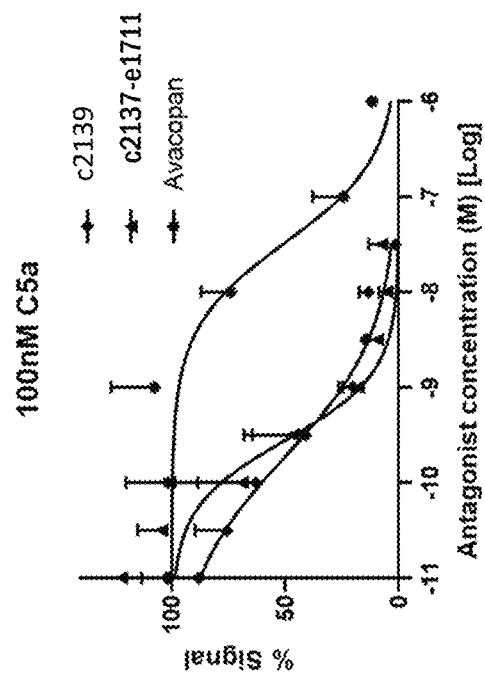
FIG. 6A is an exemplary graph showing inhibition of G-alpha signaling using GeneBLAzer assay using an exemplary humanized Site II antibody, c2139 and an exemplary biparatopic antibody, c2137-e1711 to C5aR1, as described in this disclosure, in the presence of 10 nM C5a. Avacopan is shown as a positive control.

A Gα signaling assay of a monospecific and a biparatopic antibody is illustrated in FIG. 6A as a function of antibody concentration with 10 nM C5a. In another setting, a known C5aR antibody, an anti-C5aR1 control Ab is used as a positive control for inhibition of Gα signaling (FIG. 6C).

Figure 6B:
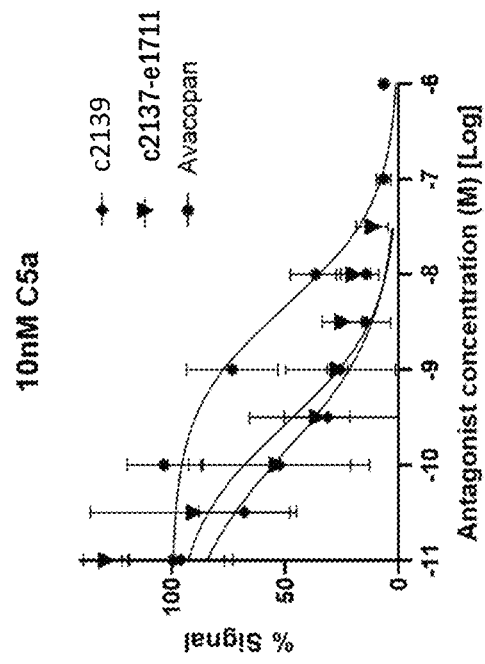
FIG. 6B is an exemplary graph showing inhibition of G-alpha signaling using GeneBLAzer assay using an exemplary humanized Site II, c2139 antibody and an exemplary biparatopic antibody to C5aR1, c2137-e1711, as described in this disclosure, in the presence of 100 nM C5a. Avacopan is shown as a positive control.
Figure 6D:
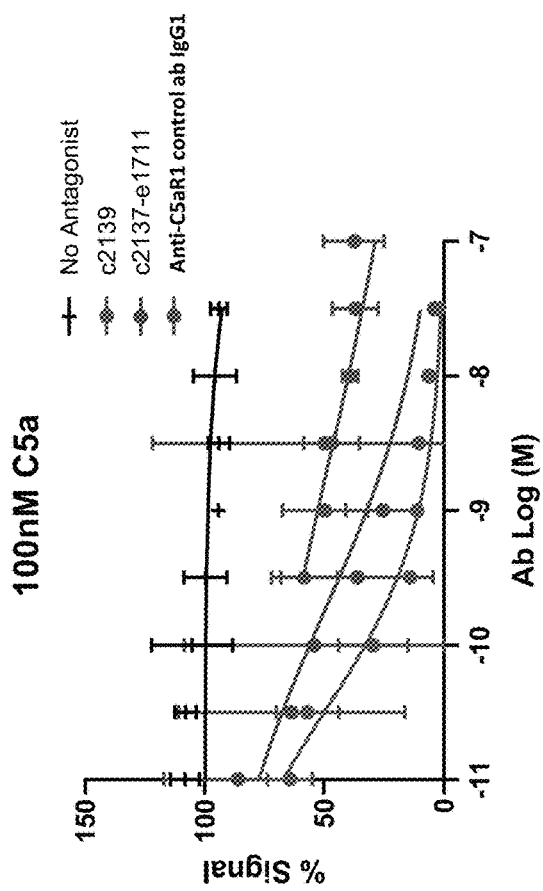
FIG. 6D is an exemplary graph showing inhibition of G-alpha signaling using GeneBLAzer assay using an exemplary humanized Site II, c2139 antibody and an exemplary biparatopic antibody to C5aR1, c2137-e1711, as described in this disclosure, in the presence of 100 nM C5a. An anti-C5aR1 control Ab is shown as a positive control.
Figure 6C:
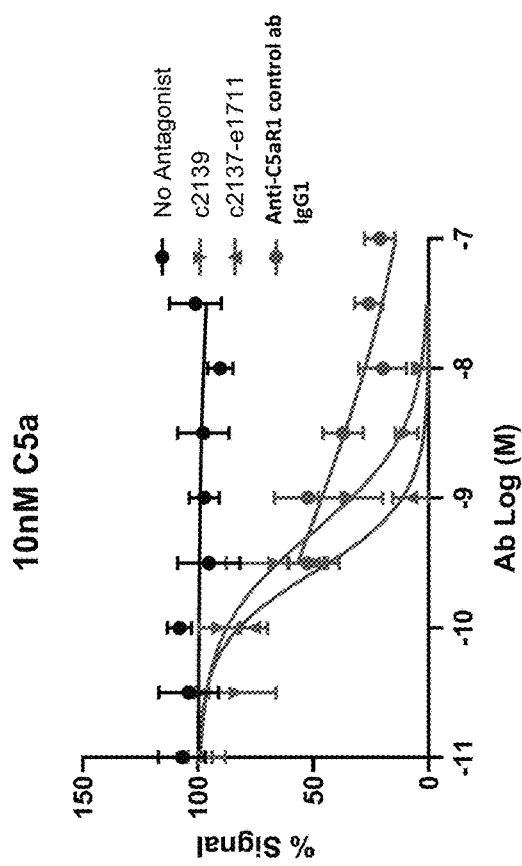
FIG. 6C is an exemplary graph showing inhibition of G-alpha signaling using GeneBLAzer assay using an exemplary humanized Site II antibody, c2139 and an exemplary biparatopic antibody, c2137-e1711 to C5aR1, as described in this disclosure, in the presence of 10 nM C5a. An anti-C5aR1 control Ab is shown as a positive control.

A Gα signaling assay of a monospecific and a biparatopic antibody is illustrated in FIG. 6B as a function of antibody concentration with 100 nM C5a. In another setting, a known C5aR antibody, an anti-C5aR1 control Ab is used as a positive control for inhibition of Gα signaling (FIG. 6D). It was observed that the IC50 of monospecific C5aR1 antagonist was 0.14 nM with 10 nM C5a and 0.19 nM with 100 nM C5a. The IC50 of bispecific C5aR1 antagonist was 0.27 nM with 10 nM C5a and 0.28 nM with 100 nM C5a. It was observed that the exemplary antibodies retained superior inhibition compared to Avacopan and an anti-C5aR1 control Ab at all concentrations of C5a tested.

Example 3. Inhibition of Calcium Signaling

This Example describes the functional aspect of C5aR1 monospecific antibodies and biparatopic antibodies described herein, for inhibition of C5a mediated calcium signaling, using calcium flux assays.

The potency of the antibodies was assessed for their ability to inhibit intracellular calcium release in C5aR1 expressing stable C5aR1-U937 cells or neutrophils isolated from whole blood in the presence of C5a. Calcium flux assays using calcium sensitive dye were utilized to detect cytosolic changes in calcium concentration. Cells were incubated with esterified (inactive) calcium dye. The dye penetrated the cell membrane and became active once inside the cell. The active form of the dye became fluorescent after binding to intracellular calcium and the fluorescence was used to determine C5aR1 signaling in response to C5a addition. Specifically, the stable C5aR1-U937 or neutrophils isolated from whole blood were stained with Fluo-4 Direct calcium Assay kit from Thermo Fisher for 1 hour at 37° C. Next, antibody or antagonist was incubated with the cells for 30 minutes. The basal fluorescence with an excitation at 494 nm and emission at 516 nm was measured for 15 seconds. C5a was added to the cells and the fluorescence was measured over a span of four minutes. The basal read from before C5a stimulation and the max signal after C5a stimulation were used to calculate the response ratio. The calcium flux assays were performed using engineered cells stably expressing C5aR1 as well as using human neutrophils.

An inhibition of C5a-meditated calcium signaling assay of a monospecific (FIG. 7A) and a biparatopic antagonistic antibody (FIG. 7B) is illustrated in as a plotted as calcium flux as a function C5a concentration and with increasing antibody concentration. Further, inhibition of C5a-meditated calcium signaling with a known C5aR1 antagonist, Avacopan, is illustrated using the protocol as described above in FIG. 7C. It was observed that the tested antibodies were better at inhibition of calcium signaling than avacopan.

Example 4. Inhibition of Neutrophil Chemotaxis

This Example describes the functional aspect of C5aR1 monospecific antibodies and biparatopic antibodies described herein, for inhibition of neutrophil chemotaxis, which is known to be induced by C5aR1 activity, using a Boyden Chamber.

First, C5aR1-U937 stable cells were seeded into the top chamber of a 96 Transwell plate in the presence of no antibody (antagonist), or of 1, 10, or 100 nM each antibody (antagonist). The bottom chamber contained a half-log titration of C5a (chemoattractant) ranging from $10^{-6}$ to $10^{-9.5}$ M. The top and the bottom chambers were separated by a membrane. C5a is expected to induce migration of U937 cells. However, use of a C5aR1 antagonist is expected to inhibit this migration. Increasing concentration of the exemplary antibodies were used to determine a dose-dependent inhibition of chemotaxis. Further, increasing concentration of the chemoattractant (C5a) was used to determine if the inhibition of chemotaxis was surmountable by using high concentration of C5a. In a parallel setting, a known C5aR1 inhibitor, Avacopan was also used to evaluate the inhibition of chemotaxis of neutrophils and surmountability of the chemotaxis in the presence of excess C5a.

Second, human neutrophils were seeded into the top chamber of a 96 Transwell plate in the presence of no antibody (antagonist), or of 1, 10, or 100 nM each antibody (antagonist). The bottom chamber contained a half-log titration of C5a (chemoattractant) ranging from $10^{-6}$ to $10^{-9.5}$ M. The top and the bottom chambers were separated by a membrane. C5a is expected to induce migration of U937 cells. However, use of a C5aR1 antagonist is expected to inhibit this migration. Increasing concentration of the antibodies were used to determine a dose-dependent inhibition of chemotaxis. Further, increasing concentration of the chemoattractant (C5a) was used to determine if the inhibition of chemotaxis was surmountable by using high concentration of C5a. In a parallel setting, a known C5aR1 inhibitor, Avacopan was also used to evaluate the inhibition of chemotaxis of neutrophils and surmountability of the chemotaxis in the presence of excess C5a.

Figure 8C:
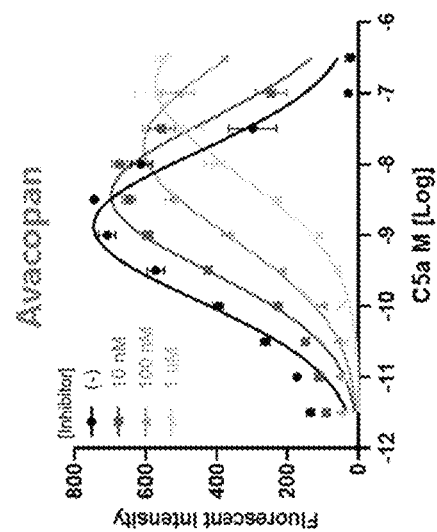
FIG. 8C is an exemplary graph showing inhibition of neutrophil chemotaxis using avacopan, a known C5aR1 inhibitor, as described in this disclosure, in the presence of increasing concentrations of C5a and increasing concentrations of antibody
Figure 8B:
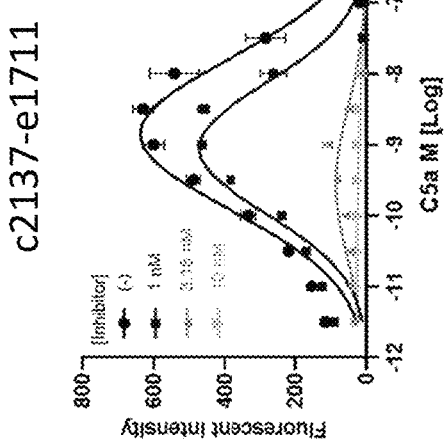
FIG. 8B is an exemplary graph showing inhibition of neutrophil chemotaxis using a humanized biparatopic antibody, c2137-e1711 as described in this disclosure, in the presence of increasing concentrations of C5a and increasing concentrations of antibody.
Figure 8A:
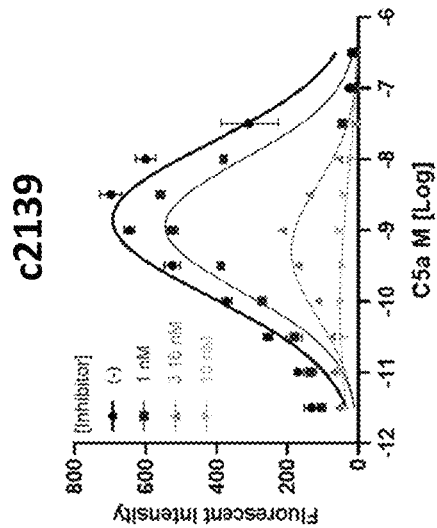
FIG. 8A is an exemplary graph showing inhibition of neutrophil chemotaxis using an exemplary humanized Site II antibody, c2139 as described in this disclosure, in the presence of increasing concentrations of C5a and increasing concentrations of antibody.

FIG. 8A-8C shows the amount of fluorescence intensity versus the C5a concentration, in the presence of different concentration of the anti-C5aR1 antibodies, indicating inhibition of chemotaxis by the anti-C5aR1 antibodies. It was observed that the anti-C5aR1 antibodies generally inhibited cell chemotaxis in a dose-dependent manner. Further, it was observed that unlike Avacopan, the inhibition of neutrophil chemotaxis was insurmountable in the presence of excess C5a, by the anti-C5aR1 antibodies.

Example 5. Inhibition of CD11b Expression

This Example describes the functional aspect of C5aR1 monospecific antibodies and biparatopic antibodies described herein, for inhibition of CD11b expression.

CD11b, an integrin receptor, is mobilized to the surface of neutrophils in response to C5a activation and mediates intravascular crawling prior to neutrophil transmigration. CD11 is involved in numerous adhesion-related associations between cells such as monocytes, macrophages, natural killer (NK) cells, and granulocytes.

Figures 9A, 9B:
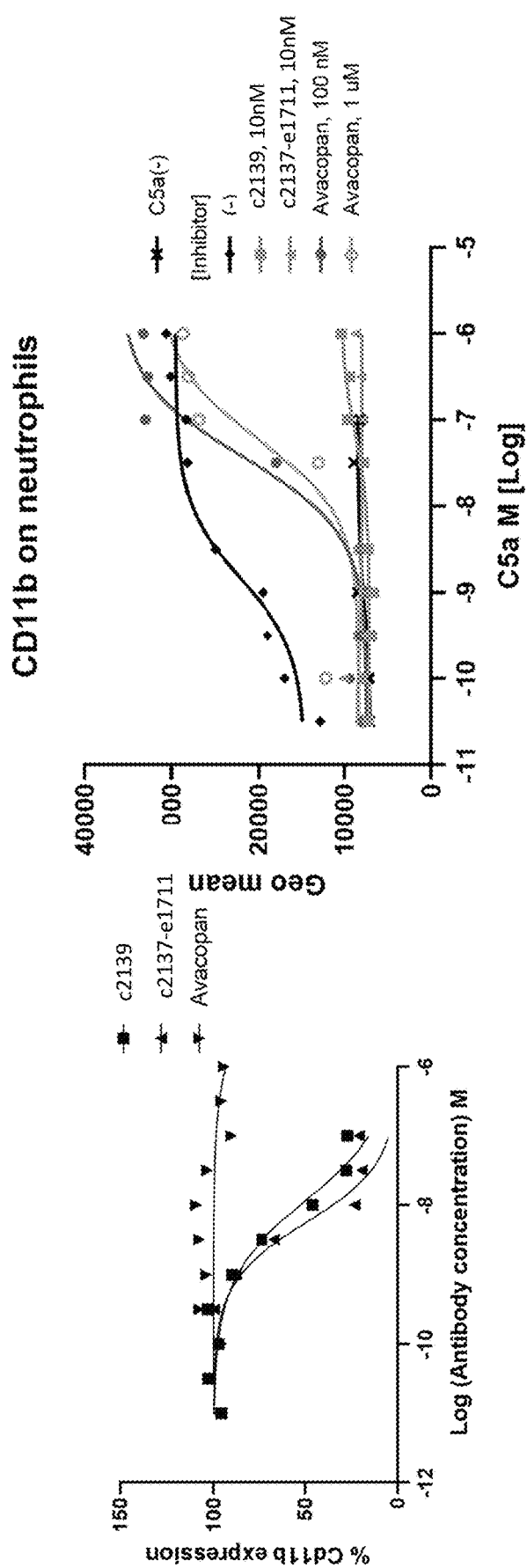

FIG. 9A-9B shows the percentage of CD11b expression versus the antibody (C5aR1 antagonist) concentration, in the presence of 100 nM C5a. It was observed that the antibodies potently inhibited CD11b across the entire range of expected physiological concentration of C5a. Table 8 shows the IC50 of c2139 and c2137-e1711 in the presence of 100 nM C5a.

TABLE 8

IC50 of CD11b expression inhibition using exemplary C5aR1 antibodies

| Antagonist | IC50 (nM) 100 nM C5a |
|---|---|
| C2139 | 1.85 |
| C2137-e1711 | 1.47 |

Figure 9C:
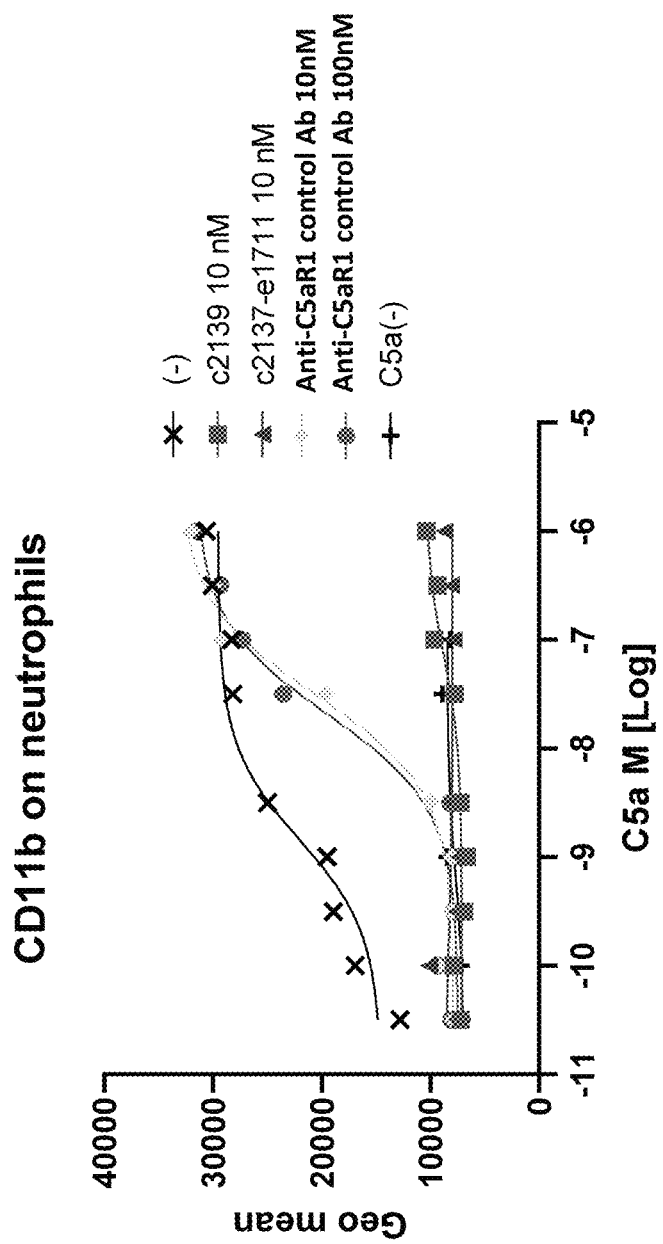

In another setting, 10 nM and 100 nM an anti-C5aR1 control Ab was used as a control to compare the inhibition of the anti-C5aR1 antibodies disclosed herein (FIG. 9C) in human neutrophils. It was observed further observed that avacopan was only partially potent in inhibition of CD11b. It was further observed that instant antibodies were better inhibitors than an anti-C5aR1 control Ab.

Example 6. Inhibition of β-Arrestin Recruitment

This Example describes the functional aspect of C5aR1 monospecific antibody, and biparatopic antibodies described herein, for inhibition of β-arrestin recruitment.

To characterize the lead mAbs as full antagonists of C5aR1, we aimed to evaluate the potential of the lead mAbs to inhibit β-arrestin2 recruitment. The β-arrestin assay utilized a proprietary two-subunit luciferase reporter system: one subunit is fused to C5aR1 and one subunit is fused to β-arrestin2. When in close proximity, the two subunits formed an enzyme that generates a luminescent signal, used as a proxy for C5aR1-mediated recruitment of β-arrestin2. Exemplary antibodies significantly reduced C5aR1-mediated recruitment of β-arrestin2 at two different C5a concentrations, 1 nM and 10 nM. FIGS. 10A-10C are graphs showing the inhibition of the fluorescent signal, after addition of 1 nM (FIG. 10A), 10 nM (FIG. 10B) and 100 nM (FIG. 10C) C5a. Table 9 shows the IC50 of c2139, c2137-e1711 and avacopan mediated inhibition of β-arrestin.

TABLE 9

IC50 of monospecific or biparatopic antibody for β-arrestin signaling

| | 10 nM C5a | | 100 nM C5a | |
|---|---|---|---|---|
| Name | IC50 | R value | IC50 | R value |
| c2139 | 1.783 nM | 0.995 | 0.6516 nM | 0.999 |
| c2137-e1711 | 0.766 nM | 0.829 | 0.3598 nM | 0.972 |
| Avacopan | 9.953 nM | 0.818 | 3.246 nM | 0.846 |

When compared to the small molecule C5aR1 inhibitor avacopan, exemplary antibodies, c2139 and c2137-e1711 showed superior inhibition of signal, even when avacopan was used at 10-fold higher concentrations than the antibodies. Notably, avacopan lost potency as C5a concentrations increase to 10 nM, whereas c2139 and c2137-e1711 maintain >75% inhibition of β-arrestin2 recruitment. The data suggested that the exemplary C5aR1 antibodies, c2139 and c2137-e1711 inhibit β-arrestin at 10-fold lower concentrations than Avacopan.

Example 7. Inhibition of ROS Production by Humanized Anti-C5aR1 Antibodies

This example shows that exemplary humanized monospecific antibodies (c2139) and exemplary biparatopic antibodies (c2137-e1711) reduced reactive oxygen species (ROS).

Figure 11:
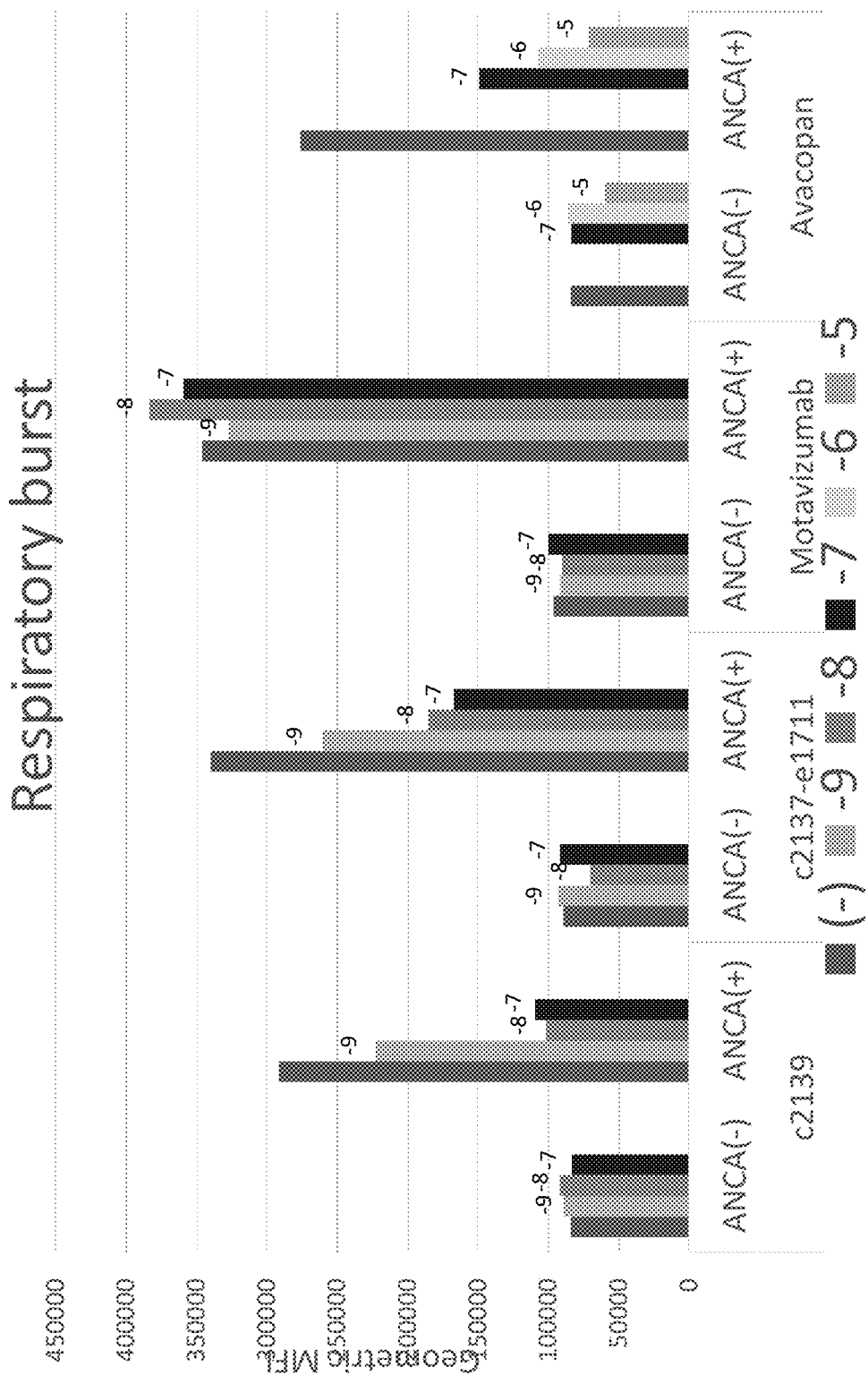
FIG. 11 is an exemplary graph showing the inhibition of ROS signaling in ANCA(−) and ANCA (+) cells as compared to c2139, c2137-e1711, motavizumab and Avacopan.

ROS production by neutrophils was detected with a Cellular ROS Detection Assay Kit (Abcam) following manufacturer's manual. The RBC-lysed WB cells were diluted to the concentration of $3 \times 10^5$ cells in 100 mL buffer. Pre-treatment with ROS inhibitor (N-acetyl-L-cysteine) was carried out for the negative control group at 37° C., 5% CO2 for 30 minutes. ROS detection antibody then added into the antibody cocktail for flow cytometry-based detection of neutrophil ROS production. ROS inducer (pyocyanin) was added to all groups and incubated for 30 minutes prior to acquisition on the cytometer. FIG. 11 shows the ROS production in neutrophils in response in ANCA– and ANCA+ groups in response to treatment with anti-C5aR1 antibodies.

It was observed that c2139 and c2137-e1711 inhibited ANCA induced ROS production.

Example 8. Internalization of Humanized Anti-C5aR1 Antibodies in U937 Cells

This example shows the internalization of humanized monospecific and biparatopic C5aR1 antibodies in hC5ar1-U937 cells.

The humanized monospecific anti-C5aR1 antibody, e1711 and biparatopic antibody, c2139-e1711 were conjugated to pH sensitive dye, which Fluoresces brightly at low pH but is non-fluorescent at neutral pH. The conjugated antibodies were incubated with U937 cells and hC5aR1 knock in U937 cells. FIG. 12A-12D show the fluorescence intensity after 24 hours of incubation with each conjugated antibody. FIG. 12A-FIG. 12B shows fluorescence intensity of U037 cells or U937-C5aR1 cells with 10 nM antibodies; and FIG. 12C-FIG. 12D shows fluorescence intensity of U037 cells or U937-C5aR1 cells with 100 nM antibodies.

Example 9. Cross-Reactivity of Humanized Anti-C5aR1 Antibodies

This example shows the binding of humanized anti-C5aR1 antibody, e1711 and biparatopic antibody, c2139-e1711 to C5aR1 in squirrel monkey and dog.

Figures 13A, 13B:
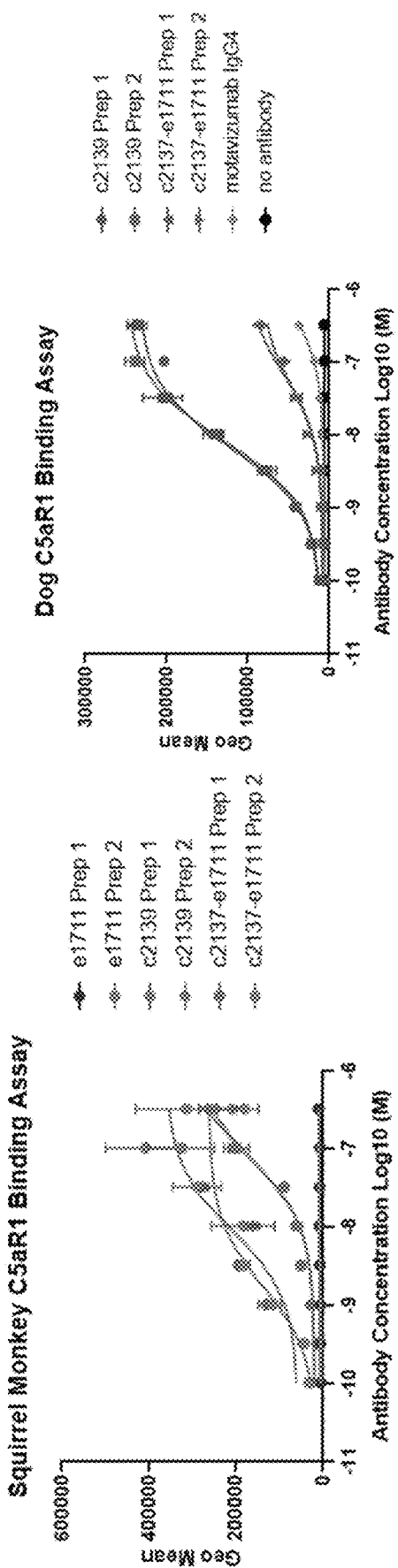
FIG. 13A is an exemplary graph showing binding (cross-reactivity) of exemplary humanized C5aR1 antibodies to squirrel monkeys
FIG. 13B is an exemplary graph showing binding (cross-reactivity) of exemplary humanized C5aR1 antibodies to dogs.

Cell surface binding and flow cytometry were performed on half-log titrations of anti-C5aR1 antibodies ranging from at $10^{-7.5}$ to $10^{-12}$ M. As shown in FIG. 13A-13B, the anti-C5aR1 humanized antibodies bound Squirrel monkey and dog C5aR1.

Example 10. Inhibition of Neutropenia in Squirrel Monkeys

This example shows the inhibition of neutropenia by C5aR1 antibodies in squirrel monkeys. Neutropenia is caused by rapid expression of cell surface CD11b which allows neutrophils to transiently adhere to blood vessel endothelium, thus reducing peripheral neutrophil counts. Squirrel monkey is a physiologically relevant model compared to mouse for evaluation of neutropenia, as neutrophil counts in squirrel monkeys are similar to humans (50-70%), mice have only 10-20%. Further, Squirrel monkey allows blood collection at multiple time points possible enabling longer study duration. It was further observed that cross-reacts with squirrel monkey C5aR1, as shown in FIG. 13A.

Figure 14A:
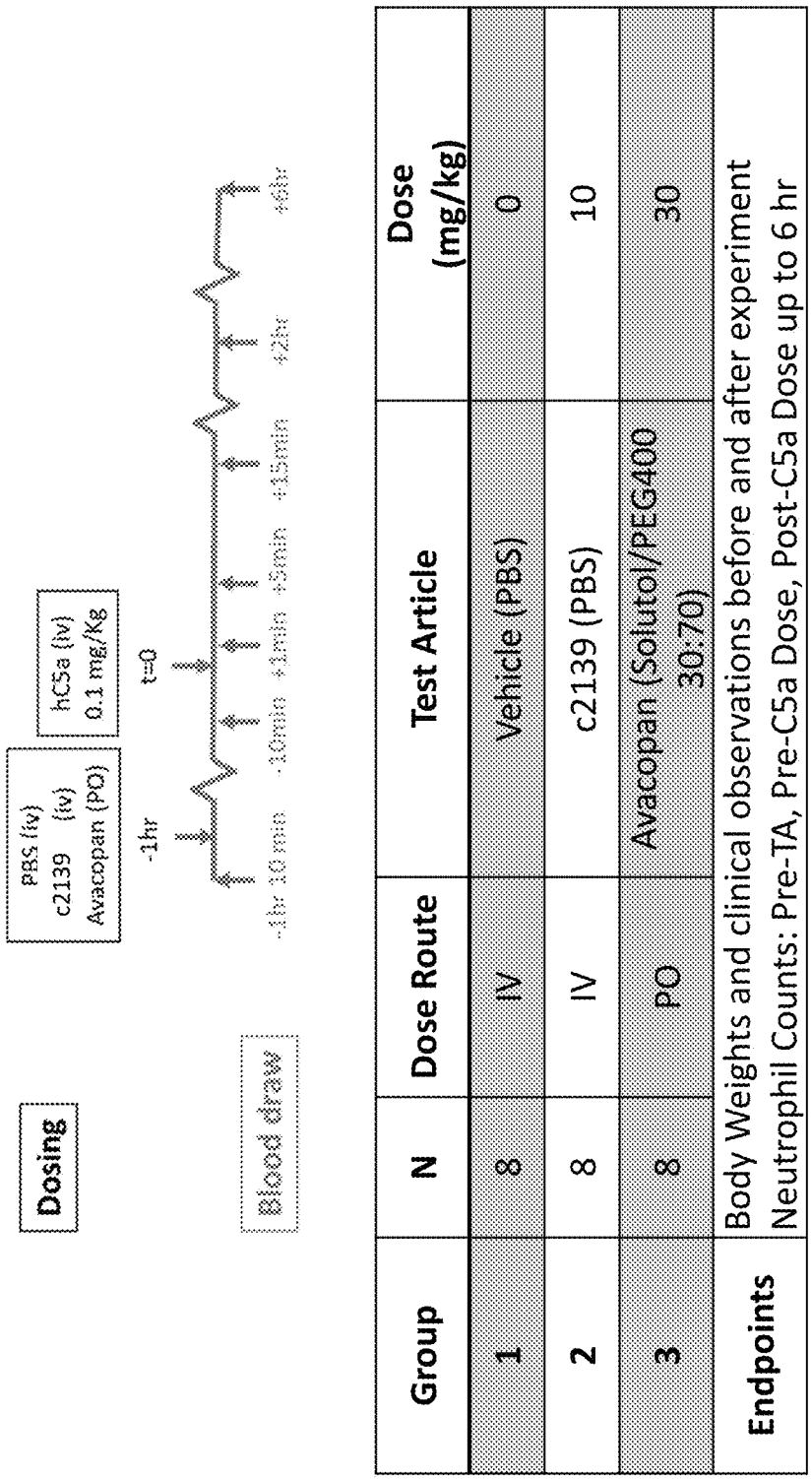
FIG. 14A is an exemplary schematic diagram of the study design in squirrel monkeys showing time of blood draw and dosing.
Figure 14C:
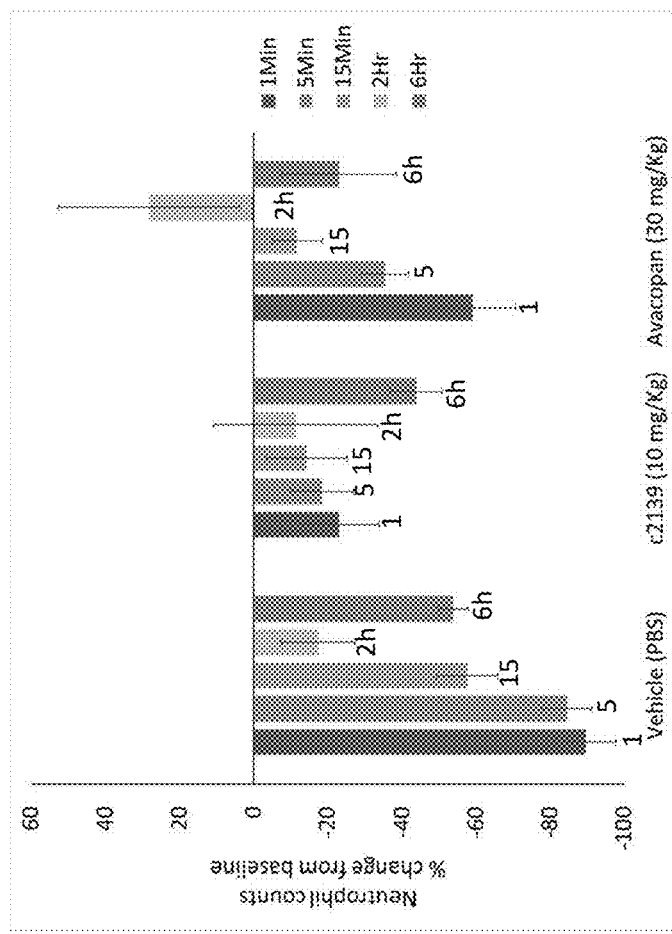
FIG. 14C is a bar graph of percent change in neutrophil counts from baseline in vehicle, an exemplary humanized Site II antibody and avacopan.
Figure 14B:
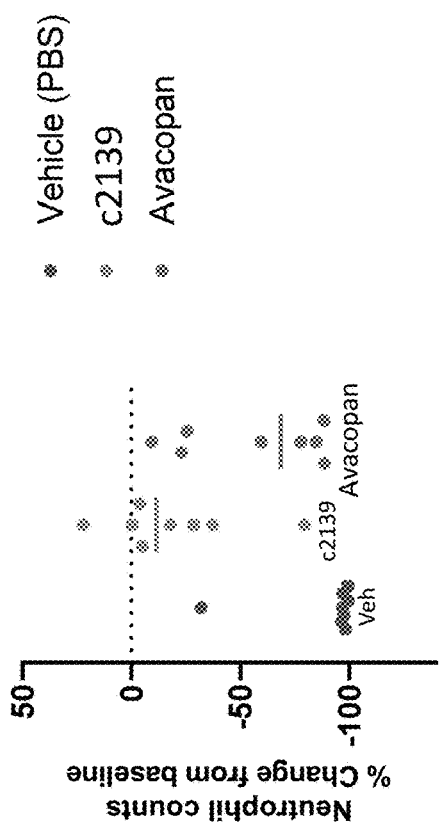
FIG. 14B is an exemplary scatter plot of percent change in neutrophil counts from baseline in vehicle, an exemplary humanized Site II antibody and avacopan.

FIG. 14A shows the experiment design in squirrel monkeys to evaluate alleviation of neutropenia. Briefly, three groups of squirrel monkeys were evaluated for inhibition of neutropenia. In the first group, 8 squirrel monkeys were injected with PBS (vehicle), intravenously. In the second group 8 squirrel monkeys were injected with exemplary antibodies at a dose of 10 mg/kg, intravenously. In the third group, group 8 squirrel monkeys were injected with avacopan at a dose of 30 mg/kg, intravenously. One hour after injection of the PBS, exemplary antibodies or avacopan, 0.1 mg/kg of human C5a was injected into the squirrel monkeys. The blood was collected after 1 min, 5 min 15 min, 2 hr and 6 hr after injection of human C5a. The percent change in neutrophils and average change in neutrophils were calculated in all three groups and are shown in FIG. 14B, as scatter plot. The average change in neutrophils are shown in FIG. 14C, as bar graph.

It was observed that administration of human C5a resulted in rapid transient neutropenia, caused by neutrophil adhesion to endothelial cells. The vehicle (PBS) group demonstrated robust neutropenia with 89% average reduction in neutrophil counts from baseline at 1 min post-C5a injection. Significant inhibition of neutropenia was observed on pre-treatment with exemplary anti-C5aR1 antibodies (23% vs 89% for vehicle). It was further observed that the neutrophil counts starts to resolve between 2 to 6 hours. Neutrophilia observed for Avacopan. No neutrophilia was observed for c2139. Avacopan group also responded with 59% average decrease in neutrophils. It was observed that exemplary anti-C5aR1 antibodies had superior response rate when compared to Avacopan.

Example 11. Inhibition of Neutropenia in Human C5aR1 Transgenic Mice

This example shows the inhibition of neutropenia by C5aR1 antibodies in transgenic human C5aR1 mice. The exemplary C5aR1 antibodies do not cross-react with mouse C5aR1. Transgenic human C5aR1 (hC5aR1) knock-in mice were generated using CRISPR technology at The Jackson Laboratory.

Figure 15C:
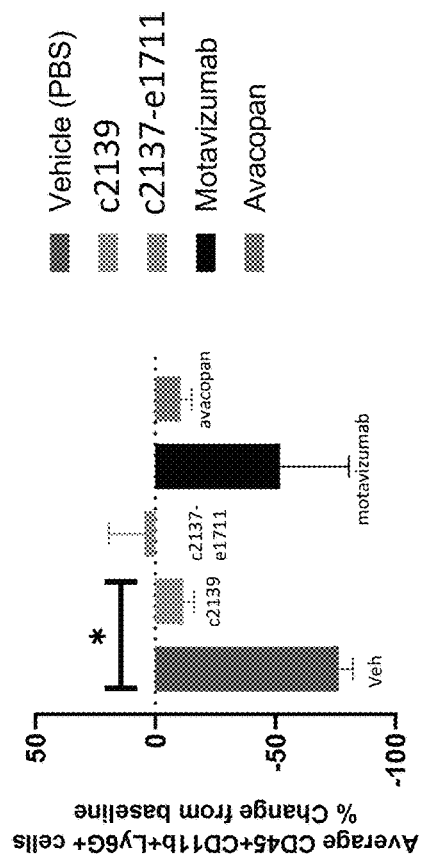
FIG. 15C is an exemplary bar graph of percent change in neutrophil counts from baseline in vehicle, humanized Site II antibody and avacopan.
Figure 15B:
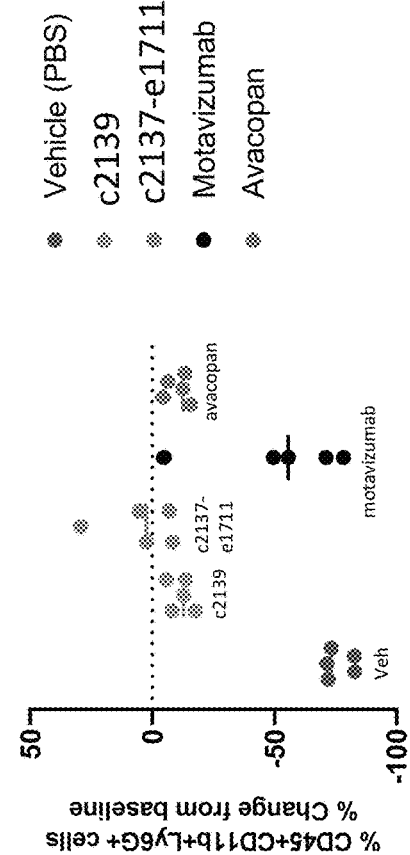
FIG. 15B is an exemplary scatter plot of percent change in neutrophil counts from baseline in vehicle, humanized Site II antibody and avacopan.

FIG. 15A shows the experiment design in mice to evaluate alleviation of neutropenia. Briefly, five groups of hC5aR1 mice were evaluated for inhibition of neutropenia. In the first group, 5 hC5aR1 mice were injected with PBS (vehicle), intravenously. In the second group 5 hC5aR1 mice were injected with exemplary monospecific anti-C5aR1 antibody, c2139, at a dose of 20 mg/kg, intravenously. In the third group, group 5 hC5aR1 mice were injected with exemplary biparatopic anti-C5aR1 antibody, c2137-e1711, intravenously at a dose of 20 mg/kg. In the fourth group, 5 hC5aR1 mice were injected with non-C5aR1 antibody (Motavizumab) intravenously at a dose of 20 mg/kg. In the fifth group, 5 hC5aR1 mice were injected with avacopan at a dose of 30 mg/kg, intravenously. One hour after injection of the PBS, exemplary antibodies, motavizumab or avacopan, 0.1 mg/kg of human C5a was injected into the hC5aR1 mice. The blood was collected after 1 min, 5 min and 2 hr after injection of human C5a. The percent chance in neutrophils and average change in neutrophils were calculated in all three groups and are shown in FIG. 15B-15C. The average change in neutrophils are shown in FIG. 15C. Neutrophil cell counts were assessed by gating CD45+/CD11b+/Ly6G+ cells.

It was observed that administration of human C5a resulted in rapid transient neutropenia, caused by neutrophil adhesion to endothelial cells. The vehicle (PBS) group demonstrated robust neutropenia with 89% average reduction in neutrophil counts from baseline at 1 min post-C5a injection. Significant inhibition of neutropenia was observed on pre-treatment with exemplary anti-C5aR1 antibodies (23% vs 89% for vehicle). Avacopan group also responded with 59% average decrease in neutrophils.

It was observed that exemplary anti-C5aR1 antibodies had superior response rate when compared to Avacopan. It was observed that administration of human C5a resulted in rapid transient neutropenia in human C5aR1 mice. The vehicle (PBS) group demonstrated robust neutropenia with 76% average reduction in neutrophil counts from baseline at 1 min post-C5a injection. Significant inhibition of neutropenia was observed on pre-treatment with exemplary monospecific C5aR1 antibody (11% vs 89% for vehicle). Complete inhibition was seen for exemplary biparatopic C5aR1 antibody. Avacopan group also responded with 10% average decrease in neutrophils.

Example 12. Pharmacokinetic Studies of Exemplary C5aR1 Antibodies in hC5aR1 Mice This example shows the pharmacokinetic (PK) studies of exemplary C5aR1 antibodies in mice.

Figure 16A:
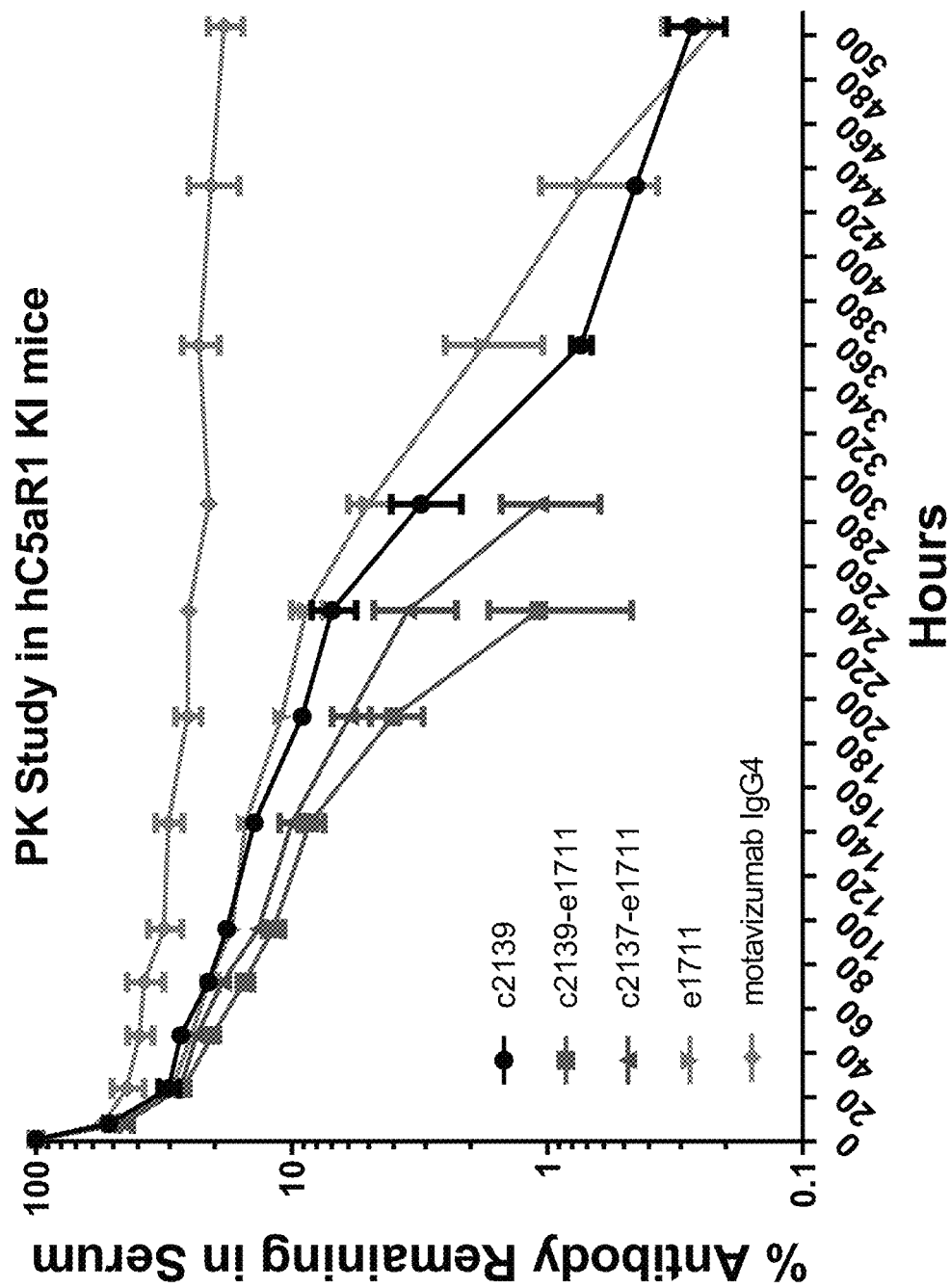
FIG. 16A is an exemplary graph showing 21-day PK profiles of exemplary tetravalent (biparatopic antibody) and monospecific antibodies.
Figures 16B, 16C, 16D:
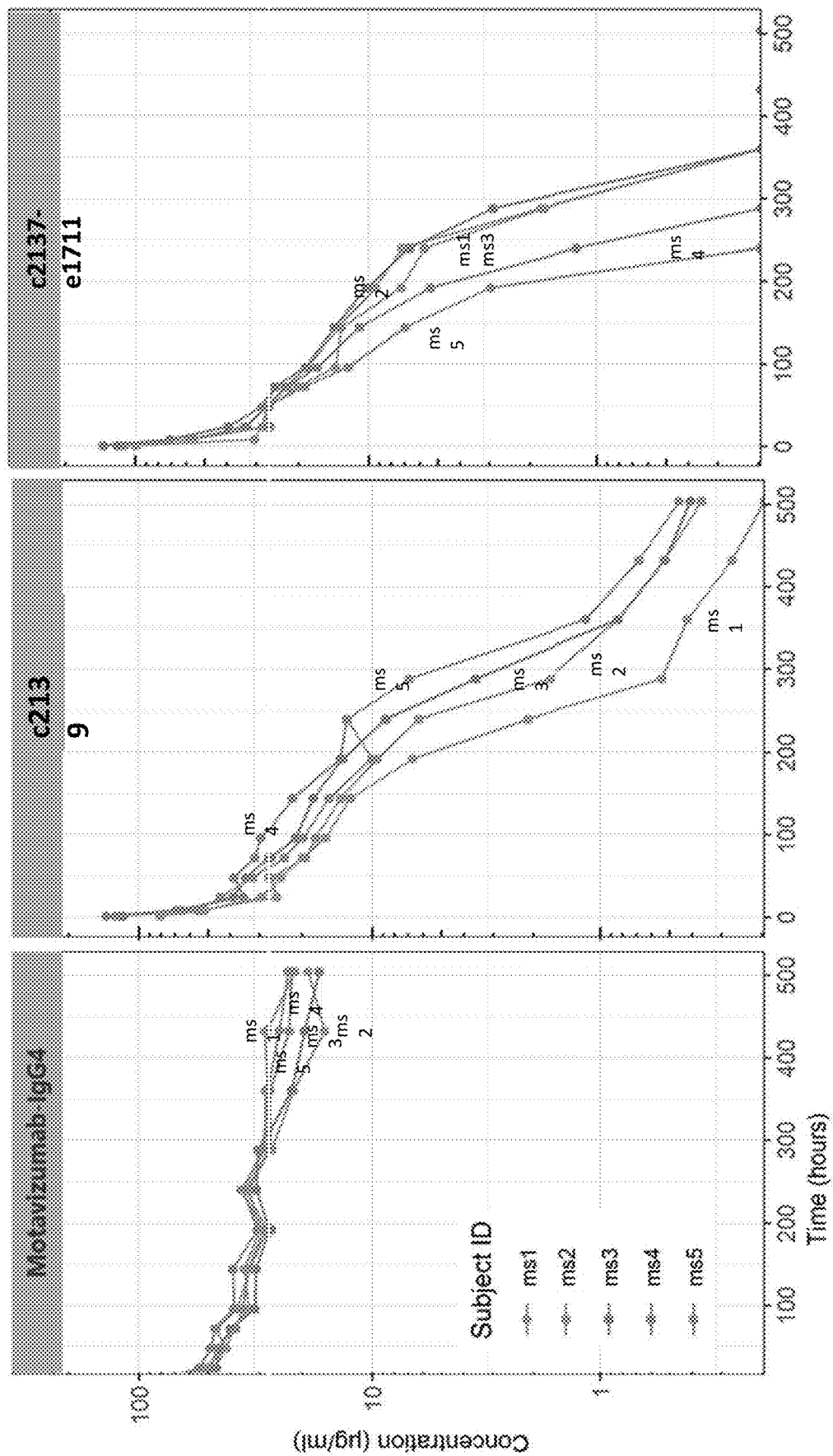
FIG. 16B is an exemplary graph showing 500 hour PK profile of Motavizumab in serum of mice.
FIG. 16C is an exemplary graph showing 500 hour PK profile of c2139 in serum of mice.
FIG. 16D is an exemplary graph showing 500 hour PK profile of c2137-e1711 in serum of mice.

5 mg/kg of exemplary monospecific and biparatopic antibodies were injected intravenously into Tg32 mice. The amount of the antibody in the serum was evaluated over a period of 500 hours. FIG. 16A shows the pharmacokinetic properties of exemplary antibodies. FIG. 16B-16D show the stability of the anti-C5aR1 antibodies in the serum of 5 different mice for 500 hours. It was observed that monospecific (c2139—FIG. 16C) and Biparatopic (c2137-e1711—FIG. 16D) antibodies were stable in serum and persist equivalently in Tg32 mice. In hC5aR1 transgenic mice, TMDD observed with both c2139 and c2137-e1711. The tetravalent antibodies have slightly lower persistence in serum as compared to the monospecific antibody. Motavizumab was used as a control.

Example 13. Prediction of Pharmacokinetic Studies of Exemplary C5aR1 Antibodies in Human Beings Non-linear PK was observed for known anti-C5aR1 antibodies (Lee et al, 2006, PMID 16980984). It was reported that >90% receptor occupancy was observed for 4.3 weeks with a 10 mg/kg IV dose and >90% receptor occupancy was observed for 1.8 weeks at a 4 mg/kg subcutaneous dose. Based on the affinity data of the instant humanized anti-C5aR1 antibodies, model simulations showed a non-linear clearance for between 0.1 to 10 mg/kg of antibody id predicted to result in >90% receptor occupancy for 24 days, following IV administration.

Notwithstanding bioavailability, it is predicted that a 4 mg/kg subcutaneous dosage is predicted to have a >90% receptor occupancy for about 7-13 days.

It was observed that the tetravalent antibodies (biparatopic) had slightly lower persistence in serum as compared to monospecific lead.

Example 14. Stability of Exemplary C5aR1 Antibodies at 4° C.

This example shows the stability of exemplary C5aR1 antibodies (both monospecific and biparatopic) at 4° C., with one thaw cycle in between.

Both monospecific and biparatopic antibodies were incubated at 4° C. for up to 14 days. After one thaw cycle at 37° C., the amount of intact antibodies were evaluated by gel filtration, native PAGE and dynamic light scattering (DLS). Table 10 shows percent antibody aggregates (HMW), compared to percent intact antibody.

TABLE 10

Stability of C5aR1 bispecific antibody after 1 freeze-thaw cycle at room temperature/37° C.

| Format | Sample Information | | | | T = 0 week | | T = 1 week | | T = 2 week | | 37 c. T1 day | | F/T 1 cycle | |
| | Date of Purification/ Actual Time point | Lot # | Sample Name | Temp | % HMW | % Main | % HMW | % Main | % HMW | % Main | % HMW | % Main | % HMW | % Main |
| --- | --- | --- | --- | --- | --- | --- | --- | --- | --- | --- | --- | --- | --- | --- |
| | Sep. 29, 2020 (1, 2, 3, 5 wk) | 10077 | c2139 | 2-8 C. RT | 11.7 | 88.3 | 11.2 10.6 | 88.8 89.4 | 10.7 10.1 | 89.4 89.9 | 10.0 | 90.1 | 9.7 | 90.3 |
| Tetravalent, scFv Format | Aug. 11, 2002 (8, 9, 10, 12 wk) | 9996 | c2137-e1711 | 2-8 C. RT | 8.5 | 91.5 | 8.4 8.4 | 91.6 91.6 | 8.3 8.3 | 91.7 91.7 | 8.1 | 91.9 | 8.1 | 91.9 |

It was observed that both monospecific and biparatopic antibodies were stable in 4° C. and RT up to 2 weeks and one Freeze/thaw cycle.

Example 15—Kinetic Analyses of C5aR1 Antagonistic Humanized Antibodies with Modified Fc Domain This Example describes the binding affinity and specificity of Site II monospecific antibody and biparatopic antibodies described herein, to C5aR1 and C5aR2 with modified Fc domain. The Fc domain modifications were introduced to counteract effector functions, such as ADCC or ADCP. Additionally, the modified Fc domain comprises mutation to prevent Fab arm exchange. Table 11 summarizes Fc modifications in C5aR1 antibodies.

TABLE 11

Summary of monospecific and biparatopic antibodies C5aR1 antibodies with modified Fc domains.

| | MONOSPECIFIC | BIPARATOPIC |
| --- | --- | --- |
| Name | c2139-$F_c$mod | c2137-e1711-$F_c$mod |
| $V_H$ region | $V_H$ region c2137 | $V_H$ region c2137-e1711 |
| Fc-silencing mutations | F234V, L235E, D265G | F234V, L235E, D265G |
| Fab-arm exchange mutation | S228P | S228P |

The binding affinity of monospecific and biparatopic antibodies with modified Fc domain were calculated as described in Example 1. The monospecific antibody with modified Fc domain is hereinafter called "c2139-$F_c$mod;" and the biparatopic antibody with modified Fc domain is hereinafter called "c2137-e1711-$F_c$mod."

(a) Binding Affinity

Figures 17A, 17B:
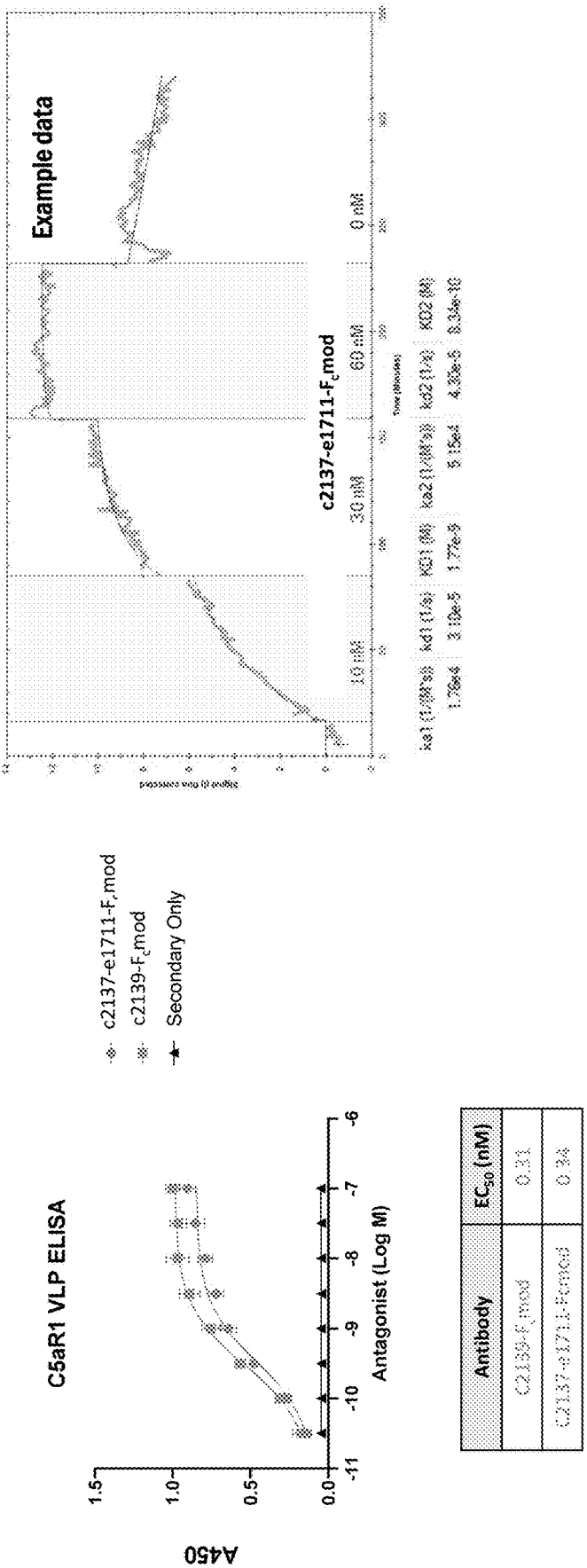
FIG. 17A is an exemplary graph showing affinity curves of a monospecific C5aR1 antibody (c2139-Fcmod) and a C5aR1 biparatopic antibody (c2137-e1711-$F_c$mod).
FIG. 17B is an exemplary graph showing kinetic parameters of C5aR1 biparatopic antibody (c2137-e1711-F$_c$mod).

Affinity curves of a monospecific C5aR1 antibody (c2139-Fcmod) and a C5aR1 biparatopic antibody (c2137-e1711-$F_c$mod) are illustrated in FIG. 17A.

It was observed that under the conditions described above, the monospecific C5aR1 monospecific antibody, c2139-Fcmod, bound C5aR1 with an affinity of about 0.31 nM and the C5aR1 biparatopic antibody, c2137-e1711-$F_c$mod, bound C5aR1 with an affinity of about 0.34 nM.

Exemplary kinetic assays for binding to C5aR1 expressing cells are shown in (FIG. 17B). Kinetic measures were fitted after a 2-3 dose association phase followed by dissociation. It was observed that EC50 of Fc modified antibodies were comparable to the EC50 of the Fc unmodified antibody. For example, as seen from Table 12, the EC50 of biparatopic antibody, c2137-e1711 and c2137-e1711-$F_c$mod were both about 1 nM in U937-C5aR1 cells, about 1 nM and 2 nM in Neutrophils and 0.5 nM and 0.6 mM in Macrophages.

TABLE 12

Comparison of EC50 of c2137-e1711 and c2137-e1711-$F_c$mod

| | U937-C5aR1 | Neutrophils | Macrophages |
| --- | --- | --- | --- |
| c2137-e1711-$F_c$mod | Kon: 2.6e4 (1/(M*s)) Koff: 3.4e-5 (1/s) KD: ~1 nM | Kon: 2.6e4 (1/(M * s)) Koff: 3.4e-5 (1/s) KD:~1 nM | Kon: 8.8e4 (1/(M * s)) Koff: 3.8e-5 (1/s) KD: ~0.5 nM |
| c2137-e1711 | Kon: 1.5e4 (1/(M*s)) Koff: 1.6e-5 (1/s) KD: ~1 nM | Kon: 6.9e3 (1/(M * s)) Koff: 2.0e-5 (1/s) KD: ~2 nM | Kon: 9.7e4 (1/(M * s)) Koff: 5.8e-5 (1/s) KD: ~0.6 nM |

(b) Binding Specificity

The specificity of the Fc-modified C5aR1 antagonistic antibodies was determined by measuring the affinity of anti-C5aR1 antibodies to C5aR2. This was determined as described in Example 1.

Figure 17C:
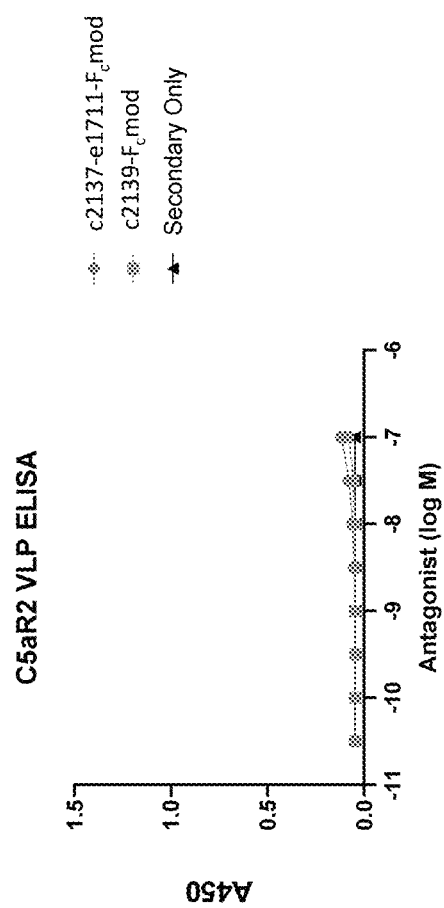
FIG. 17C is an exemplary graph showing binding of monospecific C5aR1 antibody (c2139-Fcmod) and a C5aR1 biparatopic antibody (c2137-e1711-F$_c$mod) to C5aR2.

FIG. 17C shows the affinity curves for determining the specificity of c2137-e1711-$F_c$mod and c2139-Fcmod. It was observed that the Fc modified antibodies did not display affinity for C5aR2.

Example 16—Internalization of C5aR1 Antibodies

Figures 18A, 18B:
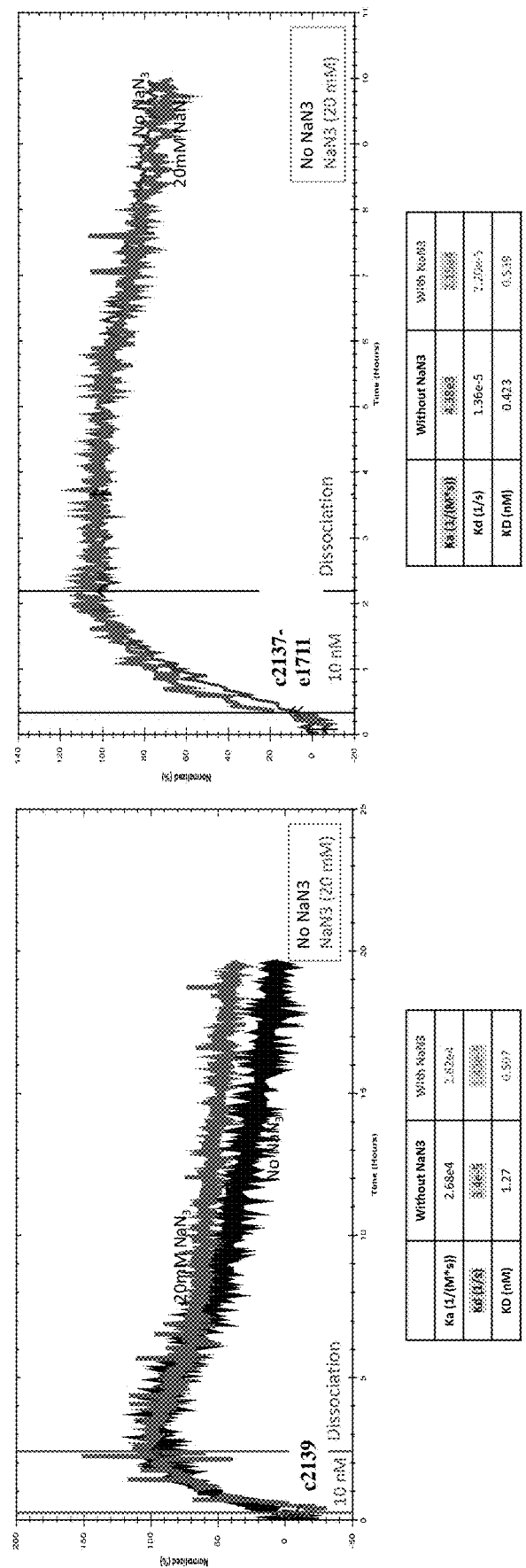
FIGS. 18A-18B demonstrate increase in internalization of the C5aR1 antibodies.

The Example seeks to verify that the internalization of the C5aR1 antibodies is specific and not due to non-specific clustering of the membrane immunoglobulin. Sodium azide is a metabolic inhibitor, and inhibits internalization or endocytosis as these are energy dependent processes. Any metabolic dependency on the internalization of exemplary C5aR1 antibodies were probed using 10 nM C5aR1 antibodies in the presence or absence of 20 mM sodium azide. It was observed that the exemplary C5aR1 antibodies underwent metabolic-based internalization. For example, c2139 underwent internalization several hours after dissociation and c2139-e1711 undergoes internalization during association. The dissociation constant of monospecific C5aR1 antibody, c2139, in the presence of 20 mM sodium azide was $1.43 \times 10^{-5}$ per second, while the dissociation constant without sodium azide was $3.4 \times 10^{-5}$ per second. The association constant of biparatopic C5aR1, c2137-e1711, in the presence of 20 mM sodium azide was $2.15 \times 10^4$ per mol per second, while the dissociation constant without sodium azide was $4.38 \times 10^3$ per mol per second. FIGS. 18A-18B demonstrate increase in internalization of the C5aR1 antibodies. FIG. 18A is an exemplary graph showing internalization several hours after dissociation of monospecific antibody, c2139. FIG. 18B is an exemplary graph showing increase in internalization of biparatopic antibody, c2137-e1711, during association.

It was observed that the non-specific clustering of the membrane immunoglobulin was not solely responsible for internalization of the exemplary c5aR1 antibodies.

Example 17—Inhibition of Gα Signaling by Fc Modified C5aR1 Antibodies

This Example describes the functional aspect of Fc modified C5aR1 monospecific antibodies and biparatopic antibodies described herein, for inhibition of Gα signaling using a GeneBLazer assay.

Figure 19B:
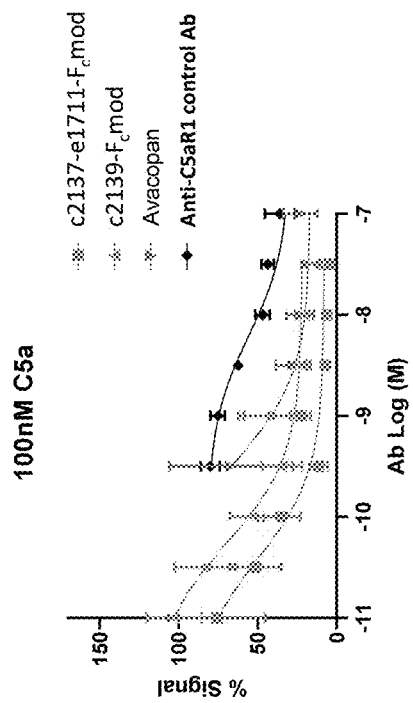
FIGS. 19A-19B illustrates inhibition of Ga signaling in the presence of C5aR1 Fc-modified antibodies.
Figure 19A:
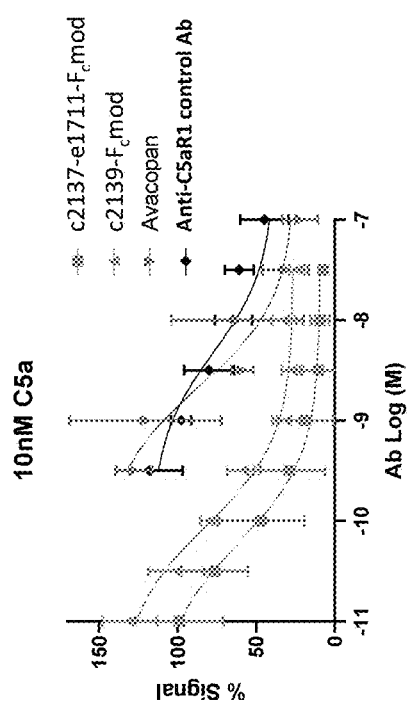

This experiment was done as detailed in Example 2. FIGS. 19A-19B shows the results of inhibition of Gα signaling in the presence of C5aR1 Fc-modified antibodies—c2137-e1711-$F_c$mod and c2139-$F_c$mod in comparison to Avacopan and anti-C5aR1 control Ab. It was observed that both c2137-e1711-$F_c$mod and c2139-Fcmod potently inhibited Gα signaling in a dose dependent manner.

Table 13 summarizes the inhibition compared to avacopan and anti-C5aR1 control Ab at 10 nM and 100 nM concentrations of C5a. It was observed that c2137-e1711-$F_c$mod and c2139-Fcmod retained superior inhibition compared to avacopan and anti-C5aR1 control Ab even at higher concentrations of C5a.

TABLE 13

Inhibition of c2137-e1711-$F_c$mod and c2139-$F_c$mod in the presence of C5a compared to avacopan and anti-C5aR1 control Ab

| Antagonist | IC50 (nM) | |
|---|---|---|
| | 10 nM C5a | 100 nM C5a |
| c2139-Fcmod | 0.09 | 0.05 |
| c2137-e1711-$F_c$mod | 0.06 | 0.04 |
| Avacopan | 2.2 | 0.7* |
| Anti-C5aR1 control Ab | 4.7 | 6.2 |

*Extrapolated data - previous data with avacopan suggests it is not very potent at high C5a concentration Example 18—Inhibition of Calcium Signaling by Fc Modified C5aR1 Antibodies This Example describes the functional aspect of C5aR1 Fc-modified monospecific antibodies and biparatopic antibodies described herein, for inhibition of C5a mediated calcium signaling, using calcium flux assays.

Figure 20B:
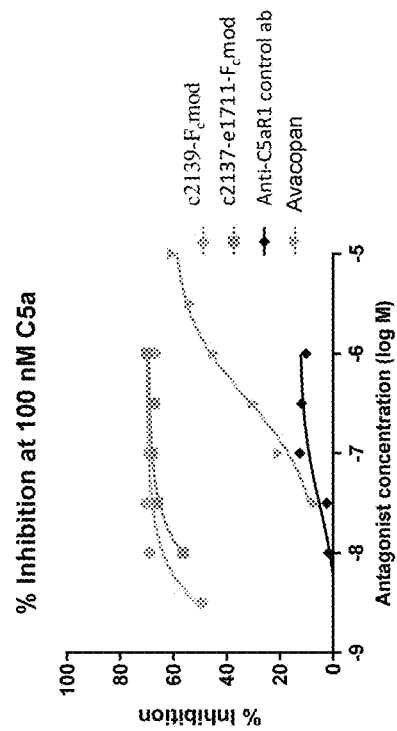
FIGS. 20A-20B is an exemplary series of graphs illustrating inhibition of Calcium signaling in the presence of C5aR1 Fc-modified antibodies—c2137-e1711-F$_c$mod and c2139-Fcmod in comparison to Avacopan and an anti-C5aR1 control Ab in U937-C5aR1 cells.
Figure 20A:
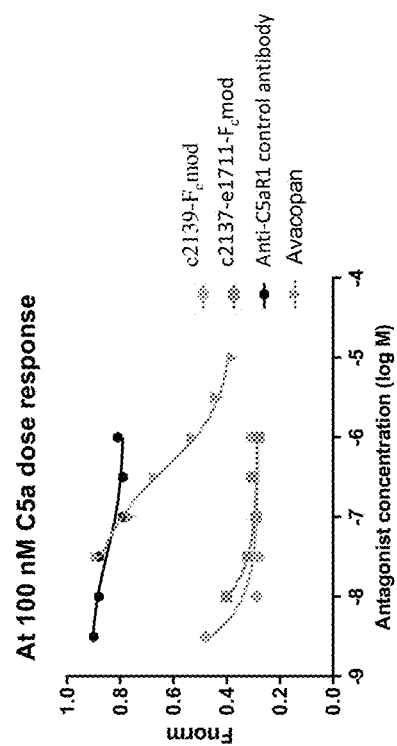

This experiment was done as described in Example 3. FIGS. 20A-20B show the results of inhibition of Calcium signaling in the presence of C5aR1 Fc-modified antibodies—c2137-e1711-$F_c$mod and c2139-$F_c$mod in comparison to Avacopan and anti-C5aR1 control Ab in U937-C5aR1 cells. It was observed that c2137-e1711-$F_c$mod and c2139-$F_c$mod more potently inhibited calcium flux than avacopan and anti-C5aR1 control Ab. It was observed that at least 10-100× were needed to reach inhibitory levels shown by c2137-e1711-$F_c$mod and c2139-$F_c$mod. It was observed that Fc modified C5aR1 antibodies inhibited calcium signaling in human neutrophils as well as U937-C5aR1 cells. FIG. 20A is a dose response curve showing the exemplary graph showing inhibition of calcium signaling using an exemplary Fc modified humanized Site II antibody, as described in this disclosure, in the presence of increasing concentrations of the antibody and 100 nM C5a. FIG. 20B is a percent inhibition graph showing inhibition of calcium signaling using an exemplary Fc modified humanized Site II antibody, as described in this disclosure, in the presence of the antibody and 100 nM C5a.

Figure 21A:
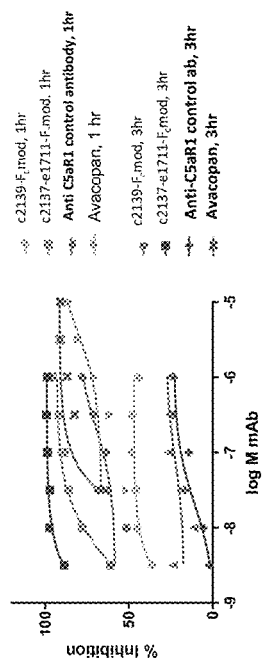
FIGS. 21A-21D show the inhibition of calcium signaling in U937-C5aR1 cells as compared to human neutrophils.
Figure 21B:
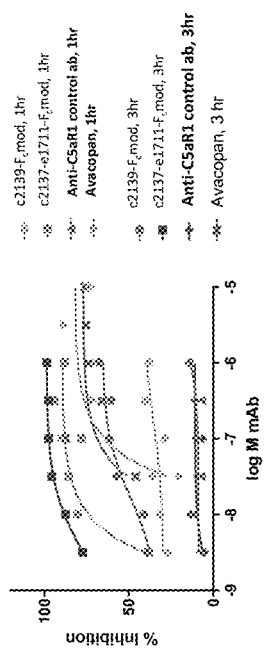
Figure 21C:
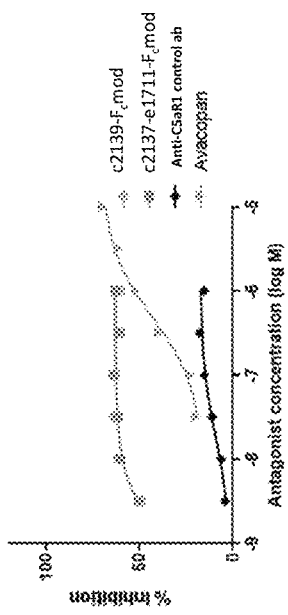
Figure 21D:
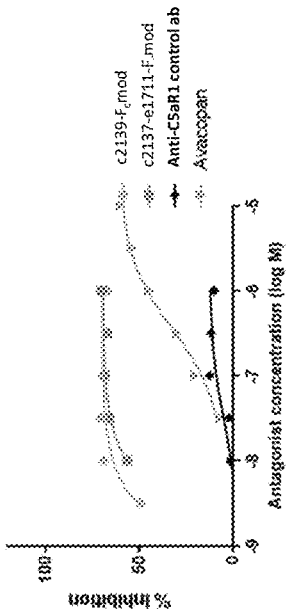

FIGS. 21A-21D shows the inhibition in U937-C5aR1 cells as compared to human neutrophils. FIG. 21A shows inhibition of calcium signaling in U937-C5aR1 cells in the presence of 10 nM C5a. FIG. 21B shows inhibition of calcium signaling in U937-C5aR1 cells in the presence of 100 nM C5a. FIG. 21C shows inhibition of calcium signaling in human neutrophils in the presence of 10 nM C5a. FIG. 21D shows inhibition of calcium signaling in human neutrophils in the presence of 100 nM C5a.

Figure 22A:
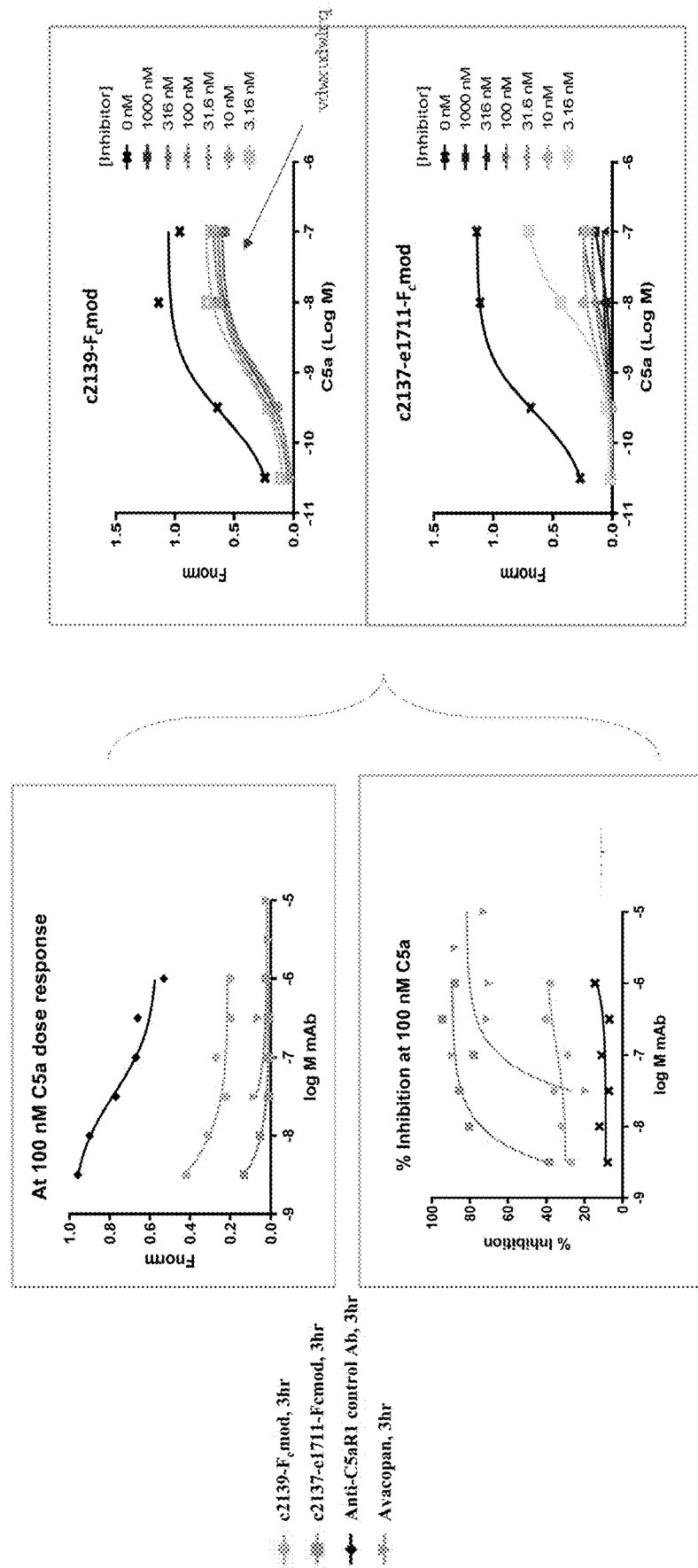
FIG. 22A summarizes percent saturation and F norm of U937-C5aR1 cells incubated with increasing concentrations of antibody, (c2139-Fcmod and c2137-e1711-Fcmod) and 100 nM C5a, after 1 hour incubation.
Figure 22B:
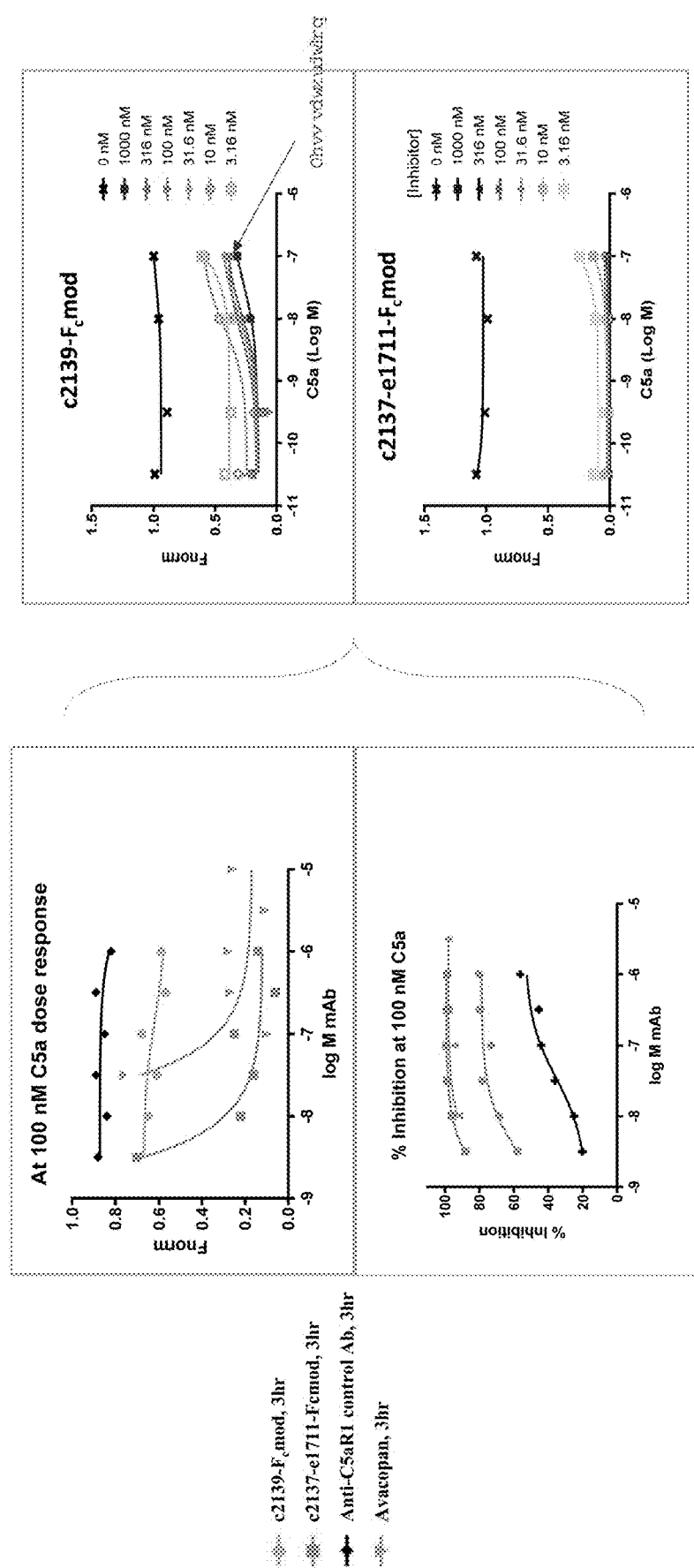
FIG. 22B summarizes percent saturation and F norm of U937-C5aR1 cells incubated with increasing concentrations of antibody, (c2139-Fcmod and c2137-e1711-Fcmod) and 100 nM C5a, after 3 hour incubation.

Further, the Fc modified antibodies were probed for inhibition of C5a mediated calcium signaling in U937-C5aR1 cells after incubation with indicated concentrations of the antagonistic antibodies at various incubation times (e.g., 1 hr and 3 hrs). FIGS. 22A-22B summarize the saturation levels of the U937-C5aR1 cells with each inhibitor. FIG. 22A summarizes percent saturation and F norm of U937-C5aR1 cells incubated with increasing concentrations of antibody, (c2139-$F_c$mod and c2137-e1711-$F_c$mod) and 100 nM C5a, after 1 hour incubation. FIG. 22B summarizes percent saturation and F norm of U937-C5aR1 cells incubated with increasing concentrations of antibody, (c2139-$F_c$mod and c2137-e1711-$F_c$mod) and 100 nM C5a, after 3 hour incubation.

FIG. 22A shows the inhibitory dose-response of calcium signaling by c2137-e1711-$F_c$mod and c2139-$F_c$mod. FIG. 22B shows the percent inhibition of calcium signaling by c2137-e1711-$F_c$mod and c2139-$F_c$mod.

It was observed that c2137-e1711-$F_c$mod was more potent than avacopan and anti-C5aR1 control Ab. Further, c2139-$F_c$mod reached a saturation point at short antagonist incubation times. This saturation is mitigated somewhat with longer antagonist incubation times. This phenomenon is only observed with c2139-$F_c$mod and was observed with the precursor c2139.

Example 19—Inhibition of β-Arrestin Signaling by Fc Modified C5aR1 Antibodies This Example describes the functional aspect of Fc-modified C5aR1 monospecific antibody, and biparatopic antibodies described herein, for inhibition of β-arrestin recruitment.

The experimental details of this determining β-arrestin recruitment are described in Example 6. FIGS. 23A-23B summarize the inhibition of C5a-meditated β-arrestin signaling by c2137-e1711-$F_c$mod and c2139-$F_c$mod. It was observed that c2137-e1711-$F_c$mod and c2139-$F_c$mod more potently blocked β-arrestin recruitment to C5aR1 than avacopan and anti-C5aR1 control Ab. Table 14 summarizes the $K_D$ of inhibition of β-arrestin recruitment.

TABLE 14

$K_D$ of beta-arrestin inhibition

| Antagonist | IC50 (nM) at 100 nM C5a |
|---|---|
| c2139-Fcmod | 1.9 |
| c2137-e1711-$F_c$mod | 0.5 |
| Avacopan | 34 |
| Anti-C5aR1 control Ab | 12.7 |

Example 20—Inhibition of Neutrophil Chemotaxis by Fc Modified C5aR1 Antibodies This Example describes the functional aspect of Fc-modified C5aR1 monospecific antibodies and biparatopic antibodies described herein, for inhibition of neutrophil chemotaxis, which is known to be induced by C5aR1 activity, using a Boyden Chamber.

Figures 24A, 24B, 24C, 24D:
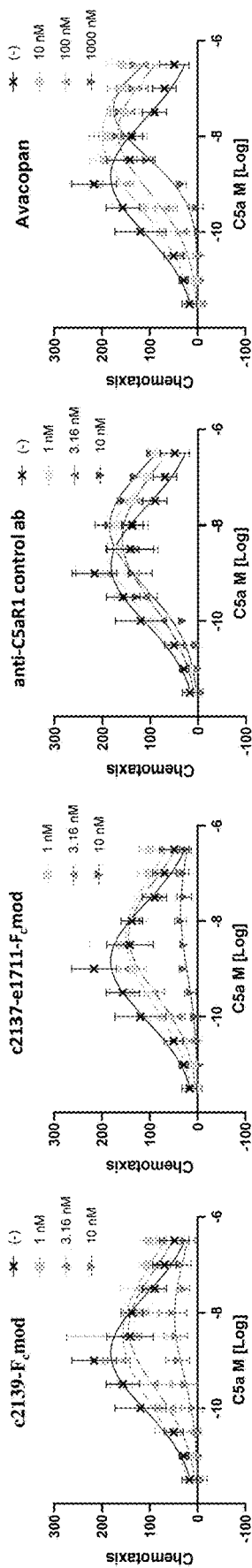
FIGS. 24A-24D show the inhibition of chemotaxis in C5aR1-U937 stable cells after treatment with C5aR1 antibodies, c2137-e1711-F$_c$mod and c2139-Fcmod, as compared to Avacopan and anti-C5aR1 control Ab.

The experimental details of this determining neutrophil chemotaxis are described in Example 4. FIGS. 24A-24D show the inhibition of chemotaxis in C5aR1-U937 stable cells after treatment with C5aR1 antibodies, c2137-e1711-$F_c$mod and c2139-$F_c$mod. It was observed that c2137-e1711-Fcmod and c2139-$F_c$mod more potently inhibited chemotaxis than avacopan and anti-C5aR1 control Ab. FIG. 24A shows the inhibition of chemotaxis in C5aR1-U937 stable cells in the presence of 1 nM, 3.16 nM and 10 nM c2139-$F_c$mod and increasing concentration of C5a. FIG. 24B shows the inhibition of chemotaxis in C5aR1-U937 stable cells in the presence of 1 nM, 3.16 nM and 10 nM C5a c2137-e1711-$F_c$mod and increasing concentration of C5a. FIG. 24C-24D shows the inhibition of chemotaxis in C5aR1-U937 stable cells in the presence of 1 nM, 3.16 nM and 10 nM anti-C5aR1 control Ab and Avacopan, respectively, in the presence of c2137-e1711-$F_c$mod.

Example 21—Inhibition of CD11b Expression by Fc Modified C5aR1 Antibodies

This Example describes the functional aspect of Fc-modified C5aR1 monospecific antibodies and biparatopic antibodies described herein, for inhibition of CD11b expression.

Figures 25A, 25B:
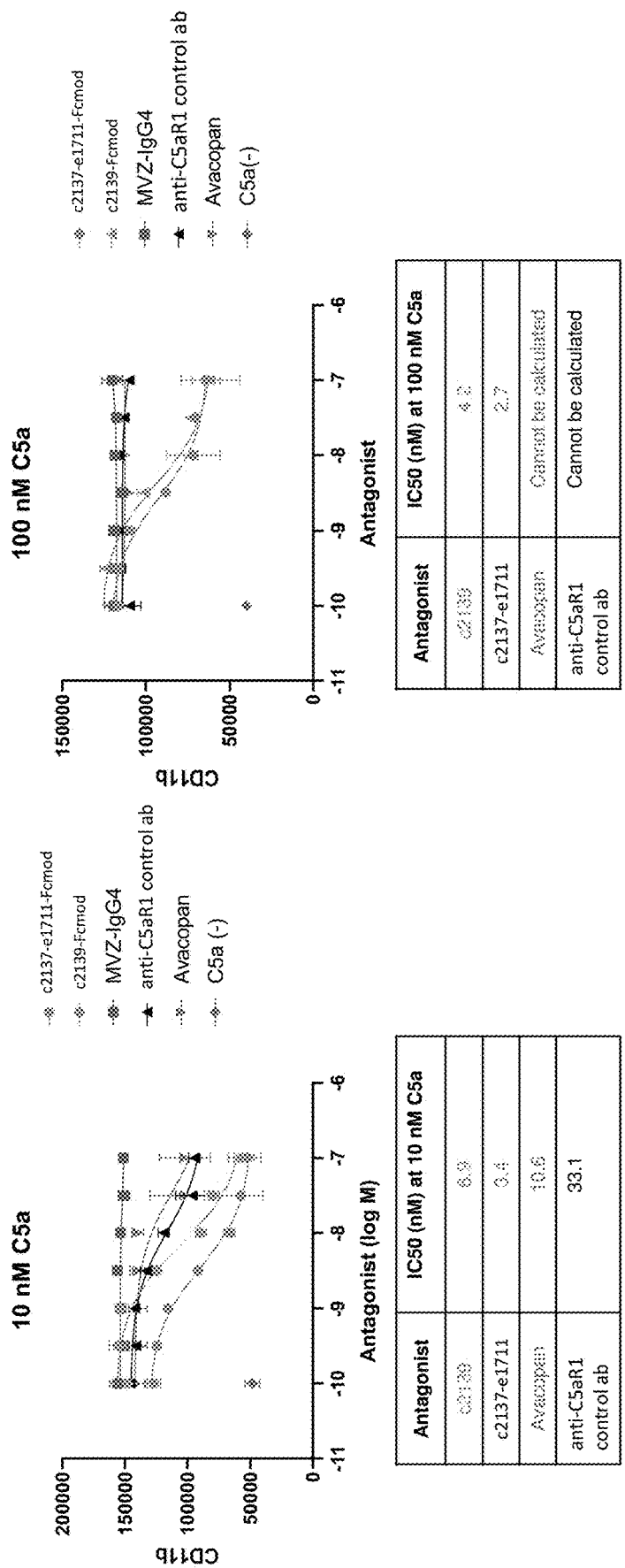
FIGS. 25A-25B show the inhibition of CD11b signaling in response to treatment with c2137-e1711-F$_c$mod and c2139-F$_c$mod.

The experimental details of this determining CD11 expression are described in Example 5. FIGS. 25A-25B show the inhibition of CD11b signaling in response to treatment with c2137-e1711-$F_c$mod and c2139-$F_c$mod. It was observed that c2137-e1711-$F_c$mod and c2139-$F_c$mod potently inhibited CD11b expression across the wide range of C5a concentrations, compared to avacopan and anti-C5aR1 control Ab. FIG. 25A shows the inhibition of CD11b signaling in the presence of increasing concentration of C5aR1 antagonistic antibody and 10 nM C5a. FIG. 25B shows the inhibition of CD11b signaling in the presence of increasing concentration of C5aR1 antagonistic antibody and 100 nM C5a.

Example 22—Inhibition of ROS Production by Fc Modified C5aR1 Antibodies

This example shows that exemplary humanized Fc-modified monospecific antibodies (c2139-$F_c$mod) and exemplary biparatopic antibodies (c2137-e1711-$F_c$mod) reduced reactive oxygen species (ROS).

Figure 26B:
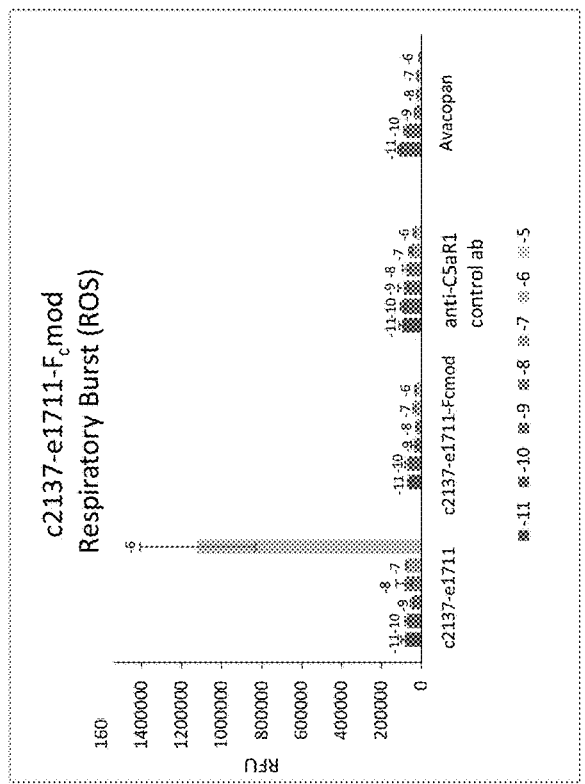
FIGS. 26A-26B show inhibition of ROS signaling in ANCA(−) and ANCA (+) cells as compared to c2139-F$_c$mod, c2137-e1711-F$_c$mod, motavizumab and Avacopan.
Figure 26A:
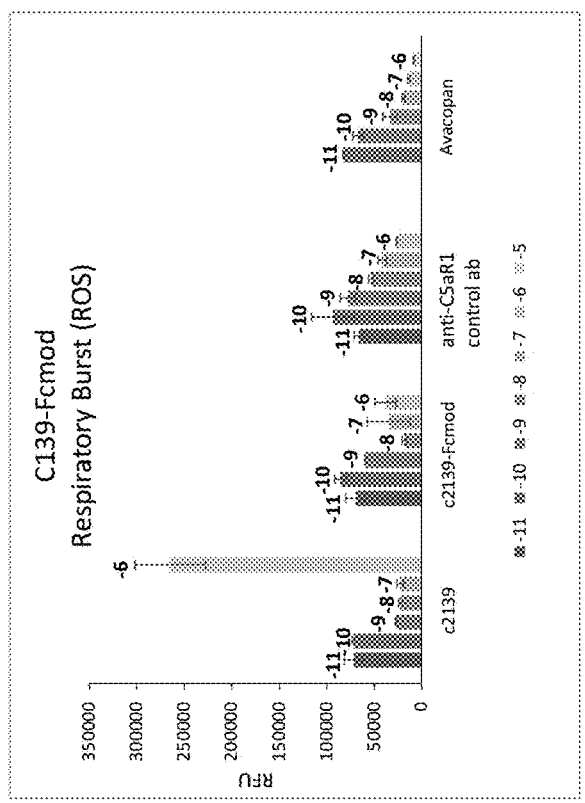

The experimental details of this determining ROS production are described in Example 7. FIGS. 26A-26B shows the inhibition of ROS production in The RBC-lysed WB cells treated with c2139-$F_c$mod, c2137-e1711-$F_c$mod, compared to c2139, c2137-e1711, anti-C5aR1 control Ab and avacopan. It was observed that c2139-$F_c$mod, and c2137-e1711-$F_c$mod maintained low respiratory burst activity in neutrophils, similar to avacopan and anti-C5aR1 control Ab. Further, c2139-$F_c$mod, and c2137-e1711-$F_c$mod had reduced respiratory burst activity compared to previous forms c2139, and c2137-e1711. FIG. 26A shows inhibition of ROS production of increasing concentration of monospecific C5aR1 antibody (Fc modified). FIG. 26B shows inhibition of ROS production of increasing concentration of biparatopic C5aR1 antibody (Fc modified).

Example 23. Inhibition of Neutropenia in Human C5aR1 Transgenic Mice by Fc Modified C5aR1 Antibodies This example shows the inhibition of neutropenia by Fc-modified C5aR1 antibodies in transgenic human C5aR1 mice. As described above (Example 11), the exemplary C5aR1 antibodies do not cross-react with mouse C5aR1. Transgenic human C5aR1 (hC5aR1) knock-in mice were generated using CRISPR technology at The Jackson Laboratory.

Figure 27A:
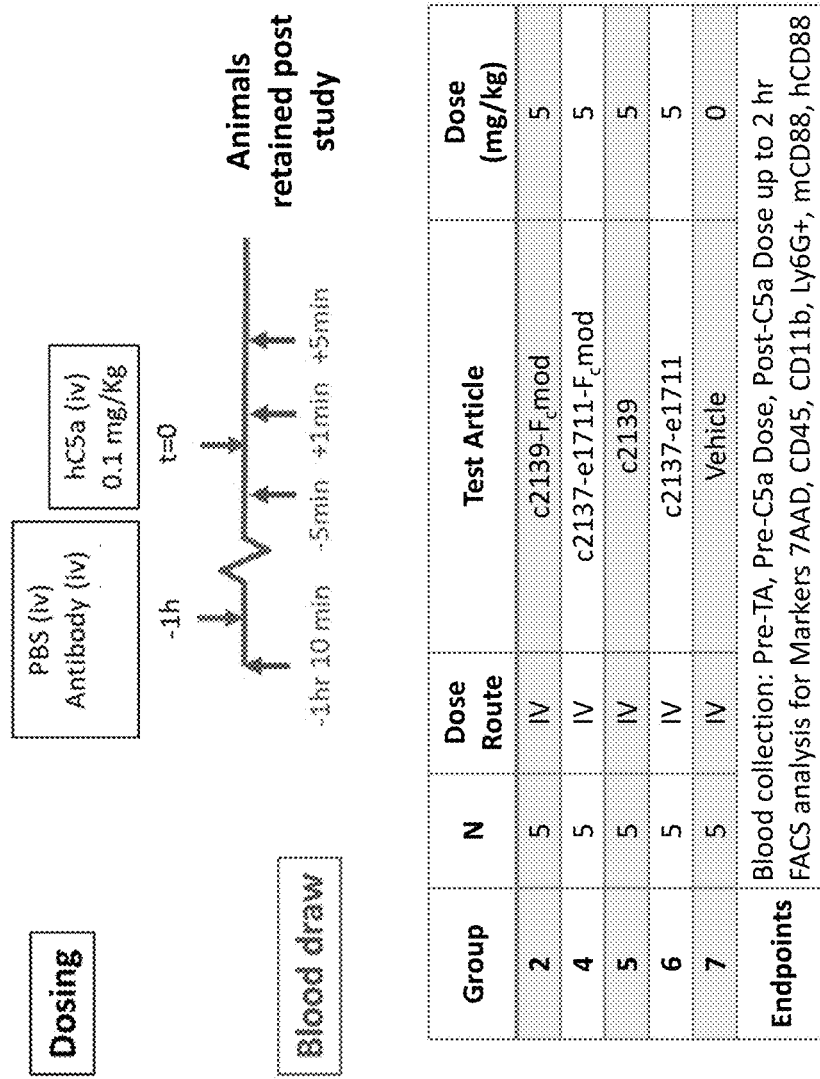
FIG. 27A is an exemplary schematic diagram of the study design in hC5aR1 mice showing time of blood draw and dosing.
Figure 27C:
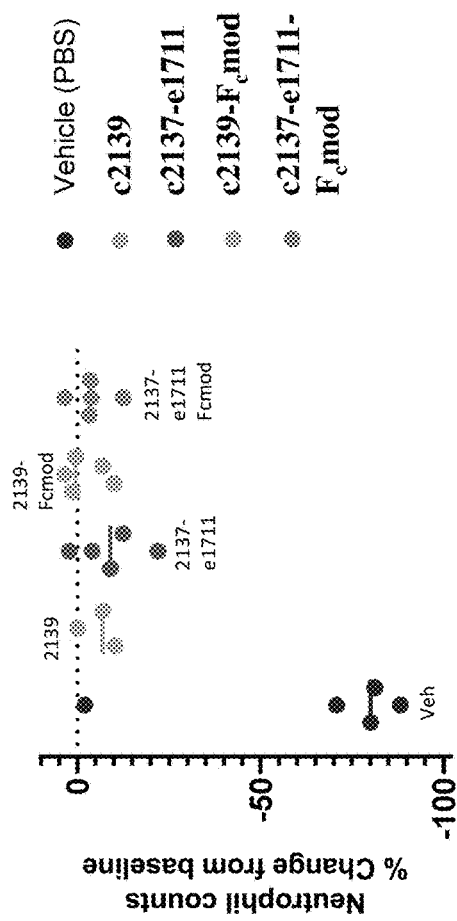
FIG. 27C is an exemplary bar graph of percent change in neutrophil counts from baseline in vehicle, c2139, c2139-Fcmod, c2137-e1711, and c2137-e1711-Fcmod.
Figure 27B:
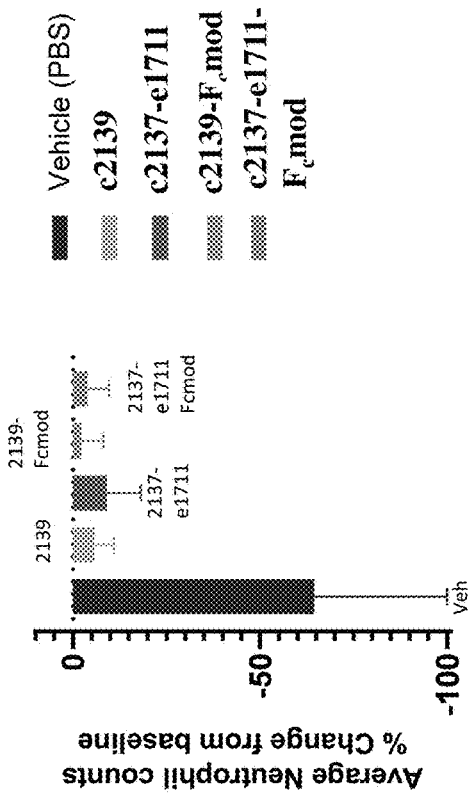
FIG. 27B is an exemplary scatter plot of percent change in neutrophil counts from baseline in vehicle, c2139, c2139-Fcmod, c2137-e1711, and c2137-e1711-Fcmod.

FIG. 27A shows the experiment design in mice to evaluate alleviation of neutropenia. The experimental details of this mouse in vivo assay are described in Example 11. The percent chance in neutrophils and average change in neutrophils were calculated in all groups and are shown in FIG. 27B-27C. The average change in neutrophils are shown in FIG. 27B. Change in neutrophil counts are shown in FIG. 27C. It was observed that the new Fc-silenced leads were just as potent as non-silenced c2139, and c2137-e1711. The vehicle (PBS) group demonstrated robust neutropenia with 65% average reduction in neutrophil counts from baseline at 1 min post-C5a injection. One animal did not respond to C5a in the Vehicle control group.

Example 24. Protection of Stroke in a Mouse Model

This Experiment demonstrated the ability of c2139-$F_c$mod, and c2137-e1711-$F_c$mod to protect infract volume in a stroke mouse model. Neutrophil activity and infiltration to the brain are well documented in stroke and traumatic brain injury pathology, including in acute models.

20 mg/kg of each, c2139-$F_c$mod, and c2137-e1711-$F_c$mod, were administered in tMCAO mice. 1 mg/kg PMX53 was used as a control. The brain was resected, cut into slices and stained with TTC. The stained cross sections were analyzed by imaging.

Figure 28B:
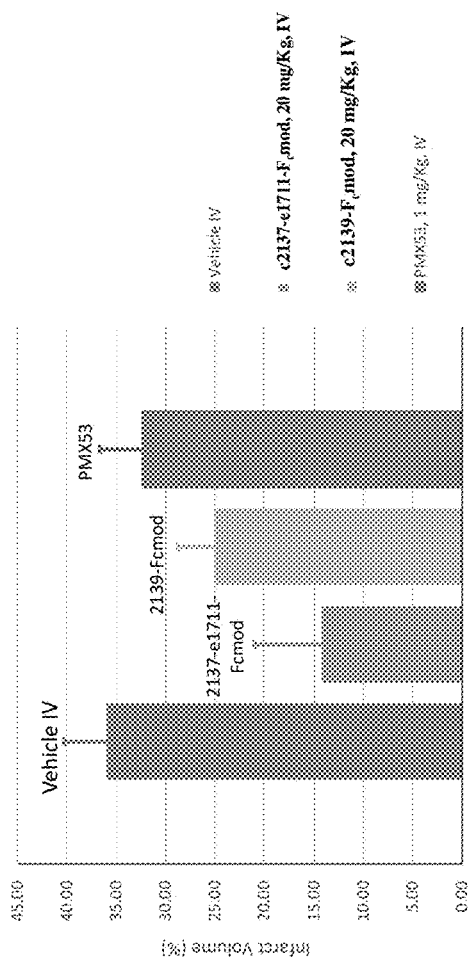
FIG. 28B is a graphical representation of infarct size in mouse brain after treatment with indicated doses of Fc modified antibodies as compared to 1 mg/kg PMX53.
Figure 28A:
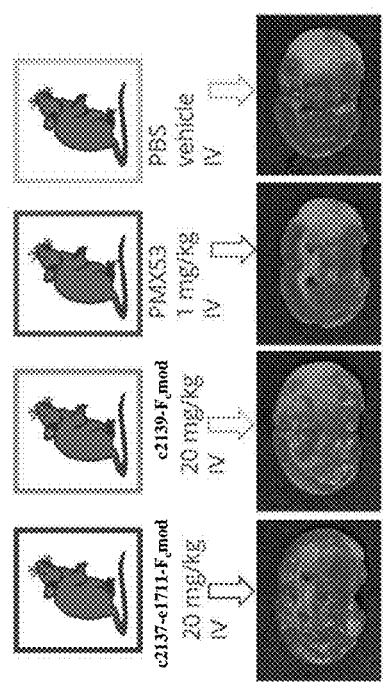
FIG. 28A is a pictorial representation of infarct size in mouse brain after treatment with indicated doses of Fc modified antibodies as compared to 1 mg/kg PMX53.

It was observed that mice treated with c2139-$F_c$mod, and c2137-e1711-$F_c$mod provided protection against stroke by significantly reducing the infarct volume, compared to the vehicle. c2137-e1711-$F_c$mod treatment showed significantly reduced infarct volume compared to the vehicle group. c2139-$F_c$mod treatment showed reduced infarct volume compared to the vehicle group. PMX53 treatment (serving as a positive control and comparator) showed only slightly reduced infarct volume compared to the vehicle group. FIG. 28A shows a pictorial representation of the reduction in the infract volume. FIG. 28B shows a graphical representation of the infarct volume after treatment with c2139-$F_c$mod, c2137-e1711-$F_c$mod and PMX53.

Example 25. Pharmacokinetic Studies of Exemplary C5aR1 Antibodies in hC5aR1 Mice with Modified Fc Domains This example shows the pharmacokinetic (PK) studies of exemplary C5aR1 with modified Fc domains antibodies in mice. Tg32 mice are a transgenic model in which human FcRn replaces native mouse FcRn. FcRn is necessary for the bidirectional transport of Abs across cellular barriers, influencing PK. Tg32 mice with human FcRn have been extensively studied and thought to correlate with PK in humans. The goal of this experiment was to assess FcRn-mediated recycling of IgG-scFv vs IgG formats and assess any impact of introducing Fc domain modifications on FcRn mediated recycling.

5 mg/kg of exemplary monospecific and biparatopic antibodies were injected intravenously into Tg32 mice. The percentage of antibody in the serum was determined using art-recognized assays. MVZ-IgG4-VFc17, a motavizumab antibody with IgG4 Fc and same Fc modifications as the C5aR1 antibodies, was used as a control. Further PK/PD analyses were carried out using CERTARA.

It was observed that C-max (the highest concentration of the antibodies in blood was similar for both monospecific and biparatopic antibodies). Further, it was observed that the half-life of the antibodies were similar for c2139-$F_c$mod, and c2137-e1711-$F_c$mod.

The amount of the antibody in the serum was evaluated over a period of 500 hours. Table 15 shows the dosage and the sampling intervals for the pharmacokinetic studies.

TABLE 15

Dosing and sampling schedule for exemplary C5aR1 Fc modified antibodies to determine the pharmacokinetics for individual antibodies.

| Antibody | Dose (mg/Kg) | N | Blood sampling |
|---|---|---|---|
| c2139-$F_c$mod | 5 | 5 | 1 h, 8 h, 1 d, 2 d, 3 d, |
| c2137-e1711-$F_c$mod | 5 | 5 | 4 d, 6 d, 8 d, 10 d, |
| MVZ-IgG4-VFc17 | 5 | 5 | 12 d, 15 d, 18 d, 21 d |

FIGS. 29A-29B shows the pharmacokinetic properties of C5aR1-Fc modified antibodies. FIG. 29A is a graphical representation of the percentage of the Fc modified C5aR1 antibodies in the blood serum for 500 hours. FIG. 29B is a graphical representation of mean concentration in μg antibody/ml of serum over 500 hours. These observations showed that c2137-e1711-$F_c$mod efficiently engaged with hFcRn and recycled in a manner similar to c2139-$F_c$mod. Further, the PK data were also similar to the PK of C5aR1 antibodies with unmodified Fc domains. Table 16 shows the PK parameters for the exemplar Fc-modified C5aR1 antibodies.

TABLE 16

Pharmacokinetic parameters of Fc modified C5aR1 antibodies.

| Ab | Dose | $C_{max}$ (μg/ml) | $t_{last}$ (h) | $AUC_{0-24}$ (μg * h/ml) | $AUC_{last}$ (μg * h/ml) | $AUC_{inf}$ (μg * h/ml) | $t_{1/2}$ (h) | CL (ml/h/kg) | V (ml/kg) |
|---|---|---|---|---|---|---|---|---|---|
| | | | | GeoMean (Geo CV %) | | | | | |
| c2139-Fcmod | 5 mg/kg | 52.6 (29.1%) | 504 (504-504)* | 904 (26.4%) | 9230 (8.3%) | 11100 (17.3%) | 229 (89.2-242)* | 0.449 (17.3%) | 118 (38.2%) |
| c2137-e1711-Fcmod | 5 mg/kg | 40.8 (30.1%) | 504 (504-504)* | 699 (18%) | 7550 (23.2%) | 9500 (38.9%) | 221 (67.1-390)* | 0.526 (38.9%) | 135 (45.1%) |
| Isotype CTL | 5 mg/kg | 131 (29.2%) | 504 (504-504)* | 1620 (7.7%) | 13100 (7.5%) | 16900 (10.4%) | 259 (200-270)* | 0.295 (10.4%) | 104 (7.4%) |

*Value presented as Median (Min-Max)

Example 26—Multi-Dose Pharmacokinetics of Fc-Modified C5aR1 Antibodies in Human C5aR1 Knock-In Mice This example shows the multi-dose pharmacokinetic (PK) studies of exemplary C5aR1 antibodies with modified Fc domains antibodies hC5aR1 mice.

Table 17 summarizes the dosage regimen of the antibodies being tested. Target-Mediated Drug Disposition (TMDD) is evident for both exemplary C5aR1 antibodies with modified Fc domains. TMDD is the phenomenon in which a drug binds with high affinity to its pharmacological target site (such as a receptor) to such an extent that this affects its pharmacokinetic (PK) characteristics. The target binding and subsequent elimination of the drug-target complexes could affect both drug distribution and elimination, and result in nonlinearity of PK in a dose-dependent manner.

TMDD is most observed as linear PK at high dose levels and nonlinear PK at low dose levels Dose-dependent clearance was observed as is expected for an antibody with TMDD. At 5 mg/Kg, and 0.5 mg/Kg, maximum concentration of each antibody, $C_{max}$ was found to be similar for both antibodies. Further, at 5 mg/Kg, and 0.5 mg/Kg, half-life of each antibody, ($T_{0.5}$), was found to be similar. At 20 mg/kg, c2139 had a better half-life, ($T_{0.5}$), than c2137-e1711.

TABLE 17

Dosing and sampling schedule for exemplary C5aR1 Fc modified antibodies to determine the pharmacokinetics for individual antibodies.

| Group | Antibody | Dose (mg/Kg) | N | Blood sampling |
|---|---|---|---|---|
| 1 | c2139-Fcmod | 0.5 | 4 | 1 h, 8 h, 1 d, 2 d, |
| 2 | c2139-Fcmod | 5 | 4 | 3 d, 4 d, 6 d, 8 d, |
| 3 | c2139-Fcmod | 20 | 4 | 10 d, 12 d, 15 d, |
| 4 | c2137-e1711-Fcmod | 0.5 | 4 | 18 d, 21 d |
| 5 | c2137-e1711-Fcmod | 5 | 4 | |

TABLE 17-continued

Dosing and sampling schedule for exemplary C5aR1 Fc modified antibodies to determine the pharmacokinetics for individual antibodies.

| Group | Antibody | Dose (mg/Kg) | N | Blood sampling |
|---|---|---|---|---|
| 6 | c2137-e1711-Fcmod | 20 | 4 | |
| 7 | MVZ-IgG4-VFc17 | 20 | 4 | |

Figure 30C:
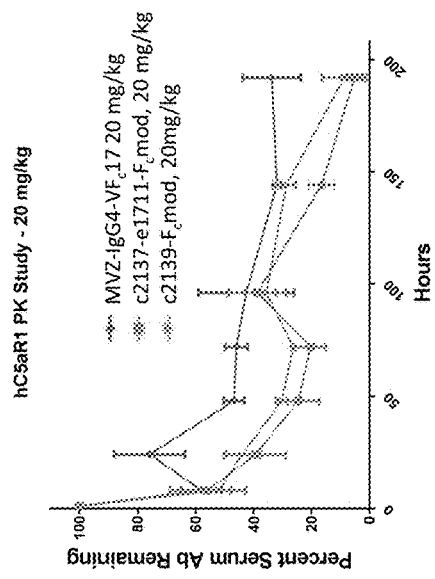
Figure 30B:
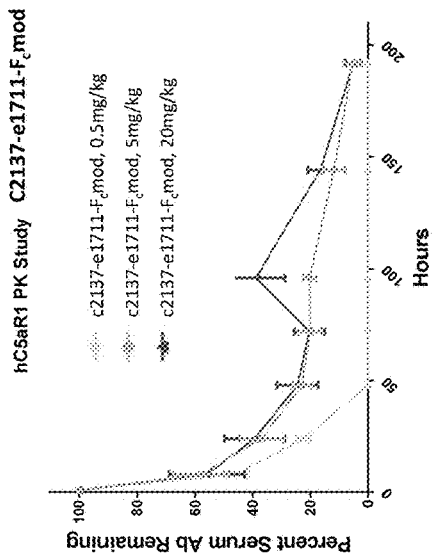
Figure 30A:
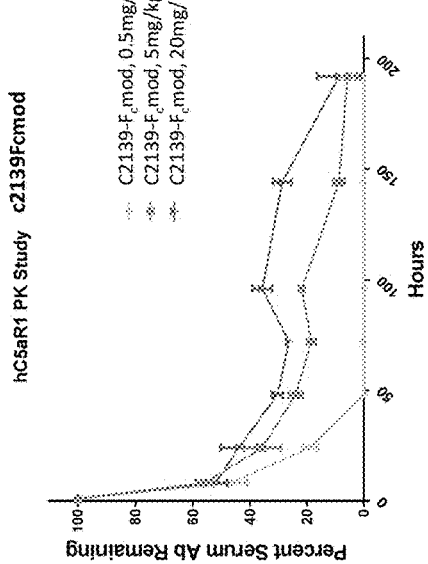

The target binding and subsequent elimination of the drug-target complexes could affect both drug distribution and elimination, and result in nonlinearity of PK in a dose-dependent manner. FIG. 30A-30F show antibody persistence was dose-dependent. Table 18 shows the PK parameters for the exemplar Fc-modified C5aR1 antibodies. FIG. 30A is a graphical representation of a dose response curve of c2139-Fcmod in serum for 200 hours. FIG. 30B is a graphical representation of a dose response curve of c2137-e1711-Fcmod in serum for 200 hours. FIG. 30C is a comparison of c2139Fcmod, c2137-e1711-Fcmod and MVZ-IgG4. FIG. 30D is in silico graphical representation of c2139 at three different concentrations over a period of 500 hours. FIG. 30E is an in silico graphical representation of c2137-e1711 at three different concentrations over a period of 500 hours. FIG. 30F is in silico graphical representation of isotype control antibody over a period of 500 hours at a concentration of 20 mg/Kg. Non-naïve mice were administered multiple dosing of the mAbs once weekly over 4 total weeks. It was observed that both c2139Fcmod, c2137-e1711-Fcmod maintain exposure with once weekly IV dosing at 5 mg/kg. No severe outcomes were observed with mAbs dosed once weekly for several weeks.

TABLE 18

PK parameters for the exemplar Fc-modified C5aR1 antibodies.

| Ab | Dose | $C_{max}$ (µg/ml) | $t_{last}$ (h) | $AUC_{0-24}$ (µg * h/ml) | $AUC_{last}$ (µg * h/ml) | $AUC_{inf}$ (µg * h/ml) | $t_{1/2}$ (h) | CL (ml/h/kg) | V (ml/kg) |
|---|---|---|---|---|---|---|---|---|---|
| | | | | GeoMean (Geo CV %) | | | | | |
| c2139-Fcmod | 20 mg/kg | 355 (12.2%) | 504 (504-504)* | 4880 (12%) | 34200 (20.8%) | 36700 (26.2%) | 135 (105-163)* | 0.545 (26.2%) | 105 (14.2%) |
| c2137-e1711-Fcmod | 20 mg/kg | 510 (34.6%) | 396 (288-504)* | 6750 (23.2%) | 30100 (28.9%) | 30400 (29.8%) | 31.6 (16.1-90.0)* | 0.657 (29.8%) | 32.6 (65.5%) |
| Isotype CTL | 20 mg/kg | 453 (29.4%) | 504 (288-504)* | 7130 (22.1%) | 55800 (23.4%) | 66200 (20.8%) | 127 (116-192)* | 0.302 (20.8%) | 60.0 (26.7%) |
| c2139-Fcmod | 5 mg/kg | 87.9 (23.7%) | 264 (192-432)* | 1180 (19.6%) | 3680 (34%) | 3780 (34.8%) | 51.6 (24.7-72.0)* | 1.32 (34.8%) | 89.0 (27 1%) |
| c2137-e1711-Fcmod | 5 mg/kg | 84.3 (30%) | 216 (144-288)* | 1140 (10.3%) | 3590 (15.4%) | 4080 (23.1%) | 49.7 (48.5-110)* | 1.22 (23.1%) | 113 (24.8%) |
| c2139-Fcmod | 0.5 mg/kg | 8.45 (33.4%) | 24.0 (24.0-24.0)* | 90.7 (19.6%) | 90.7 (19.6%) | 114 (20.7%) | 10.5 (7.62-11.4)* | 4.40 (20.7%) | 62.8 (25.4%) |
| c2137-e1711-Fcmod | 0.5 mg/kg | 8.05 (21%) | 24.0 (24.0-24.0)* | 89.1 (10.2%) | 89.1 (10.2%) | 119 (9.5%) | 11.7 (9.13-12.9)* | 4.21 (9.5%) | 68.4 (16.9%) |

*Value presented as Median (Min-Max)

Example 27—Inhibition of Neutropenia in Human C5aR1 KI Mice, by Fc-Modified C5aR1 Antibodies at Low Dose This example shows that c2139-Fcmod and c2137-e1711-Fcmod can inhibit neutropenia in Human C5aR1 knock in mice at low doses.

Figure 31:
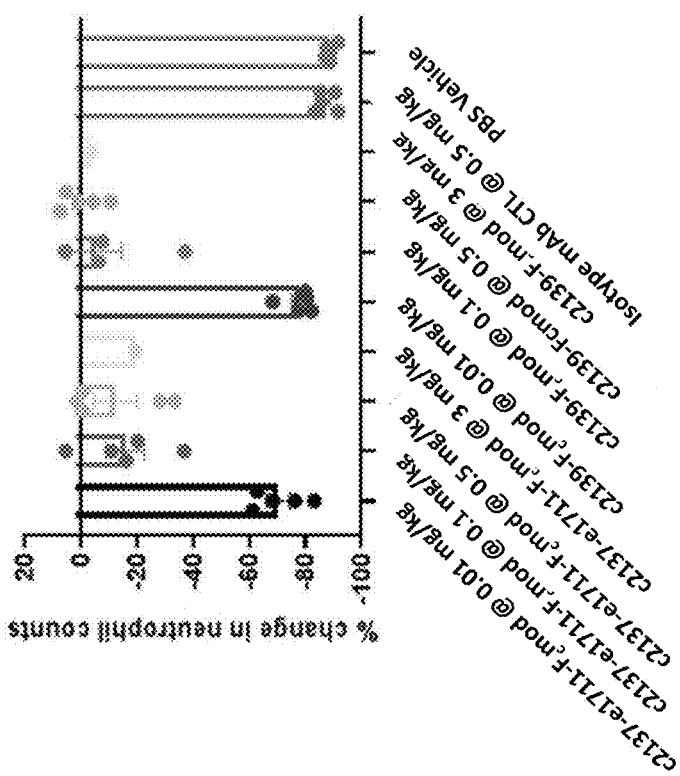
FIG. 31 is a graphical representation of percent change in neutrophil counts with exemplary C5aR1 antibodies c2139-Fcmod and c2137-e1711-Fcmod at different dosages in human C5aR1 mice.

Table 19 summarizes the dosage regimen of the antibodies being tested, and the bleed times to determine neutropenia. Neutrophil change from baseline (−5 min bleed) at 1 min post C5a administration are shown in FIG. 31.

It was observed that c2139-Fcmod and c2137-e1711-Fcmod potently inhibited neutropenia induced by C5a administration compared to vehicle control, even at 0.1 mg/kg doses.

TABLE 19

Dosage Regimen

| Test article | # mice | dose | Neutropenia bleeds | | | | |
|---|---|---|---|---|---|---|---|
| | | | −5 min | 0 hr | 1 min | 5 min | 2 hr |
| c2137-e1711-Fcmod | 5 | 0.01 mg/kg IV | blood | 0.1 mg/kg hC5a IV | blood | blood | blood |
| c2137-e1711-Fcmod | 5 | 0.1 mg/kg IV | | | | | |
| c2137-e1711-Fcmod | 5 | 0.5 mg/kg IV | | | | | |
| c2137-e1711-Fcmod | 1 | 3 mg/kg IV | | | | | |
| c2139-Fcmod | 5 | 0.01 mg/kg IV | | | | | |
| c2139-Fcmod | 5 | 0.1 mg/kg IV | | | | | |
| c2139-Fcmod | 5 | 0.5 mg/kg IV | | | | | |
| c2139-Fcmod | 1 | 3 mg/kg IV | | | | | |
| Isotype mAb CTL | 5 | 0.5 mg/kg IV | | | | | |
| Vehicle (PBS) | 5 | n/a | | | | | |

Example 28—Internalization of Fc Modified C5aR1 Antibodies

This example shows the internalization of Fc modified humanized monospecific and biparatopic C5aR1 antibodies in hC5ar1-U937 cells.

Figure 32B:
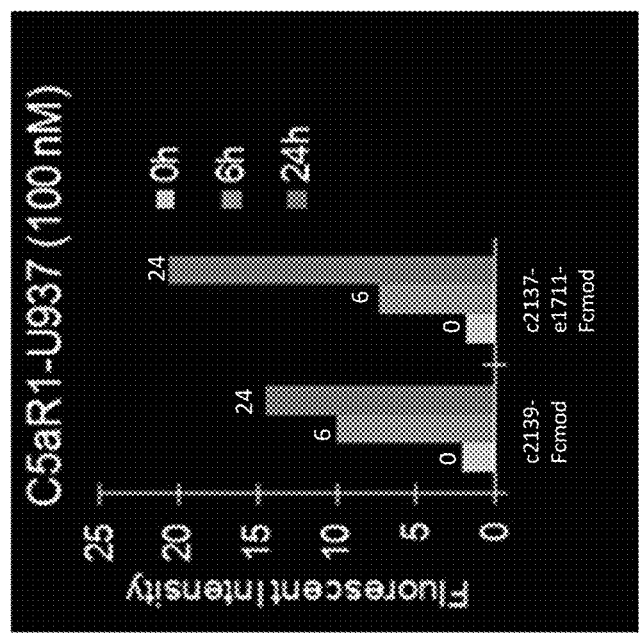
FIG. 32A-32B are graphical representations of internalization of exemplary C5aR1 antibodies, c2139-Fcmod and c2137-e1711-Fcmod.
Figure 32A:
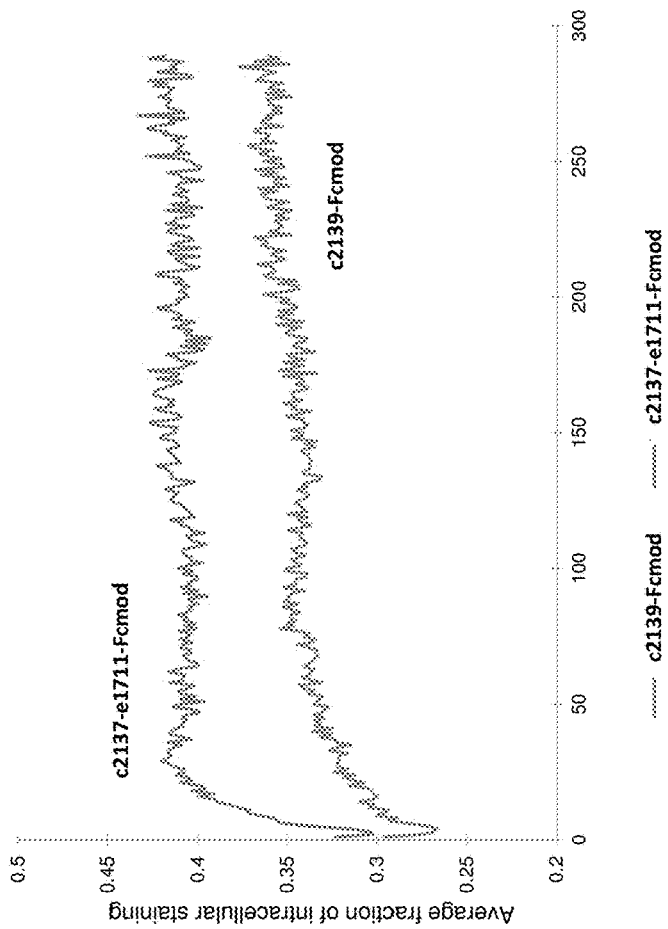

The Fc modified, humanized monospecific anti-C5aR1 antibodies, c2137-e1711-Fcmod and c2139-Fcmod were conjugated to pH sensitive dye (DyLight488), which fluoresces brightly at low pH but is non-fluorescent at neutral pH. The conjugated antibodies were incubated with U937 cells and hC5aR1 knock in U937 cells. FIG. 32A shows the fluorescence intensity after 6 hours and 24 hours of incubation with each conjugated antibody.

It was observed that the exemplary Fc modified C5aR1 antibodies underwent metabolic-based internalization. FIG. 32B shows the internalization of both c2137-e1711-Fcmod and c2139-Fcmod in live cells as observed by Nikon confocal experiment over a period of 300 min.

EQUIVALENTS AND SCOPE

Those skilled in the art will recognize, or be able to ascertain using no more than routine experimentation, many equivalents to the specific embodiments of the disclosure described herein. The scope of the present disclosure is not intended to be limited to the above description, but rather is as set forth in the following claims:

```
SEQUENCE LISTING

Sequence total quantity: 86
SEQ ID NO: 1            moltype = AA  length = 37
FEATURE                 Location/Qualifiers
REGION                  1..37
                        note = source = /note="Description of Artificial Sequence:
                        Syntheticpolypeptide"
source                  1..37
                        mol_type = protein
                        organism = synthetic construct
SEQUENCE: 1
MNSFNYTTPD YGHYDDKDTL DLNTPVDKTS NTLRVPD                                    37

SEQ ID NO: 2            moltype = AA  length = 37
FEATURE                 Location/Qualifiers
REGION                  1..37
                        note = source = /note="Description of Artificial Sequence:
                        Syntheticpolypeptide"
source                  1..37
                        mol_type = protein
                        organism = synthetic construct
SEQUENCE: 2
MDSFNYTTPD YGHYDDKDTL DLNTPVDKTS NTLRVPD                                    37

SEQ ID NO: 3            moltype = AA  length = 26
FEATURE                 Location/Qualifiers
REGION                  1..26
                        note = source = /note="Description of Artificial Sequence:
                        Syntheticpeptide"
source                  1..26
                        mol_type = protein
                        organism = synthetic construct
SEQUENCE: 3
RVVREEYFPP KVLCGVDYSH DKRRER                                                26

SEQ ID NO: 4            moltype = AA  length = 450
FEATURE                 Location/Qualifiers
REGION                  1..450
                        note = source = /note="Description of Artificial Sequence:
```

```
                                Syntheticpolypeptide"
source                          1..450
                                mol_type = protein
                                organism = synthetic construct
SEQUENCE: 4
QVQLVQSGAE VKKPGASVKV SCKASGYTFT NYWMHWVRQA PGQGLEWMGY LNPSSGYTKY    60
AQKFQGRVTM TRDTSTSTVY MELSSLRSED TAVYYCTRSG GDNYGNPYYF DRWGQGTTVT   120
VSSASTKGPS VFPLAPCSRS TSESTAALGC LVKDYFPEPV TVSWNSGALT SGVHTFPAVL   180
QSSGLYSLSS VVTVPSSSLG TKTYTCNVDH KPSNTKVDKR VESKYGPPCP PCPAPEFLGG   240
PSVFLFPPKP KDTLMISRTP EVTCVVVDVS QEDPEVQFNW YVDGVEVHNA KTKPREEQFN   300
STYRVVSVLT VLHQDWLNGK EYKCKVSNKG LPSSIEKTIS KAKGQPREPQ VYTLPPSQEE   360
MTKNQVSLTC LVKGFYPSDI AVEWESNGQP ENNYKTTPPV LDSDGSFFLY SRLTVDKSRW   420
QEGNVFSCSV MHEALHNHYT QKSLSLSLGK                                   450

SEQ ID NO: 5                    moltype = AA  length = 219
FEATURE                         Location/Qualifiers
REGION                          1..219
                                note = source = /note="Description of Artificial Sequence:
                                Syntheticpolypeptide"
source                          1..219
                                mol_type = protein
                                organism = synthetic construct
SEQUENCE: 5
DVQMTQSPSS LSASVGDRVT ITCRASQSIV HSNGNTYLHW YQQKPGKAPK FLIYKVSNRF    60
SGVPSRFSGS GSGTDFTLTI SSLQPEDFAT YYCAQYTLVP LTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 6                    moltype = AA  length = 5
FEATURE                         Location/Qualifiers
REGION                          1..5
                                note = source = /note="Description of Artificial Sequence:
                                Syntheticpeptide"
source                          1..5
                                mol_type = protein
                                organism = synthetic construct
SEQUENCE: 6
NYWMH                                                                 5

SEQ ID NO: 7                    moltype = AA  length = 17
FEATURE                         Location/Qualifiers
REGION                          1..17
                                note = source = /note="Description of Artificial Sequence:
                                Syntheticpeptide"
source                          1..17
                                mol_type = protein
                                organism = synthetic construct
SEQUENCE: 7
YLNPSSGYTK YAQKFQG                                                   17

SEQ ID NO: 8                    moltype = AA  length = 14
FEATURE                         Location/Qualifiers
REGION                          1..14
                                note = source = /note="Description of Artificial Sequence:
                                Syntheticpeptide"
source                          1..14
                                mol_type = protein
                                organism = synthetic construct
SEQUENCE: 8
SGGDNYGNPY YFDR                                                      14

SEQ ID NO: 9                    moltype = AA  length = 16
FEATURE                         Location/Qualifiers
REGION                          1..16
                                note = source = /note="Description of Artificial Sequence:
                                Syntheticpeptide"
source                          1..16
                                mol_type = protein
                                organism = synthetic construct
SEQUENCE: 9
RASQSIVHSN GNTYLH                                                    16

SEQ ID NO: 10                   moltype = AA  length = 7
FEATURE                         Location/Qualifiers
REGION                          1..7
                                note = source = /note="Description of Artificial Sequence:
                                Syntheticpeptide"
source                          1..7
                                mol_type = protein
```

```
                        organism = synthetic construct
SEQUENCE: 10
KVSNRFS                                                                    7

SEQ ID NO: 11           moltype = AA   length = 9
FEATURE                 Location/Qualifiers
REGION                  1..9
                        note = source = /note="Description of Artificial Sequence:
                         Syntheticpeptide"
source                  1..9
                        mol_type = protein
                        organism = synthetic construct
SEQUENCE: 11
AQYTLVPLT                                                                  9

SEQ ID NO: 12           moltype = AA   length = 704
FEATURE                 Location/Qualifiers
REGION                  1..704
                        note = source = /note="Description of Artificial Sequence:
                         Syntheticpolypeptide"
source                  1..704
                        mol_type = protein
                        organism = synthetic construct
SEQUENCE: 12
QVQLVQSGAE VKKPGASVKV SCKASGYTFT NYWMHWVRQA PGQGLEWMGY LNPSSGYTKY           60
AQKFQGRVTM TRDTSTSTVY MELSSLRSED TAVYYCTRSG GDNYGNPYYF DRWGQGTTVT          120
VSSSASTKGPS VFPLAPCSRS TSESTAALGC LVKDYFPEPV TVSWNSGALT SGVHTFPAVL         180
QSSGLYSLSS VVTVPSSSLG TKTYTCNVDH KPSNTKVDKR VESKYGPPCP PCPAPEFLGG          240
PSVFLFPPKP KDTLMISRTP EVTCVVVDVS QEDPEVQFNW YVDGVEVHNA KTKPREEQFN          300
STYRVVSVLT VLHQDWLNGK EYKCKVSNKG LPSSIEKTIS KAKGQPREPQ VYTLPPSQEE          360
MTKNQVSLTC LVKGFYPSDI AVEWESNGQP ENNYKTTPPV LDSDGSFFLY SRLTVDKSRW          420
QEGNVFSCSV MHEALHNHYT QKSLSLSLGG GGGSEIVLTQ SPATLSLSPG ERATLSCRSS          480
QSLVHSNGNT YLNWYQQKPG QAPRLLIYKV SNRLSGIPAR FSGSGSGTDF TLTISSLEPE          540
DFAVYYCSQS THVPYTFGCG TKLEIKGGGG SGGGGSGGGG SGGGGSEVQL VESGGGLIQP          600
GGSLRLSCAA SGFTFNAYAM SWVRQAPGKC LEWVSSISTG GNTYYADSVK GRFTISRDNS          660
KNTLYLQMNS LRAEDTAVYY CTRGYQRFSG FAYWGQGTLV TVSS                          704

SEQ ID NO: 13           moltype = AA   length = 219
FEATURE                 Location/Qualifiers
REGION                  1..219
                        note = source = /note="Description of Artificial Sequence:
                         Syntheticpolypeptide"
source                  1..219
                        mol_type = protein
                        organism = synthetic construct
SEQUENCE: 13
DVQMTQSPSS LSASVGDRVT ITCRASQSIV HSNGNTYLHW YQQKPGKAPK FLIYKVSNRF           60
SGVPSRFSGS GSGTDFTLTI SSLQPEDFAT YYCAQSTLVP LTFGQGTKLE IKRTVAAPSV          120
FIFPPSDEQL KSGTASVVCL LNNFYPREAK VQWKVDNALQ SGNSQESVTE QDSKDSTYSL          180
SSTLTLSKAD YEKHKVYACE VTHQGLSSPV TKSFNRGEC                                219

SEQ ID NO: 14           moltype = AA   length = 123
FEATURE                 Location/Qualifiers
REGION                  1..123
                        note = source = /note="Description of Artificial Sequence:
                         Syntheticpolypeptide"
source                  1..123
                        mol_type = protein
                        organism = synthetic construct
SEQUENCE: 14
QVQLVQSGAE VKKPGASVKV SCKASGYTFT NYWMHWVRQA PGQGLEWMGY LNPSSGYTKY           60
AQKFQGRVTM TRDTSTSTVY MELSSLRSED TAVYYCTRSG GDNYGNPYYF DRWGQGTTVT          120
VSS                                                                      123

SEQ ID NO: 15           moltype = AA   length = 112
FEATURE                 Location/Qualifiers
REGION                  1..112
                        note = source = /note="Description of Artificial Sequence:
                         Syntheticpolypeptide"
source                  1..112
                        mol_type = protein
                        organism = synthetic construct
SEQUENCE: 15
DVQMTQSPSS LSASVGDRVT ITCRASQSIV HSNGNTYLHW YQQKPGKAPK FLIYKVSNRF           60
SGVPSRFSGS GSGTDFTLTI SSLQPEDFAT YYCAQSTLVP LTFGQGTKLE IK                 112

SEQ ID NO: 16           moltype = AA   length = 118
FEATURE                 Location/Qualifiers
REGION                  1..118
```

```
                        note = source = /note="Description of Artificial Sequence:
                          Syntheticpolypeptide"
source                  1..118
                        mol_type = protein
                        organism = synthetic construct
SEQUENCE: 16
EVQLVESGGG LIQPGGSLRL SCAASGFTFN AYAMSWVRQA PGKCLEWVSS ISTGGNTYYA      60
DSVKGRFTIS RDNSKNTLYL QMNSLRAEDT AVYYCTRGYQ RFSGFAYWGQ GTLVTVSS      118

SEQ ID NO: 17           moltype = AA   length = 112
FEATURE                 Location/Qualifiers
REGION                  1..112
                        note = source = /note="Description of Artificial Sequence:
                          Syntheticpolypeptide"
source                  1..112
                        mol_type = protein
                        organism = synthetic construct
SEQUENCE: 17
EIVLTQSPAT LSLSPGERAT LSCRSSQSLV HSNGNTYLNW YQQKPGQAPR LLIYKVSNRL      60
SGIPARFSGS GSGTDFTLTI SSLEPEDFAV YYCSQSTHVP YTFGCGTKLE IK             112

SEQ ID NO: 18           moltype = AA   length = 5
FEATURE                 Location/Qualifiers
REGION                  1..5
                        note = source = /note="Description of Artificial Sequence:
                          Syntheticpeptide"
source                  1..5
                        mol_type = protein
                        organism = synthetic construct
SEQUENCE: 18
AYAMS                                                                   5

SEQ ID NO: 19           moltype = AA   length = 16
FEATURE                 Location/Qualifiers
REGION                  1..16
                        note = source = /note="Description of Artificial Sequence:
                          Syntheticpeptide"
source                  1..16
                        mol_type = protein
                        organism = synthetic construct
SEQUENCE: 19
SISTGGNTYY ADSVKG                                                      16

SEQ ID NO: 20           moltype = AA   length = 10
FEATURE                 Location/Qualifiers
REGION                  1..10
                        note = source = /note="Description of Artificial Sequence:
                          Syntheticpeptide"
source                  1..10
                        mol_type = protein
                        organism = synthetic construct
SEQUENCE: 20
GYQRFSGFAY                                                             10

SEQ ID NO: 21           moltype = AA   length = 9
FEATURE                 Location/Qualifiers
REGION                  1..9
                        note = source = /note="Description of Artificial Sequence:
                          Syntheticpeptide"
source                  1..9
                        mol_type = protein
                        organism = synthetic construct
SEQUENCE: 21
AQSTLVPLT                                                               9

SEQ ID NO: 22           moltype = AA   length = 16
FEATURE                 Location/Qualifiers
REGION                  1..16
                        note = source = /note="Description of Artificial Sequence:
                          Syntheticpeptide"
source                  1..16
                        mol_type = protein
                        organism = synthetic construct
SEQUENCE: 22
RSSQSLVHSN GNTYLN                                                      16

SEQ ID NO: 23           moltype = AA   length = 7
FEATURE                 Location/Qualifiers
REGION                  1..7
```

```
                        note = source = /note="Description of Artificial Sequence:
                             Syntheticpeptide"
source                  1..7
                        mol_type = protein
                        organism = synthetic construct
SEQUENCE: 23
KVSNRLS                                                                    7

SEQ ID NO: 24           moltype = AA  length = 9
FEATURE                 Location/Qualifiers
REGION                  1..9
                        note = source = /note="Description of Artificial Sequence:
                             Syntheticpeptide"
source                  1..9
                        mol_type = protein
                        organism = synthetic construct
SEQUENCE: 24
SQSTHVPYT                                                                  9

SEQ ID NO: 25           moltype = AA  length = 112
FEATURE                 Location/Qualifiers
REGION                  1..112
                        note = source = /note="Description of Artificial Sequence:
                             Syntheticpolypeptide"
source                  1..112
                        mol_type = protein
                        organism = synthetic construct
SEQUENCE: 25
DVQMTQSPSS LSASVGDRVT ITCRASQSIV HSNGNTYLHW YQQKPGKAPK FLIYKVSNRF     60
SGVPSRFSGS GSGTDFTLTI SSLQPEDFAT YYCAQYTLVP LTFGQGTKLE IK             112

SEQ ID NO: 26           moltype = AA  length = 4
FEATURE                 Location/Qualifiers
REGION                  1..4
                        note = source = /note="Description of Artificial Sequence:
                             Syntheticpeptide"
source                  1..4
                        mol_type = protein
                        organism = synthetic construct
SEQUENCE: 26
GGGG                                                                       4

SEQ ID NO: 27           moltype = AA  length = 5
FEATURE                 Location/Qualifiers
REGION                  1..5
                        note = source = /note="Description of Artificial Sequence:
                             Syntheticpeptide"
source                  1..5
                        mol_type = protein
                        organism = synthetic construct
SEQUENCE: 27
GGGGG                                                                      5

SEQ ID NO: 28           moltype = AA  length = 6
FEATURE                 Location/Qualifiers
REGION                  1..6
                        note = source = /note="Description of Artificial Sequence:
                             Syntheticpeptide"
source                  1..6
                        mol_type = protein
                        organism = synthetic construct
SEQUENCE: 28
GGGGGG                                                                     6

SEQ ID NO: 29           moltype = AA  length = 7
FEATURE                 Location/Qualifiers
REGION                  1..7
                        note = source = /note="Description of Artificial Sequence:
                             Syntheticpeptide"
source                  1..7
                        mol_type = protein
                        organism = synthetic construct
SEQUENCE: 29
GGGGGGG                                                                    7

SEQ ID NO: 30           moltype = AA  length = 8
FEATURE                 Location/Qualifiers
REGION                  1..8
                        note = source = /note="Description of Artificial Sequence:
```

```
                            Syntheticpeptide"
source                      1..8
                            mol_type = protein
                            organism = synthetic construct
SEQUENCE: 30
GGGGGGGG                                                                  8

SEQ ID NO: 31               moltype = AA  length = 5
FEATURE                     Location/Qualifiers
REGION                      1..5
                            note = source = /note="Description of Artificial Sequence:
                            Syntheticpeptide"
source                      1..5
                            mol_type = protein
                            organism = synthetic construct
SEQUENCE: 31
GGGGS                                                                     5

SEQ ID NO: 32               moltype = AA  length = 10
FEATURE                     Location/Qualifiers
REGION                      1..10
                            note = source = /note="Description of Artificial Sequence:
                            Syntheticpeptide"
source                      1..10
                            mol_type = protein
                            organism = synthetic construct
SEQUENCE: 32
GGGGSGGGGS                                                               10

SEQ ID NO: 33               moltype = AA  length = 15
FEATURE                     Location/Qualifiers
REGION                      1..15
                            note = source = /note="Description of Artificial Sequence:
                            Syntheticpeptide"
source                      1..15
                            mol_type = protein
                            organism = synthetic construct
SEQUENCE: 33
GGGGSGGGGS GGGGS                                                         15

SEQ ID NO: 34               moltype = AA  length = 20
FEATURE                     Location/Qualifiers
REGION                      1..20
                            note = source = /note="Description of Artificial Sequence:
                            Syntheticpeptide"
source                      1..20
                            mol_type = protein
                            organism = synthetic construct
SEQUENCE: 34
GGGGSGGGGS GGGGSGGGGS                                                    20

SEQ ID NO: 35               moltype = AA  length = 10
FEATURE                     Location/Qualifiers
REGION                      1..10
                            note = source = /note="Description of Artificial Sequence:
                            Syntheticpeptide"
source                      1..10
                            mol_type = protein
                            organism = synthetic construct
SEQUENCE: 35
GGSGSSGSGG                                                               10

SEQ ID NO: 36               moltype = AA  length = 5
FEATURE                     Location/Qualifiers
REGION                      1..5
                            note = source = /note="Description of Artificial Sequence:
                            Syntheticpeptide"
source                      1..5
                            mol_type = protein
                            organism = synthetic construct
SEQUENCE: 36
QRIEG                                                                     5

SEQ ID NO: 37               moltype = AA  length = 7
FEATURE                     Location/Qualifiers
REGION                      1..7
                            note = source = /note="Description of Artificial Sequence:
                            Syntheticpeptide"
source                      1..7
```

```
                        mol_type = protein
                        organism = synthetic construct
SEQUENCE: 37
GQPKAAP                                                                 7

SEQ ID NO: 38           moltype = AA   length = 350
FEATURE                 Location/Qualifiers
REGION                  1..350
                        note = source = /note="Description of Artificial Sequence:
                         Syntheticpolypeptide"
source                  1..350
                        mol_type = protein
                        organism = synthetic construct
SEQUENCE: 38
MNSFNYTTPD YGHYDDKDTL DLNTPVDKTS NTLRVPDILA LVIFAVVFLV GVLGNALVVW        60
VTAFEAKRTI NAIWFLNLAV ADFLSCLALP ILFTSIVQHH HWPFGGAACS ILPSLILLNM       120
YASILLLATI SADRFLLVFK PIWCQNFRGA GLAWIACAVA WGLALLLTIP SFLYRVVREE       180
YFPPKVLCGV DYSHDKRRER AVAIVRLVLG FLWPLLTLTI CYTFILLRTW SRRATRSTKT       240
LKVVVAVVAS FFIFWLPYQV TGIMMSFLEP SSPTFLLLNK LDSLCVSFAY INCCINPIIY       300
VVAGQGFQGR LRKSLPSLLR NVLTEESVVR ESKSFTRSTV DTMAQKTQAV                  350

SEQ ID NO: 39           moltype = AA   length = 118
FEATURE                 Location/Qualifiers
REGION                  1..118
                        note = source = /note="Description of Artificial Sequence:
                         Syntheticpolypeptide"
source                  1..118
                        mol_type = protein
                        organism = synthetic construct
SEQUENCE: 39
QVQLVQSGAE VKKPGASVKV SCAASGFTFN AYAMSWVRQA PGQGLEWMGS ISTGGNTYYA        60
QKFQGRVTMT RDTSTSTVYM ELSSLRSEDT AVYYCTRGYQ RFSGFAYWGQ GTLVTVSS        118

SEQ ID NO: 40           moltype = AA   length = 118
FEATURE                 Location/Qualifiers
REGION                  1..118
                        note = source = /note="Description of Artificial Sequence:
                         Syntheticpolypeptide"
source                  1..118
                        mol_type = protein
                        organism = synthetic construct
SEQUENCE: 40
EVQLVESGGG LVQPGGSLRL SCAASGFTFN AYAMSWVRQA TGKGLEWVSS ISTGGNTYYP        60
GSVKGRFTIS RENAKNSLYL QMNSLRAGDT AVYYCTRGYQ RFSGFAYWGQ GTLVTVSS        118

SEQ ID NO: 41           moltype = AA   length = 118
FEATURE                 Location/Qualifiers
REGION                  1..118
                        note = source = /note="Description of Artificial Sequence:
                         Syntheticpolypeptide"
source                  1..118
                        mol_type = protein
                        organism = synthetic construct
SEQUENCE: 41
EVQLVESGGG LVQPGGSLRL SCAASGFTFN AYAMSWVRQA TGKGLEWVSS ISTGGNTYYP        60
GSVKGRFTIS RENAKNSLYL QMNSLRAGDT AVYYCARGYQ RFSGFAYWGQ GTLVTVSS        118

SEQ ID NO: 42           moltype = AA   length = 118
FEATURE                 Location/Qualifiers
REGION                  1..118
                        note = source = /note="Description of Artificial Sequence:
                         Syntheticpolypeptide"
source                  1..118
                        mol_type = protein
                        organism = synthetic construct
SEQUENCE: 42
EVQLLESGGG LVQPGGSLRL SCAASGFTFN AYAMSWVRQA PGKGLEWVSS ISTGGNTYYA        60
DSVKGRFTIS RDNSKNTLYL QMNSLRAEDT AVYYCTRGYQ RFSGFAYWGQ GTLVTVSS        118

SEQ ID NO: 43           moltype = AA   length = 118
FEATURE                 Location/Qualifiers
REGION                  1..118
                        note = source = /note="Description of Artificial Sequence:
                         Syntheticpolypeptide"
source                  1..118
                        mol_type = protein
                        organism = synthetic construct
SEQUENCE: 43
EVQLVESGGG LIQPGGSLRL SCAASGFTFN AYAMSWVRQA PGKGLEWVSS ISTGGNTYYA        60
```

```
DSVKGRFTIS RDNSKNTLYL QMNSLRAEDT AVYYCTRGYQ RFSGFAYWGQ GTLVTVSS        118

SEQ ID NO: 44            moltype = AA   length = 112
FEATURE                  Location/Qualifiers
REGION                   1..112
                         note = source = /note="Description of Artificial Sequence:
                         Syntheticpolypeptide"
source                   1..112
                         mol_type = protein
                         organism = synthetic construct
SEQUENCE: 44
DIQMTQSPSS LSASVGDRVT ITCRASQSIV HSNGNTYLNW YQQKPGKAPK LLIYKVSNRL       60
SGVPSRFSGS GSGTDFTLTI SSLQPEDFAT YYCSQSTHVP YTFGQGTKLE IK              112

SEQ ID NO: 45            moltype = AA   length = 112
FEATURE                  Location/Qualifiers
REGION                   1..112
                         note = source = /note="Description of Artificial Sequence:
                         Syntheticpolypeptide"
source                   1..112
                         mol_type = protein
                         organism = synthetic construct
SEQUENCE: 45
DIVMTQTPLS SPVTLGQPAS ISCRSSQSLV HSNGNTYLNW LQQRPGQPPR LLIYKVSNRL       60
SGVPDRFSGS GAGTDFTLKI SRVEAEDVGV YYCSQSTHVP YTFGQGTKLE IK              112

SEQ ID NO: 46            moltype = AA   length = 112
FEATURE                  Location/Qualifiers
REGION                   1..112
                         note = source = /note="Description of Artificial Sequence:
                         Syntheticpolypeptide"
source                   1..112
                         mol_type = protein
                         organism = synthetic construct
SEQUENCE: 46
DVVMTQTPLS SPVTLGQPAS ISCRSSQSLV HSNGNTYLNW YQQRPGQPPR LLIYKVSNRL       60
SGVPDRFSGS GAGTDFTLKI SRVEAEDVGV YYCSQSTHVP YTFGQGTKLE IK              112

SEQ ID NO: 47            moltype = AA   length = 112
FEATURE                  Location/Qualifiers
REGION                   1..112
                         note = source = /note="Description of Artificial Sequence:
                         Syntheticpolypeptide"
source                   1..112
                         mol_type = protein
                         organism = synthetic construct
SEQUENCE: 47
DVVMTQSPLS LPVTPGEPAS ISCRSSQSLV HSNGNTYLNW YLQKPGQSPQ LLIYKVSNRL       60
SGVPDRFSGS GSGTDFTLKI SRVEAEDVGV YYCSQSTHVP YTFGQGTKLE IK              112

SEQ ID NO: 48            moltype = AA   length = 112
FEATURE                  Location/Qualifiers
REGION                   1..112
                         note = source = /note="Description of Artificial Sequence:
                         Syntheticpolypeptide"
source                   1..112
                         mol_type = protein
                         organism = synthetic construct
SEQUENCE: 48
EIVLTQSPAT LSLSPGERAT LSCRSSQSLV HSNGNTYLNW YQQKPGQAPR LLIYKVSNRL       60
SGIPARFSGS GSGTDFTLTI SSLEPEDFAV YYCSQSTHVP YTFGQGTKLE IK              112

SEQ ID NO: 49            moltype = AA   length = 112
FEATURE                  Location/Qualifiers
REGION                   1..112
                         note = source = /note="Description of Artificial Sequence:
                         Syntheticpolypeptide"
source                   1..112
                         mol_type = protein
                         organism = synthetic construct
SEQUENCE: 49
EIVLTQSPGT LSLSPGERAT LSCRASQSVV HSNGNTYLNW YQQKPGQAPR LLIYKVSNRL       60
SGIPDRFSGS GSGTDFTLTI SRLEPEDFAV YYCSQSTHVP YTFGQGTKLE IK              112

SEQ ID NO: 50            moltype = AA   length = 121
FEATURE                  Location/Qualifiers
REGION                   1..121
                         note = source = /note="Description of Artificial Sequence:
                         Syntheticpolypeptide"
```

```
                        source          1..121
                                        mol_type = protein
                                        organism = synthetic construct
SEQUENCE: 50
QVQLVQSGAE VKKPGASVKV SCKASGYSFS SSWINWVRQA PGQGLEWMGR ISAYDGDTRY    60
AQKLQGRVTM TADKSTSTAY MELRSLRSDD TAVYYCVRFL ITSTRYVMDY WGQGTTVTVS   120
S                                                                  121

SEQ ID NO: 51           moltype = AA   length = 121
FEATURE                 Location/Qualifiers
REGION                  1..121
                        note = source = /note="Description of Artificial Sequence:
                         Syntheticpolypeptide"
source                  1..121
                        mol_type = protein
                        organism = synthetic construct
SEQUENCE: 51
QVQLVQSGAE VKKPGASVKV SCKASGYSFS SSWMNWVRQA PGQRLEWMGR ISAGDGDTRY    60
SQKFQGRVTI TADKSASTAY MELSSLRSED TAVYYCVRFL ITSTRYVMDY WGQGTTVTVS   120
S                                                                  121

SEQ ID NO: 52           moltype = AA   length = 121
FEATURE                 Location/Qualifiers
REGION                  1..121
                        note = source = /note="Description of Artificial Sequence:
                         Syntheticpolypeptide"
source                  1..121
                        mol_type = protein
                        organism = synthetic construct
SEQUENCE: 52
QVQLVQSGAE VKKPGSSVKV SCKASGGSFS SSWINWVRQA PGQGLEWMGR ISPGDGDTRY    60
AQKFQGRVTI TADKSTSTAY MELSSLRSED TAVYYCVRFL ITSTRYVMDY WGQGTTVTVS   120
S                                                                  121

SEQ ID NO: 53           moltype = AA   length = 121
FEATURE                 Location/Qualifiers
REGION                  1..121
                        note = source = /note="Description of Artificial Sequence:
                         Syntheticpolypeptide"
source                  1..121
                        mol_type = protein
                        organism = synthetic construct
SEQUENCE: 53
QVQLVQSGAE VKKPGASVKV SCKASGYSFS SSWINWVRQA TGQGLEWMGR MSPGDGDTRY    60
AQKFQGRVTM TANKSISTAY MELSSLRSED TAVYYCVRFL ITSTRYVMDY WGQGTTVTVS   120
S                                                                  121

SEQ ID NO: 54           moltype = AA   length = 121
FEATURE                 Location/Qualifiers
REGION                  1..121
                        note = source = /note="Description of Artificial Sequence:
                         Syntheticpolypeptide"
source                  1..121
                        mol_type = protein
                        organism = synthetic construct
SEQUENCE: 54
EVQLVQSGAE VKKPGESLRI SCKASGYSFS SSWMNWVRQM PGKGLEWMGR ISPGDGDTRY    60
SPSFQGHVTI SADKSISTAY LQWSSLKASD TAMYFCVRFL ITSTRYVMDY WGQGTTVTVS   120
S                                                                  121

SEQ ID NO: 55           moltype = AA   length = 121
FEATURE                 Location/Qualifiers
REGION                  1..121
                        note = source = /note="Description of Artificial Sequence:
                         Syntheticpolypeptide"
source                  1..121
                        mol_type = protein
                        organism = synthetic construct
SEQUENCE: 55
EVQLVQSGAE VKKPGESLKI SCKGSGYSFS SSWINWVRQM PGKGLEWMGR ISPGDGDTRY    60
SPSFQGQVTI SADKSISTAY LQWSSLKASD TAMYYCVRFL ITSTRYVMDY WGQGTTVTVS   120
S                                                                  121

SEQ ID NO: 56           moltype = AA   length = 123
FEATURE                 Location/Qualifiers
REGION                  1..123
                        note = source = /note="Description of Artificial Sequence:
                         Syntheticpolypeptide"
source                  1..123
```

```
                        mol_type = protein
                        organism = synthetic construct
SEQUENCE: 56
QVQLVQSGAE VKKPGASVKV SCKASGYTFT NYWMHWVRQA PGQGLEWMGY LNPSSGYTKY    60
AQKLQGRVTM TADKSTSTAY MELRSLRSDD TAVYYCTRSG GDNYGNPYYF DRWGQGTTVT   120
VSS                                                                 123

SEQ ID NO: 57           moltype = AA  length = 123
FEATURE                 Location/Qualifiers
REGION                  1..123
                        note = source = /note="Description of Artificial Sequence:
                         Syntheticpolypeptide"
source                  1..123
                        mol_type = protein
                        organism = synthetic construct
SEQUENCE: 57
QVQLVQSGAE VKKPGASVKV SCKASGYTFT NYWMHWVRQA PGQRLEWMGY LNPSSGYTKY    60
SQKFQGRVTI TRDTSASTAY MELSSLRSED TAVYYCTRSG GDNYGNPYYF DRWGQGTTVT   120
VSS                                                                 123

SEQ ID NO: 58           moltype = AA  length = 123
FEATURE                 Location/Qualifiers
REGION                  1..123
                        note = source = /note="Description of Artificial Sequence:
                         Syntheticpolypeptide"
source                  1..123
                        mol_type = protein
                        organism = synthetic construct
SEQUENCE: 58
QVQLVQSGAE VKKPGASVKV SCKASGYTFT NYWIHWVRQA TGQGLEWMGY MNPSSGYTKY    60
AQKFQGRVTM TANKSISTAY MELSSLRSED TAVYYCTRSG GDNYGNPYYF DRWGQGTTVT   120
VSS                                                                 123

SEQ ID NO: 59           moltype = AA  length = 123
FEATURE                 Location/Qualifiers
REGION                  1..123
                        note = source = /note="Description of Artificial Sequence:
                         Syntheticpolypeptide"
source                  1..123
                        mol_type = protein
                        organism = synthetic construct
SEQUENCE: 59
EVQLVQSGAE VKKPGESLKI SCKGSGYTFT NYWIHWVRQM PGKGLEWMGY INPSSGYTKY    60
SPSFQGQVTI SADKSISTAY LQWSSLKASD TAMYYCTRSG GDNYGNPYYF DRWGQGTTVT   120
VSS                                                                 123

SEQ ID NO: 60           moltype = AA  length = 112
FEATURE                 Location/Qualifiers
REGION                  1..112
                        note = source = /note="Description of Artificial Sequence:
                         Syntheticpolypeptide"
source                  1..112
                        mol_type = protein
                        organism = synthetic construct
SEQUENCE: 60
DIQMTQSPSS LSASVGDRVT ITCRSSQSLV HSNGNTYLHW YQQKPGKAPK LLIYKVSNRF    60
SGVPSRFSGS GSGTDFTLTI SSLQPEDFAT YYCSQSTLVP PTFGQGTKLE IK           112

SEQ ID NO: 61           moltype = AA  length = 112
FEATURE                 Location/Qualifiers
REGION                  1..112
                        note = source = /note="Description of Artificial Sequence:
                         Syntheticpolypeptide"
source                  1..112
                        mol_type = protein
                        organism = synthetic construct
SEQUENCE: 61
DVVMTQTPLS SPVTLGQPAS ISCRSSQSLV HSNGNTYLHW YQQRPGQPPR LLIYKVSNRF    60
SGVPDRFSGS GAGTDFTLKI SRVEAEDVGV YYCSQSTLVP PTFGQGTKLE IK           112

SEQ ID NO: 62           moltype = AA  length = 112
FEATURE                 Location/Qualifiers
REGION                  1..112
                        note = source = /note="Description of Artificial Sequence:
                         Syntheticpolypeptide"
source                  1..112
                        mol_type = protein
                        organism = synthetic construct
SEQUENCE: 62
```

```
EVVMTQSPAT LSVSPGERAT LSCRSSQSLV HSNGNTYLHW YQQKPGQAPR LLIYKVSNRF    60
SGIPARFSGS GSGTEFTLTI SSLQSEDFAV YYCSQSTLVP PTFGQGTKLE IK           112

SEQ ID NO: 63              moltype = AA  length = 112
FEATURE                    Location/Qualifiers
REGION                     1..112
                           note = source = /note="Description of Artificial Sequence:
                             Syntheticpolypeptide"
source                     1..112
                           mol_type = protein
                           organism = synthetic construct
SEQUENCE: 63
DVQMTQSPSS LSASVGDRVT ITCRASQSIV HSNGNTYLHW YQQKPGKAPK FLIYKVSNRF    60
SGVPSRFSGS GSGTDFTLTI SSLQPEDFAT YYCSQSTLVP LTFGQGTKLE IK           112

SEQ ID NO: 64              moltype = AA  length = 112
FEATURE                    Location/Qualifiers
REGION                     1..112
                           note = source = /note="Description of Artificial Sequence:
                             Syntheticpolypeptide"
source                     1..112
                           mol_type = protein
                           organism = synthetic construct
SEQUENCE: 64
DVVMTQTPLS SPVTLGQPAS ISCRSSQSLV HSNGNTYLHW YQQRPGQPPR FLIYKVSNRF    60
SGVPDRFSGS GAGTDFTLKI SRVEAEDVGV YYCSQSTLVP LTFGQGTKLE IK           112

SEQ ID NO: 65              moltype = AA  length = 112
FEATURE                    Location/Qualifiers
REGION                     1..112
                           note = source = /note="Description of Artificial Sequence:
                             Syntheticpolypeptide"
source                     1..112
                           mol_type = protein
                           organism = synthetic construct
SEQUENCE: 65
DVVMTQSPLS LPVTPGEPAS ISCRSSQSLV HSNGNTYLHW YLQKPGQSPQ FLIYKVSNRF    60
SGVPDRFSGS GSGTDFTLKI SRVEAEDVGV YYCSQSTLVP LTFGQGTKLE IK           112

SEQ ID NO: 66              moltype = AA  length = 112
FEATURE                    Location/Qualifiers
REGION                     1..112
                           note = source = /note="Description of Artificial Sequence:
                             Syntheticpolypeptide"
source                     1..112
                           mol_type = protein
                           organism = synthetic construct
SEQUENCE: 66
DVVMTQSPLS LPVTLGQPAS ISCRSSQSLV HSNGNTYLHW FQQRPGQSPR RLIYKVSNRF    60
SGVPDRFSGS GSGTDFTLKI SRVEAEDVGV YYCSQSTLVP LTFGQGTKLE IK           112

SEQ ID NO: 67              moltype = AA  length = 112
FEATURE                    Location/Qualifiers
REGION                     1..112
                           note = source = /note="Description of Artificial Sequence:
                             Syntheticpolypeptide"
source                     1..112
                           mol_type = protein
                           organism = synthetic construct
SEQUENCE: 67
DVVMTQSPLS LPVTLGQPAS ISCRSSQSLV HSNGNTYLHW YQQRPGQSPR FLIYKVSNRF    60
SGVPDRFSGS GSGTDFTLKI SRVEAEDVGV YYCSQSTLVP LTFGQGTKLE IK           112

SEQ ID NO: 68              moltype = AA  length = 112
FEATURE                    Location/Qualifiers
REGION                     1..112
                           note = source = /note="Description of Artificial Sequence:
                             Syntheticpolypeptide"
source                     1..112
                           mol_type = protein
                           organism = synthetic construct
SEQUENCE: 68
DVQMTQSPSS LSASVGDRVT ITCRASQSIV HSNGNTYLHW YQQKPGKAPK FLIYKVSNRF    60
SGVPSRFSGS GSGTDFTLTI SSLQPEDFAT YYCSQYTLVP LTFGQGTKLE IK           112

SEQ ID NO: 69              moltype = AA  length = 450
FEATURE                    Location/Qualifiers
REGION                     1..450
                           note = source = /note="Description of Artificial Sequence:
```

```
                          Syntheticpolypeptide"
source                    1..450
                          mol_type = protein
                          organism = synthetic construct
SEQUENCE: 69
QVQLVQSGAE VKKPGASVKV SCKASGYTFT NYWMHWVRQA PGQGLEWMGY LNPSSGYTKY    60
AQKFQGRVTM TRDTSTSTVY MELSSLRSED TAVYYCTRSG GDNYGNPYYF DRWGQGTTVT   120
VSSASTKGPS VFPLAPCSRS TSESTAALGC LVKDYFPEPV TVSWNSGALT SGVHTFPAVL   180
QSSGLYSLSS VVTVPSSSLG TKTYTCNVDH KPSNTKVDKR VESKYGPPCP PCPAPEVEGG   240
PSVFLFPPKP KDTLMISRTP EVTCVVVGVS QEDPEVQFNW YVDGVEVHNA KTKPREEQFN   300
STYRVVSVLT VLHQDWLNGK EYKCKVSNKG LPSSIEKTIS KAKGQPREPQ VYTLPPSQEE   360
MTKNQVSLTC LVKGFYPSDI AVEWESNGQP ENNYKTTPPV LDSDGSFFLY SRLTVDKSRW   420
QEGNVFSCSV MHEALHNHYT QKSLSLSLGK                                   450

SEQ ID NO: 70             moltype = AA  length = 219
FEATURE                   Location/Qualifiers
REGION                    1..219
                          note = source = /note="Description of Artificial Sequence:
                          Syntheticpolypeptide"
source                    1..219
                          mol_type = protein
                          organism = synthetic construct
SEQUENCE: 70
DVQMTQSPSS LSASVGDRVT ITCRASQSIV HSNGNTYLHW YQQKPGKAPK FLIYKVSNRF    60
SGVPSRFSGS GSGTDFTLTI SSLQPEDFAT YYCAQYTLVP LTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 71             moltype = AA  length = 704
FEATURE                   Location/Qualifiers
REGION                    1..704
                          note = source = /note="Description of Artificial Sequence:
                          Syntheticpolypeptide"
source                    1..704
                          mol_type = protein
                          organism = synthetic construct
SEQUENCE: 71
QVQLVQSGAE VKKPGASVKV SCKASGYTFT NYWMHWVRQA PGQGLEWMGY LNPSSGYTKY    60
AQKFQGRVTM TRDTSTSTVY MELSSLRSED TAVYYCTRSG GDNYGNPYYF DRWGQGTTVT   120
VSSASTKGPS VFPLAPCSRS TSESTAALGC LVKDYFPEPV TVSWNSGALT SGVHTFPAVL   180
QSSGLYSLSS VVTVPSSSLG TKTYTCNVDH KPSNTKVDKR VESKYGPPCP PCPAPEVEGG   240
PSVFLFPPKP KDTLMISRTP EVTCVVVGVS QEDPEVQFNW YVDGVEVHNA KTKPREEQFN   300
STYRVVSVLT VLHQDWLNGK EYKCKVSNKG LPSSIEKTIS KAKGQPREPQ VYTLPPSQEE   360
MTKNQVSLTC LVKGFYPSDI AVEWESNGQP ENNYKTTPPV LDSDGSFFLY SRLTVDKSRW   420
QEGNVFSCSV MHEALHNHYT QKSLSLSLGG GGGSEIVLTQ SPATLSLSPG ERATLSCRSS   480
QSLVHSNGNT YLNWYQQKPG QAPRLLIYKV SNRLSGIPAR FSGSGSGTDF TLTISSLEPE   540
DFAVYYCSQS THVPYTFGCG TKLEIKGGGG SGGGGSGGGG SEVQL VESGGGLIQP        600
GGSLRLSCAA SGFTFNAYAM SWVRQAPGKC LEWVSSISTG GNTYYADSVK GRFTISRDNS   660
KNTLYLQMNS LRAEDTAVYY CTRGYQRFSG FAYWGQGTLV TVSS                    704

SEQ ID NO: 72             moltype = AA  length = 219
FEATURE                   Location/Qualifiers
REGION                    1..219
                          note = source = /note="Description of Artificial Sequence:
                          Syntheticpolypeptide"
source                    1..219
                          mol_type = protein
                          organism = synthetic construct
SEQUENCE: 72
DVQMTQSPSS LSASVGDRVT ITCRASQSIV HSNGNTYLHW YQQKPGKAPK FLIYKVSNRF    60
SGVPSRFSGS GSGTDFTLTI SSLQPEDFAT YYCAQSTLVP LTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 73             moltype = AA  length = 112
FEATURE                   Location/Qualifiers
REGION                    1..112
                          note = source = /note="Description of Artificial Sequence:
                          Syntheticpolypeptide"
source                    1..112
                          mol_type = protein
                          organism = synthetic construct
SEQUENCE: 73
DVQMTQSPSS LSASVGDRVT ITCRASQSIV HSNGNTYLHW YQQKPGKAPK FLIYKVSNRF    60
SGVPSRFSGS GSGTDFTLTI SSLQPEDFAT YYCAQYTLVP LTFGQGTKLE IK           112

SEQ ID NO: 74             moltype = AA  length = 123
FEATURE                   Location/Qualifiers
REGION                    1..123
```

```
                            note = source = /note="Description of Artificial Sequence:
                                Syntheticpolypeptide"
source                      1..123
                            mol_type = protein
                            organism = synthetic construct
SEQUENCE: 74
QVQLVQSGAE VKKPGASVKV SCKASGYTFT NYWMHWVRQA PGQGLEWMGY LNPSSGYTKY    60
AQKFQGRVTM TRDTSTSTVY MELSSLRSED TAVYYCTRSG GDNYGNPYYF DRWGQGTTVT   120
VSS                                                                 123

SEQ ID NO: 75               moltype = AA  length = 219
FEATURE                     Location/Qualifiers
REGION                      1..219
                            note = source = /note="Description of Artificial Sequence:
                                Syntheticpolypeptide"
source                      1..219
                            mol_type = protein
                            organism = synthetic construct
SEQUENCE: 75
DVQMTQSPSS LSASVGDRVT ITCRASQSIV HSNGNTYLHW YQQKPGKAPK FLIYKVSNRF    60
SGVPSRFSGS GSGTDFTLTI SSLQPEDFAT YYCAQSTLVP LTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 76               moltype = AA  length = 219
FEATURE                     Location/Qualifiers
REGION                      1..219
                            note = source = /note="Description of Artificial Sequence:
                                Syntheticpolypeptide"
source                      1..219
                            mol_type = protein
                            organism = synthetic construct
SEQUENCE: 76
DVQMTQSPSS LSASVGDRVT ITCRASQSIV HSNGNTYLHW YQQKPGKAPK FLIYKVSNRF    60
SGVPSRFSGS GSGTDFTLTI SSLQPEDFAT YYCAQYTLVP LTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 77               moltype = AA  length = 445
FEATURE                     Location/Qualifiers
REGION                      1..445
                            note = source = /note="Description of Artificial Sequence:
                                Syntheticpolypeptide"
source                      1..445
                            mol_type = protein
                            organism = synthetic construct
SEQUENCE: 77
EVQLVESGGG LIQPGGSLRL SCAASGFTFN AYAMSWVRQA PGKGLEWVSS ISTGGNTYYA    60
DSVKGRFTIS RDNSKNTLYL QMNSLRAEDT AVYYCTRGYQ RFSGFAYWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFLGGPSVFL   240
FPPKPKDTLM ISRTPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLGK                                        445

SEQ ID NO: 78               moltype = AA  length = 219
FEATURE                     Location/Qualifiers
REGION                      1..219
                            note = source = /note="Description of Artificial Sequence:
                                Syntheticpolypeptide"
source                      1..219
                            mol_type = protein
                            organism = synthetic construct
SEQUENCE: 78
EIVLTQSPAT LSLSPGERAT LSCRSSQSLV HSNGNTYLNW YQQKPGQAPR LLIYKVSNRL    60
SGIPARFSGS GSGTDFTLTI SSLEPEDFAV YYCSQSTHVP YTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 79               moltype = AA  length = 219
FEATURE                     Location/Qualifiers
REGION                      1..219
                            note = source = /note="Description of Artificial Sequence:
                                Syntheticpolypeptide"
source                      1..219
                            mol_type = protein
                            organism = synthetic construct
SEQUENCE: 79
```

```
DVQMTQSPSS LSASVGDRVT ITCRASQSIV HSNGNTYLHW YQQKPGKAPK FLIYKVSNRF    60
SGVPSRFSGS GSGTDFTLTI SSLQPEDFAT YYCAQSTLVP LTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 80           moltype = AA  length = 445
FEATURE                 Location/Qualifiers
REGION                  1..445
                        note = source = /note="Description of Artificial Sequence:
                         Syntheticpolypeptide"
source                  1..445
                        mol_type = protein
                        organism = synthetic construct
SEQUENCE: 80
EVQLVESGGG LIQPGGSLRL SCAASGFTFN AYAMSWVRQA PGKGLEWVSS ISTGGNTYYA    60
DSVKGRFTIS RDNSKNTLYL QMNSLRAEDT AVYYCTRGYQ RFSGFAYWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EVEGGPSVFL   240
FPPKPKDTLM ISRTPEVTCV VVGVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLGK                                        445

SEQ ID NO: 81           moltype = AA  length = 219
FEATURE                 Location/Qualifiers
REGION                  1..219
                        note = source = /note="Description of Artificial Sequence:
                         Syntheticpolypeptide"
source                  1..219
                        mol_type = protein
                        organism = synthetic construct
SEQUENCE: 81
EIVLTQSPAT LSLSPGERAT LSCRSSQSLV HSNGNTYLNW YQQKPGQAPR LLIYKVSNRL    60
SGIPARFSGS GSGTDFTLTI SSLEPEDFAV YYCSQSTHVP YTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 82           moltype = AA  length = 219
FEATURE                 Location/Qualifiers
REGION                  1..219
                        note = source = /note="Description of Artificial Sequence:
                         Syntheticpolypeptide"
source                  1..219
                        mol_type = protein
                        organism = synthetic construct
SEQUENCE: 82
DVQMTQSPSS LSASVGDRVT ITCRASQSIV HSNGNTYLHW YQQKPGKAPK FLIYKVSNRF    60
SGVPSRFSGS GSGTDFTLTI SSLQPEDFAT YYCAQYTLVP LTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 83           moltype = AA  length = 4
FEATURE                 Location/Qualifiers
REGION                  1..4
                        note = source = /note="Description of Artificial Sequence:
                         Syntheticpeptide"
source                  1..4
                        mol_type = protein
                        organism = synthetic construct
SEQUENCE: 83
RTQP                                                                 4

SEQ ID NO: 84           moltype = AA  length = 5
FEATURE                 Location/Qualifiers
REGION                  1..5
                        note = source = /note="Description of Artificial Sequence:
                         Syntheticpeptide"
source                  1..5
                        mol_type = protein
                        organism = synthetic construct
SEQUENCE: 84
TKGPS                                                                5

SEQ ID NO: 85           moltype = AA  length = 5
FEATURE                 Location/Qualifiers
REGION                  1..5
                        note = source = /note="Description of Artificial Sequence:
                         Syntheticpeptide"
source                  1..5
```

```
                       mol_type = protein
                       organism = synthetic construct
SEQUENCE: 85
TVAAP                                                      5

SEQ ID NO: 86          moltype = AA  length = 5
FEATURE                Location/Qualifiers
REGION                 1..5
                       note = source = /note="Description of Artificial Sequence:
                        Syntheticpeptide"
source                 1..5
                       mol_type = protein
                       organism = synthetic construct
SEQUENCE: 86
QPKAA                                                      5
```

The invention claimed is:

1. An antibody or antigen binding fragment thereof that binds complement component 5a receptor 1 (C5aR1), comprising a heavy chain variable (VH) region, wherein the VH comprises three heavy chain complementarity determining regions (HCDRs), wherein the HCDR1, HCDR2, and HCDR3 sequences comprising amino acid sequences of SEQ ID Nos: 6, 7, and 8, respectively and a light chain variable (VL) region, wherein the VL comprises three light chain complementarity determining regions (LCDRs), wherein the LCDR1, LCDR2, and LCDR3 sequences of SEQ ID Nos: 9, 10, and 11, respectively.

2. The antibody or antigen binding fragment thereof of claim 1, wherein the VH comprises an amino acid sequence at least 95% identical to SEQ ID NO: 14.

3. The antibody or antigen binding fragment thereof of claim 2, wherein the VH comprises the amino acid sequence of SEQ ID NO: 14.

4. The antibody or antigen binding fragment thereof of claim 1, wherein the VL comprises an amino acid sequence at least 95% identical to SEQ ID NO: 25.

5. The antibody or antigen binding fragment thereof of claim 4, wherein the VL comprises the amino acid sequence of SEQ ID NO: 25.

6. An antibody or antigen binding fragment thereof, that binds complement component 5a receptor 1 (C5aR1) comprising:
a heavy chain variable region (VH) of SEQ ID NO: 14; and
a light chain variable region (VL) of SEQ ID NO: 25.

7. The antibody or antibody or antigen binding fragment thereof according to claim 1, wherein the antibody or antigen binding fragment thereof, further comprises a Fc region.

8. The antibody or antibody or antigen binding fragment thereof according to claim 7, wherein the Fc domain is independently selected from IgG1, IgG2, IgG3, and IgG4.

9. The antibody or antigen binding fragment thereof of claim 1, wherein the antibody or antigen binding fragment is humanized.

10. The antibody or the antigen binding fragment thereof of claim 1, wherein the VH or the VL has been modified to enhance the stability of the molecule.

11. A nucleic acid encoding the antibody or antigen binding fragment of claim 1.

12. A cell comprising the nucleic acid of claim 11.

13. A composition comprising the antibody or antigen binding fragment of claim 1.

* * * * *

UNITED STATES PATENT AND TRADEMARK OFFICE
CERTIFICATE OF CORRECTION

PATENT NO. : 12,264,203 B2
APPLICATION NO. : 18/731146
DATED : April 1, 2025
INVENTOR(S) : Viswanathan et al.

It is certified that error appears in the above-identified patent and that said Letters Patent is hereby corrected as shown below:

In the Claims

Claim 7, Column 100, Line 23:
Delete "or antibody"

Claim 8, Column 100, Line 27:
Delete "or antibody"

Signed and Sealed this
Seventeenth Day of June, 2025

Coke Morgan Stewart
*Acting Director of the United States Patent and Trademark Office*